United States Patent
Strauss et al.

(10) Patent No.: US 8,795,321 B2
(45) Date of Patent: Aug. 5, 2014

(54) SYSTEM AND METHOD FOR MECHANICALLY POSITIONING INTRAVASCULAR IMPLANTS

(75) Inventors: Brian Michael Strauss, Trabuco Canyon, CA (US); Earl Howard Slee, Laguna Niguel, CA (US); Ramon Torres Carrillo, Santa Ana, CA (US); Khoa Dang Vu, Santa Ana, CA (US); William Robert Patterson, Irvine, CA (US); Jessica Liang, Irvine, CA (US); Richard Stephen Bein, San Clemente, CA (US); Todd Jeffrey Hewitt, Laguna Niguel, CA (US); Stacy Leon Faught, Aliso Viejo, CA (US); Vince Divino, Mission Viejo, CA (US); Darrell Christopher Drysen, Irvine, CA (US); Mark Philip Ashby, Laguna Niguel, CA (US); Justin Arthur Klotz, Los Angeles, CA (US); Maria De Jesus Sanson, San Clemente, CA (US); Scott William Brennan, Laguna Beach, CA (US); Lawrason Charles Wilbur, Lake Forest, CA (US); Lester Eugene Oestreich, Norwalk, CA (US)

(73) Assignee: Covidien LP, Mansfield, MA (US)

( * ) Notice: Subject to any disclaimer, the term of this patent is extended or adjusted under 35 U.S.C. 154(b) by 178 days.

(21) Appl. No.: 13/221,848

(22) Filed: Aug. 30, 2011

(65) Prior Publication Data

US 2012/0226305 A1 Sep. 6, 2012

Related U.S. Application Data

(63) Continuation of application No. 12/297,419, filed as application No. PCT/US2007/066722 on Apr. 16, 2007.

(60) Provisional application No. 60/792,414, filed on Apr. 17, 2006, provisional application No. 60/894,589, filed on Mar. 13, 2007.

(51) Int. Cl.
*A61M 29/00* (2006.01)
*A61B 17/12* (2006.01)

(52) U.S. Cl.
CPC ....... *A61B 17/1214* (2013.01); *A61B 17/12154* (2013.01); *A61B 2017/12054* (2013.01); *A61B 2017/1205* (2013.01)
USPC .......................................................... 606/200

(58) Field of Classification Search
CPC .................. A61B 2017/1205; A61B 17/12054
USPC .................... 606/1, 108, 195, 200; 623/1.11; 128/831, 843
See application file for complete search history.

(56) References Cited

U.S. PATENT DOCUMENTS

| 3,334,629 | A | 8/1967 | Colm |
| 3,834,394 | A | 9/1974 | Hunter et al. |

(Continued)

FOREIGN PATENT DOCUMENTS

| CN | 1668250 A | 9/2005 |
| DE | 4445715 | 6/1996 |

(Continued)

OTHER PUBLICATIONS

US 6,056,761, 5/2000, Gia et al (withdrawn).

(Continued)

*Primary Examiner* — Darwin Erezo
*Assistant Examiner* — Jonathan Hollm
(74) *Attorney, Agent, or Firm* — Elizabeth A. O'Brien, Esq.

(57) ABSTRACT

An intravascular implant delivery system carries an implant by retaining an engagement member engaging the implant in a position proximal of an aperture at a distal end of the delivery system. The engagement member is retained proximal to the aperture by a cord that obstructs the movement of the engagement member through the aperture. The engagement member is free to rotate and move within an area defined by the delivery system, allowing the implant to react to forces imparted to the implant by the movement of the delivery system and implant through a delivery catheter. Once the implant is in a desired implant position, the cord is moved away from an aperture and the engagement member is allowed to move away from the delivery system.

16 Claims, 29 Drawing Sheets

(56) References Cited

U.S. PATENT DOCUMENTS

| | | |
|---|---|---|
| 4,085,757 A | 4/1978 | Pevsner |
| 4,282,875 A | 8/1981 | Serbinenko et al. |
| 4,311,146 A | 1/1982 | Wonder |
| 4,327,734 A | 5/1982 | White, Jr. |
| 4,341,218 A | 7/1982 | U |
| 4,346,712 A | 8/1982 | Handa et al. |
| 4,364,392 A | 12/1982 | Strother et al. |
| 4,402,319 A | 9/1983 | Handa et al. |
| 4,441,495 A | 4/1984 | Hicswa |
| 4,494,531 A | 1/1985 | Gianturco |
| 4,517,979 A | 5/1985 | Pecenka |
| 4,545,367 A | 10/1985 | Tucci |
| 4,638,803 A | 1/1987 | Rand |
| 4,735,201 A | 4/1988 | O'Reilly |
| 4,781,177 A | 11/1988 | Lebigot |
| 4,832,055 A | 5/1989 | Palestrant |
| 4,944,746 A | 7/1990 | Iwata et al. |
| 4,957,501 A | 9/1990 | Lahille et al. |
| 4,990,155 A | 2/1991 | Wilkoff |
| 4,994,069 A | 2/1991 | Ritchart et al. |
| 5,002,556 A | 3/1991 | Ishida et al. |
| 5,026,377 A | 6/1991 | Burton et al. |
| 5,035,706 A | 7/1991 | Giantureo et al. |
| 5,037,427 A | 8/1991 | Harada et al. |
| 5,062,829 A | 11/1991 | Pryor et al. |
| 5,104,399 A | 4/1992 | Lazarus |
| 5,108,407 A | 4/1992 | Geremia et al. |
| 5,109,867 A | 5/1992 | Twyford, Jr. |
| 5,122,136 A | 6/1992 | Guglielmi et al. |
| 5,133,731 A | 7/1992 | Butler et al. |
| 5,133,732 A | 7/1992 | Wiktor |
| 5,147,370 A | 9/1992 | McNamara et al. |
| 5,167,624 A | 12/1992 | Butler et al. |
| 5,181,921 A | 1/1993 | Makita et al. |
| 5,192,301 A | 3/1993 | Kamiya et al. |
| 5,211,658 A | 5/1993 | Clouse |
| 5,217,484 A | 6/1993 | Marks |
| 5,222,970 A | 6/1993 | Reeves |
| 5,224,953 A | 7/1993 | Morgentaler |
| 5,226,911 A | 7/1993 | Chee et al. |
| 5,234,437 A | 8/1993 | Sepetka |
| 5,250,071 A | 10/1993 | Palermo |
| 5,256,146 A | 10/1993 | Ensminger et al. |
| 5,261,916 A | 11/1993 | Engelson |
| 5,263,964 A | 11/1993 | Purdy |
| 5,282,806 A | 2/1994 | Haber et al. |
| 5,304,194 A | 4/1994 | Chee et al. |
| 5,304,195 A * | 4/1994 | Twyford et al. ............... 606/191 |
| 5,312,415 A | 5/1994 | Palermo |
| 5,314,472 A | 5/1994 | Fontaine |
| 5,334,210 A | 8/1994 | Gianturco |
| 5,350,397 A | 9/1994 | Palermo et al. |
| 5,354,295 A | 10/1994 | Guglielmi et al. |
| 5,368,592 A | 11/1994 | Stern et al. |
| 5,382,259 A | 1/1995 | Phelps et al. |
| 5,382,260 A | 1/1995 | Dormandy, Jr. et al. |
| 5,382,261 A | 1/1995 | Palmaz |
| 5,397,345 A | 3/1995 | Lazarus |
| 5,417,708 A | 5/1995 | Hall |
| 5,423,829 A | 6/1995 | Pham et al. |
| 5,423,849 A | 6/1995 | Engelson et al. |
| 5,443,454 A | 8/1995 | Tanabe et al. |
| 5,443,478 A | 8/1995 | Purdy |
| 5,456,693 A | 10/1995 | Conston et al. |
| 5,476,472 A | 12/1995 | Dormandy, Jr. et al. |
| 5,480,382 A | 1/1996 | Hammerslag et al. |
| 5,490,859 A | 2/1996 | Mische et al. |
| 5,498,227 A | 3/1996 | Mawad |
| 5,499,985 A | 3/1996 | Hein et al. |
| 5,507,769 A | 4/1996 | Marin et al. |
| 5,522,822 A | 6/1996 | Phelps et al. |
| 5,522,836 A | 6/1996 | Palermo |
| 5,527,338 A | 6/1996 | Purdy |
| 5,536,274 A | 7/1996 | Neuss |
| 5,540,680 A | 7/1996 | Guglielmi et al. |
| 5,549,624 A | 8/1996 | Mirigian et al. |
| 5,562,698 A | 10/1996 | Parker |
| 5,569,245 A | 10/1996 | Guglielmi et al. |
| 5,573,520 A | 11/1996 | Schwartz |
| 5,578,074 A | 11/1996 | Mirigian |
| 5,582,619 A | 12/1996 | Ken |
| 5,601,600 A | 2/1997 | Ton |
| 5,624,449 A | 4/1997 | Pham et al. |
| 5,624,461 A | 4/1997 | Mariant |
| 5,626,599 A | 5/1997 | Bourne et al. |
| 5,634,928 A | 6/1997 | Fischell et al. |
| 5,639,277 A | 6/1997 | Mariant et al. |
| 5,643,254 A | 7/1997 | Scheldrup et al. |
| 5,645,558 A | 7/1997 | Horton |
| 5,645,564 A | 7/1997 | Northrup et al. |
| 5,649,949 A | 7/1997 | Wallace et al. |
| 5,658,308 A | 8/1997 | Snyder |
| 5,662,700 A | 9/1997 | Lazarus |
| 5,669,905 A | 9/1997 | Scheldrup et al. |
| 5,669,931 A | 9/1997 | Kupiecki et al. |
| 5,690,666 A | 11/1997 | Berenstein et al. |
| 5,690,667 A | 11/1997 | Gia |
| 5,690,671 A | 11/1997 | McGurk et al. |
| 5,693,067 A | 12/1997 | Purdy |
| 5,695,517 A | 12/1997 | Marin et al. |
| 5,700,258 A | 12/1997 | Mirigian et al. |
| 5,702,361 A | 12/1997 | Evans et al. |
| 5,718,711 A | 2/1998 | Berenstein et al. |
| 5,725,534 A | 3/1998 | Rasmussen |
| 5,725,546 A | 3/1998 | Samson |
| 5,725,552 A | 3/1998 | Kotula et al. |
| 5,728,129 A | 3/1998 | Summers |
| 5,733,329 A | 3/1998 | Wallace et al. |
| 5,743,905 A | 4/1998 | Eder et al. |
| 5,746,734 A | 5/1998 | Dormandy, Jr. et al. |
| 5,746,769 A | 5/1998 | Ton et al. |
| 5,749,891 A | 5/1998 | Ken et al. |
| 5,749,894 A | 5/1998 | Engelson |
| 5,749,918 A | 5/1998 | Hogendijk et al. |
| 5,759,161 A | 6/1998 | Ogawa et al. |
| 5,766,219 A | 6/1998 | Horton |
| 5,797,953 A | 8/1998 | Tekulve |
| 5,800,426 A | 9/1998 | Taki et al. |
| 5,800,453 A | 9/1998 | Gia |
| 5,800,455 A | 9/1998 | Palermo et al. |
| 5,814,062 A | 9/1998 | Sepetka et al. |
| 5,830,230 A | 11/1998 | Berryman et al. |
| 5,833,705 A | 11/1998 | Ken et al. |
| 5,843,118 A | 12/1998 | Sepetka et al. |
| 5,846,210 A | 12/1998 | Ogawa et al. |
| 5,851,206 A | 12/1998 | Guglielmi et al. |
| 5,853,418 A | 12/1998 | Ken et al. |
| 5,855,578 A | 1/1999 | Guglielmi et al. |
| 5,891,058 A | 4/1999 | Taki et al. |
| 5,891,128 A | 4/1999 | Gia et al. |
| 5,891,130 A | 4/1999 | Palermo et al. |
| 5,891,155 A | 4/1999 | Irie |
| 5,891,192 A | 4/1999 | Murayama et al. |
| 5,895,385 A | 4/1999 | Guglielmi et al. |
| 5,895,391 A * | 4/1999 | Farnholtz ..................... 606/108 |
| 5,895,410 A | 4/1999 | Forber et al. |
| 5,895,411 A | 4/1999 | Irie |
| 5,911,731 A | 6/1999 | Pham et al. |
| 5,911,737 A | 6/1999 | Lee et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,059 A | 7/1999 | Palermo et al. |
| 5,925,060 A | 7/1999 | Forber |
| 5,925,062 A | 7/1999 | Purdy |
| 5,928,226 A | 7/1999 | Guglielmi et al. |
| 5,935,145 A | 8/1999 | Villar et al. |
| 5,935,148 A | 8/1999 | Villar et al. |
| 5,941,249 A | 8/1999 | Maynard |
| 5,941,888 A | 8/1999 | Wallace |
| 5,944,714 A | 8/1999 | Guglielmi et al. |
| 5,944,733 A | 8/1999 | Engelson |
| 5,947,962 A | 9/1999 | Guglielmi et al. |
| 5,947,963 A | 9/1999 | Guglieli |

(56) References Cited

U.S. PATENT DOCUMENTS

| | | |
|---|---|---|
| 5,957,948 A | 9/1999 | Mariant |
| 5,964,797 A | 10/1999 | Ho |
| 5,972,019 A | 10/1999 | Engelson et al. |
| 5,976,126 A | 11/1999 | Guglielmi |
| 5,976,131 A | 11/1999 | Guglielmi |
| 5,976,152 A | 11/1999 | Regan et al. |
| 5,976,162 A | 11/1999 | Doan et al. |
| 5,980,514 A | 11/1999 | Kupiecki et al. |
| 5,980,550 A | 11/1999 | Eder et al. |
| 5,980,554 A | 11/1999 | Lenker et al. |
| 5,984,929 A | 11/1999 | Bashiri et al. |
| 5,984,944 A | 11/1999 | Forber |
| 5,989,242 A | 11/1999 | Saadat et al. |
| 6,001,092 A | 12/1999 | Mirigian et al. |
| 6,004,338 A | 12/1999 | Ken et al. |
| 6,010,498 A | 1/2000 | Guglielmi |
| 6,013,084 A | 1/2000 | Ken et al. |
| 6,015,424 A | 1/2000 | Rosenbluth et al. |
| 6,017,364 A | 1/2000 | Lazarus |
| 6,017,977 A | 1/2000 | Evans et al. |
| 6,019,757 A | 2/2000 | Scheldrup |
| 6,022,369 A | 2/2000 | Jacobsen et al. |
| 6,024,754 A | 2/2000 | Engelson |
| 6,024,765 A | 2/2000 | Wallace et al. |
| 6,030,413 A | 2/2000 | Lazarus |
| 6,033,423 A | 3/2000 | Ken et al. |
| 6,039,744 A | 3/2000 | Forber |
| 6,039,749 A | 3/2000 | Marin et al. |
| 6,056,770 A | 5/2000 | Epstein et al. |
| 6,059,779 A | 5/2000 | Mills |
| 6,059,815 A | 5/2000 | Lee et al. |
| 6,063,070 A | 5/2000 | Eder |
| 6,063,100 A | 5/2000 | Diaz et al. |
| 6,063,104 A | 5/2000 | Villar et al. |
| 6,066,133 A | 5/2000 | Guglielmi et al. |
| 6,066,149 A | 5/2000 | Samson et al. |
| 6,068,644 A | 5/2000 | Lulo et al. |
| 6,074,407 A | 6/2000 | Levine et al. |
| 6,077,260 A | 6/2000 | Wheelock et al. |
| D427,680 S | 7/2000 | Mariant et al. |
| 6,083,220 A | 7/2000 | Guglielmi et al. |
| 6,086,577 A | 7/2000 | Ken et al. |
| 6,090,125 A | 7/2000 | Horton |
| 6,093,199 A | 7/2000 | Brown et al. |
| 6,096,034 A | 8/2000 | Kupiecki et al. |
| 6,099,546 A | 8/2000 | Gia |
| 6,102,917 A | 8/2000 | Maitland et al. |
| 6,102,932 A | 8/2000 | Kurz |
| 6,102,933 A | 8/2000 | Lee et al. |
| 6,113,622 A | 9/2000 | Hieshima |
| 6,117,142 A | 9/2000 | Goodson et al. |
| 6,123,714 A | 9/2000 | Gia et al. |
| 6,126,672 A | 10/2000 | Berryman et al. |
| 6,136,015 A | 10/2000 | Kurz et al. |
| 6,143,007 A | 11/2000 | Mariant et al. |
| 6,146,373 A | 11/2000 | Cragg et al. |
| 6,149,644 A | 11/2000 | Xie |
| 6,149,681 A | 11/2000 | Houser et al. |
| 6,152,947 A | 11/2000 | Ambrisco et al. |
| 6,156,061 A | 12/2000 | Wallace et al. |
| 6,159,165 A | 12/2000 | Ferrera et al. |
| 6,159,206 A | 12/2000 | Ogawa |
| 6,165,178 A | 12/2000 | Bashiri et al. |
| 6,165,193 A | 12/2000 | Greene, Jr. et al. |
| 6,165,198 A | 12/2000 | McGurk et al. |
| 6,168,570 B1 | 1/2001 | Ferrera |
| 6,168,592 B1 | 1/2001 | Kupiecki et al. |
| 6,168,610 B1 | 1/2001 | Marin et al. |
| 6,168,615 B1 | 1/2001 | Ken et al. |
| 6,168,622 B1 | 1/2001 | Mazzocchi |
| 6,171,326 B1 | 1/2001 | Ferrera et al. |
| 6,183,491 B1 | 2/2001 | Lulo |
| 6,183,495 B1 | 2/2001 | Lenker et al. |
| 6,187,024 B1 | 2/2001 | Boock et al. |
| 6,187,027 B1 | 2/2001 | Mariant et al. |
| 6,190,373 B1 | 2/2001 | Palermo et al. |
| 6,193,708 B1 | 2/2001 | Ken et al. |
| 6,193,728 B1 | 2/2001 | Ken et al. |
| RE37,117 E | 3/2001 | Palermo et al. |
| 6,202,261 B1 | 3/2001 | Moore et al. |
| 6,203,547 B1 | 3/2001 | Nguyen et al. |
| 6,221,066 B1 | 4/2001 | Ferrera et al. |
| 6,221,086 B1 | 4/2001 | Forber |
| 6,224,610 B1 | 5/2001 | Ferrera |
| 6,231,573 B1 | 5/2001 | Amor et al. |
| 6,231,586 B1 | 5/2001 | Mariant |
| 6,231,590 B1 | 5/2001 | Slaikeu et al. |
| 6,231,597 B1 | 5/2001 | Deem et al. |
| 6,238,403 B1 | 5/2001 | Greene, Jr. et al. |
| 6,238,415 B1 | 5/2001 | Sepetka et al. |
| 6,241,691 B1 | 6/2001 | Ferrera et al. |
| 6,254,592 B1 | 7/2001 | Samson et al. |
| 6,270,495 B1 | 8/2001 | Palermo |
| 6,270,508 B1 | 8/2001 | Klieman et al. |
| 6,277,125 B1 | 8/2001 | Barry et al. |
| 6,277,126 B1 | 8/2001 | Barry et al. |
| 6,280,457 B1 | 8/2001 | Wallace et al. |
| 6,281,263 B1 | 8/2001 | Evans et al. |
| 6,287,315 B1 | 9/2001 | Wijeratne et al. |
| 6,287,318 B1 | 9/2001 | Villar et al. |
| 6,293,960 B1 | 9/2001 | Ken |
| 6,296,622 B1 | 10/2001 | Kurz et al. |
| 6,299,619 B1 | 10/2001 | Greene, Jr. et al. |
| 6,299,627 B1 | 10/2001 | Eder et al. |
| 6,306,153 B1 | 10/2001 | Kurz et al. |
| 6,312,405 B1 | 11/2001 | Meyer et al. |
| 6,312,421 B1 | 11/2001 | Boock |
| 6,315,709 B1 | 11/2001 | Garibaldi et al. |
| 6,319,267 B1 | 11/2001 | Kurz |
| 6,322,576 B1 | 11/2001 | Wallace et al. |
| 6,331,184 B1 | 12/2001 | Abrams |
| 6,335,384 B1 | 1/2002 | Evans et al. |
| 6,344,041 B1 | 2/2002 | Kupiecki et al. |
| 6,344,048 B1 | 2/2002 | Chin et al. |
| 6,346,091 B1 | 2/2002 | Jacobsen et al. |
| 6,348,041 B1 | 2/2002 | Klint |
| 6,361,547 B1 | 3/2002 | Hieshima |
| 6,364,823 B1 | 4/2002 | Garibaldi et al. |
| 6,368,338 B1 | 4/2002 | Konya et al. |
| 6,371,972 B1 | 4/2002 | Wallace et al. |
| 6,375,606 B1 | 4/2002 | Garibaldi et al. |
| 6,375,628 B1 | 4/2002 | Zadno-Azizi et al. |
| 6,375,668 B1 | 4/2002 | Gifford et al. |
| 6,375,669 B1 | 4/2002 | Rosenbluth et al. |
| 6,379,329 B1 | 4/2002 | Naglreiter et al. |
| 6,379,374 B1 | 4/2002 | Hieshima et al. |
| 6,383,146 B1 | 5/2002 | Klint |
| 6,383,174 B1 | 5/2002 | Eder |
| 6,383,204 B1 | 5/2002 | Ferrera et al. |
| 6,383,205 B1 | 5/2002 | Samson et al. |
| 6,397,850 B1 | 6/2002 | Scheldrup et al. |
| 6,409,721 B1 | 6/2002 | Wheelock et al. |
| 6,416,535 B1 | 7/2002 | Lazarus |
| 6,416,541 B2 | 7/2002 | Denardo |
| 6,423,085 B1 | 7/2002 | Murayama et al. |
| 6,425,893 B1 | 7/2002 | Guglielmi et al. |
| 6,425,914 B1 | 7/2002 | Wallace et al. |
| 6,428,557 B1 | 8/2002 | Hilaire |
| 6,428,558 B1 | 8/2002 | Jones et al. |
| 6,454,780 B1 | 9/2002 | Wallace |
| 6,458,119 B1 | 10/2002 | Berenstein et al. |
| 6,458,127 B1 | 10/2002 | Truckai et al. |
| 6,458,137 B1 | 10/2002 | Klint |
| 6,464,699 B1 | 10/2002 | Swanson |
| 6,468,266 B1 | 10/2002 | Bashiri et al. |
| 6,475,169 B2 | 11/2002 | Ferrera |
| 6,475,227 B2 | 11/2002 | Burke et al. |
| 6,478,773 B1 | 11/2002 | Gandhi et al. |
| 6,485,524 B2 | 11/2002 | Strecker |
| 6,494,884 B2 | 12/2002 | Gifford, III et al. |
| 6,500,149 B2 | 12/2002 | Gandhi et al. |
| 6,500,190 B2 | 12/2002 | Greene, Jr. et al. |
| 6,506,204 B2 | 1/2003 | Mazzocchi et al. |
| 6,511,468 B1 | 1/2003 | Cragg et al. |

(56) References Cited

U.S. PATENT DOCUMENTS

| | | |
|---|---|---|
| 6,514,264 B1 | 2/2003 | Naglreiter |
| 6,530,934 B1 | 3/2003 | Jacobsen et al. |
| 6,533,801 B2 | 3/2003 | Wallace et al. |
| 6,537,293 B1 | 3/2003 | Berryman et al. |
| 6,540,657 B2 | 4/2003 | Cross, III et al. |
| 6,544,163 B2 | 4/2003 | Wallace et al. |
| 6,544,225 B1 | 4/2003 | Lulo et al. |
| 6,544,268 B1 | 4/2003 | Lazarus |
| 6,544,275 B1 | 4/2003 | Teoh et al. |
| 6,547,804 B2 | 4/2003 | Porter et al. |
| 6,551,305 B2 | 4/2003 | Ferrera et al. |
| 6,551,340 B1 | 4/2003 | Konya et al. |
| 6,554,849 B1 | 4/2003 | Jones et al. |
| 6,558,367 B1 | 5/2003 | Cragg et al. |
| 6,569,179 B2 | 5/2003 | Teoh et al. |
| 6,572,628 B2 | 6/2003 | Dominguez et al. |
| 6,575,994 B1 | 6/2003 | Marin et al. |
| 6,585,748 B1 | 7/2003 | Jeffree |
| 6,585,754 B2 | 7/2003 | Wallace et al. |
| 6,589,227 B2 | 7/2003 | Sønderskov Klint |
| 6,589,230 B2 | 7/2003 | Gia et al. |
| 6,589,236 B2 | 7/2003 | Wheelock et al. |
| 6,589,251 B2 | 7/2003 | Yee et al. |
| 6,589,265 B1 | 7/2003 | Palmer et al. |
| 6,592,605 B2 | 7/2003 | Lenkar et al. |
| 6,602,261 B2 | 8/2003 | Greene et al. |
| 6,602,269 B2 | 8/2003 | Wallace et al. |
| 6,603,994 B2 | 8/2003 | Wallace et al. |
| 6,605,101 B1 | 8/2003 | Schaefer et al. |
| 6,607,538 B1 | 8/2003 | Ferrera et al. |
| 6,607,539 B1 | 8/2003 | Hayashi et al. |
| 6,610,085 B1 | 8/2003 | Lazarus |
| 6,613,074 B1 | 9/2003 | Mitelberg et al. |
| 6,616,617 B1 | 9/2003 | Ferrera et al. |
| 6,620,152 B2 | 9/2003 | Guglielmi |
| 6,623,493 B2 | 9/2003 | Wallace et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,638,291 B1 | 10/2003 | Ferrera et al. |
| 6,638,293 B1 | 10/2003 | Makower et al. |
| 6,656,173 B1 | 12/2003 | Palermo |
| 6,656,201 B2 | 12/2003 | Ferrera et al. |
| 6,656,218 B1 | 12/2003 | Denardo et al. |
| 6,656,351 B2 | 12/2003 | Boyle |
| 6,660,020 B2 | 12/2003 | Wallace et al. |
| 6,663,607 B2 | 12/2003 | Slaikeu et al. |
| 6,679,903 B2 | 1/2004 | Kurz |
| 6,685,653 B2 | 2/2004 | Ehr et al. |
| 6,689,141 B2 | 2/2004 | Ferrera et al. |
| 6,692,510 B2 | 2/2004 | West |
| 6,702,844 B1 | 3/2004 | Lazarus |
| 6,716,238 B2 | 4/2004 | Elliott |
| 6,723,112 B2 | 4/2004 | Ho et al. |
| 6,743,236 B2 | 6/2004 | Barry et al. |
| 6,743,251 B1 | 6/2004 | Eder |
| 6,767,358 B2 | 7/2004 | Leonhardt et al. |
| 6,811,561 B2 | 11/2004 | Diaz et al. |
| 6,814,748 B1 | 11/2004 | Baker et al. |
| 6,835,185 B2 | 12/2004 | Ramzipoor et al. |
| 6,849,081 B2 | 2/2005 | Sepetka et al. |
| 6,852,116 B2 | 2/2005 | Leonhardt et al. |
| 6,853,418 B2 | 2/2005 | Suzuki et al. |
| 6,855,153 B2 | 2/2005 | Saadat |
| 6,855,155 B2 | 2/2005 | Denardo et al. |
| 6,860,893 B2 | 3/2005 | Wallace et al. |
| 6,860,901 B1 | 3/2005 | Baker et al. |
| 6,872,218 B2 | 3/2005 | Ferrera et al. |
| 6,878,163 B2 | 4/2005 | Denardo et al. |
| 6,905,503 B2 | 6/2005 | Gifford, III et al. |
| 6,913,618 B2 | 7/2005 | Denardo et al. |
| 6,929,654 B2 | 8/2005 | Teoh et al. |
| 6,945,956 B2 | 9/2005 | Waldhauser et al. |
| 6,958,061 B2 | 10/2005 | Truckai et al. |
| 6,958,068 B2 | 10/2005 | Hieshma |
| 6,964,657 B2 | 11/2005 | Cragg et al. |
| 6,966,892 B2 | 11/2005 | Gandhi et al. |
| 6,994,689 B1 | 2/2006 | Zadno-Azizi et al. |
| 6,994,711 B2 | 2/2006 | Hieshima et al. |
| 7,014,645 B2 | 3/2006 | Greene, Jr. et al. |
| 7,022,133 B2 | 4/2006 | Yee et al. |
| 7,029,486 B2 | 4/2006 | Schaefer et al. |
| 7,029,487 B2 | 4/2006 | Greene, Jr. et al. |
| 7,033,374 B2 | 4/2006 | Schaefer et al. |
| 7,058,456 B2 | 6/2006 | Pierce |
| 7,060,083 B2 | 6/2006 | Gerberding |
| 7,070,607 B2 | 7/2006 | Murayama et al. |
| 7,147,618 B2 | 12/2006 | Kurz |
| 7,169,161 B2 | 1/2007 | Bonnette et al. |
| 7,182,774 B2 | 2/2007 | Barry et al. |
| 7,198,613 B2 | 4/2007 | Gandhi et al. |
| 7,238,194 B2 | 7/2007 | Monstadt et al. |
| 7,294,146 B2 | 11/2007 | Chew et al. |
| 7,300,458 B2 | 11/2007 | Henkes et al. |
| 7,316,701 B2 | 1/2008 | Ferrera et al. |
| 7,323,000 B2 | 1/2008 | Mondstadt et al. |
| 7,331,973 B2 | 2/2008 | Gesswein et al. |
| 7,344,558 B2 | 3/2008 | Lorenzo et al. |
| 7,377,932 B2 | 5/2008 | Mitelberg et al. |
| 7,410,482 B2 | 8/2008 | Murphy et al. |
| 7,419,501 B2 | 9/2008 | Chiu et al. |
| 7,473,266 B2 | 1/2009 | Glaser |
| 7,485,122 B2 | 2/2009 | Teoh |
| 7,485,317 B1 | 2/2009 | Murayama et al. |
| 7,524,322 B2 | 4/2009 | Mondstadt et al. |
| 7,575,582 B2 | 8/2009 | Gandhi et al. |
| 7,578,826 B2 | 8/2009 | Gandhi et al. |
| 7,591,829 B2 | 9/2009 | Gibson et al. |
| RE41,029 E | 12/2009 | Guglielmi et al. |
| 7,691,124 B2 | 4/2010 | Balgobin |
| 7,708,755 B2 | 5/2010 | Davis, III et al. |
| 7,722,636 B2 | 5/2010 | Farnan |
| 7,722,637 B2 | 5/2010 | Barry et al. |
| 7,811,305 B2 | 10/2010 | Balgobin et al. |
| 7,879,064 B2 | 2/2011 | Monstadt et al. |
| 7,896,899 B2 | 3/2011 | Patterson et al. |
| 7,901,444 B2 | 3/2011 | Slazas |
| 7,918,872 B2 | 4/2011 | Mitelberg et al. |
| 8,007,509 B2 | 8/2011 | Buiser et al. |
| RE42,758 E | 9/2011 | Ken et al. |
| 8,016,852 B2 | 9/2011 | Ho et al. |
| 8,029,466 B2 | 10/2011 | Wilson et al. |
| 8,034,073 B2 | 10/2011 | Davis, III et al. |
| 8,100,918 B2 | 1/2012 | Gandhi et al. |
| 8,142,456 B2 | 3/2012 | Rosqueta et al. |
| 2001/0037141 A1 | 11/2001 | Yee et al. |
| 2002/0010481 A1 | 1/2002 | Jayaraman |
| 2002/0065529 A1 | 5/2002 | Laurent et al. |
| 2002/0072712 A1 | 6/2002 | Nool et al. |
| 2002/0072791 A1 | 6/2002 | Eder et al. |
| 2002/0082620 A1 | 6/2002 | Lee |
| 2002/0087184 A1 | 7/2002 | Eder et al. |
| 2002/0116024 A1 | 8/2002 | Goldberg et al. |
| 2002/0120297 A1 | 8/2002 | Shadduck |
| 2002/0128671 A1 | 9/2002 | Wallace et al. |
| 2002/0138095 A1 | 9/2002 | Mazzocchi et al. |
| 2002/0143349 A1 | 10/2002 | Gifford, III et al. |
| 2002/0169473 A1 | 11/2002 | Sepetka et al. |
| 2003/0014073 A1 | 1/2003 | Bashiri et al. |
| 2003/0040733 A1 | 2/2003 | Cragg et al. |
| 2003/0083676 A1 | 5/2003 | Wallace |
| 2003/0130689 A1 | 7/2003 | Wallace et al. |
| 2003/0169473 A1 | 9/2003 | Cotter et al. |
| 2003/0171770 A1 | 9/2003 | Kusleika et al. |
| 2003/0176857 A1 | 9/2003 | Lee |
| 2003/0181927 A1 | 9/2003 | Wallace |
| 2003/0199966 A1 | 10/2003 | Shiu et al. |
| 2003/0225365 A1 | 12/2003 | Greff et al. |
| 2004/0002731 A1 | 1/2004 | Aganon et al. |
| 2004/0002732 A1 | 1/2004 | Teoh et al. |
| 2004/0002733 A1 | 1/2004 | Teoh |
| 2004/0024394 A1 | 2/2004 | Wallace et al. |
| 2004/0034363 A1* | 2/2004 | Wilson et al. ............... 606/108 |
| 2004/0106946 A1 | 6/2004 | Ferrera et al. |

(56) References Cited

U.S. PATENT DOCUMENTS

| | | |
|---|---|---|
| 2004/0181256 A1* | 9/2004 | Glaser .................... 606/213 |
| 2004/0193178 A1 | 9/2004 | Nikolchev |
| 2004/0193206 A1 | 9/2004 | Gerberding et al. |
| 2004/0220563 A1 | 11/2004 | Eder |
| 2004/0220585 A1 | 11/2004 | Nikolchev |
| 2004/0225279 A1 | 11/2004 | Raymond |
| 2004/0243228 A1 | 12/2004 | Kowalsky et al. |
| 2005/0021023 A1 | 1/2005 | Guglielmi et al. |
| 2005/0079196 A1 | 4/2005 | Henkes et al. |
| 2006/0025792 A1 | 2/2006 | Gibson et al. |
| 2006/0025801 A1 | 2/2006 | Lulo et al. |
| 2006/0025802 A1 | 2/2006 | Sowers |
| 2006/0036281 A1 | 2/2006 | Paterson |
| 2006/0079926 A1 | 4/2006 | Desai |
| 2006/0106417 A1 | 5/2006 | Tessmer et al. |
| 2006/0116714 A1 | 6/2006 | Sepetka et al. |
| 2006/0271097 A1 | 11/2006 | Ramipoor et al. |
| 2006/0276823 A1 | 12/2006 | Mitelberg et al. |
| 2006/0276824 A1 | 12/2006 | Mitelberg et al. |
| 2006/0278680 A1 | 12/2006 | Viola et al. |
| 2007/0055302 A1 | 3/2007 | Henry |
| 2007/0173757 A1 | 7/2007 | Levine et al. |
| 2007/0179520 A1 | 8/2007 | West |
| 2007/0185524 A1 | 8/2007 | Diaz et al. |
| 2007/0239193 A1* | 10/2007 | Simon et al. .................. 606/191 |
| 2007/0267281 A1 | 11/2007 | Smith |
| 2007/0270936 A1 | 11/2007 | Andreas et al. |
| 2008/0045922 A1 | 2/2008 | Cragg et al. |
| 2008/0045997 A1 | 2/2008 | Balgobin et al. |
| 2008/0051803 A1 | 2/2008 | Mondstadt et al. |
| 2008/0097462 A1 | 4/2008 | Mitelberg et al. |
| 2008/0103585 A1 | 5/2008 | Mondstadt et al. |
| 2008/0125855 A1 | 5/2008 | Henkes et al. |
| 2008/0228215 A1 | 9/2008 | Strauss et al. |
| 2008/0228216 A1 | 9/2008 | Strauss et al. |
| 2008/0243106 A1 | 10/2008 | Coe et al. |
| 2008/0255542 A1 | 10/2008 | Nimgaard et al. |
| 2008/0300616 A1 | 12/2008 | Que et al. |
| 2008/0306504 A1 | 12/2008 | Win et al. |
| 2008/0319532 A1 | 12/2008 | Mondstadt et al. |
| 2009/0012554 A1 | 1/2009 | Makower et al. |
| 2009/0018653 A1 | 1/2009 | Bashiri et al. |
| 2009/0024154 A1 | 1/2009 | Williams et al. |
| 2009/0062812 A1 | 3/2009 | Fitz et al. |
| 2009/0088832 A1 | 4/2009 | Chew et al. |
| 2009/0138036 A1 | 5/2009 | Nardone et al. |
| 2009/0163780 A1 | 6/2009 | Tieu |
| 2009/0163986 A1 | 6/2009 | Tieu et al. |
| 2009/0177261 A1 | 7/2009 | Teoh et al. |
| 2009/0182268 A1 | 7/2009 | Thielen et al. |
| 2009/0254111 A1 | 10/2009 | Mondstadt et al. |
| 2009/0254169 A1 | 10/2009 | Spenser et al. |
| 2009/0270877 A1 | 10/2009 | Johnson et al. |
| 2009/0287291 A1 | 11/2009 | Becking et al. |
| 2009/0312748 A1 | 12/2009 | Johnson et al. |
| 2010/0004673 A1 | 1/2010 | Denison et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0076479 A1 | 3/2010 | Mondstadt |
| 2010/0094395 A1 | 4/2010 | Kellett |
| 2010/0174269 A1 | 7/2010 | Tompkins et al. |
| 2010/0234872 A1 | 9/2010 | Guo et al. |
| 2010/0256666 A1 | 10/2010 | Chen et al. |
| 2010/0268204 A1 | 10/2010 | Tieu et al. |
| 2010/0268251 A1 | 10/2010 | Chen et al. |
| 2010/0268252 A1 | 10/2010 | Chen et al. |
| 2011/0022003 A1 | 1/2011 | Tekulve |
| 2011/0098814 A1 | 4/2011 | Monstadt |
| 2011/0106098 A1 | 5/2011 | Williams |
| 2011/0106128 A1 | 5/2011 | Chen |
| 2011/0118772 A1 | 5/2011 | Chen et al. |
| 2011/0118776 A1 | 5/2011 | Chen et al. |
| 2011/0118777 A1 | 5/2011 | Patterson |
| 2011/0172700 A1 | 7/2011 | Bose et al. |
| 2011/0202085 A1 | 8/2011 | Loganathan |
| 2011/0208227 A1 | 8/2011 | Becking |
| 2011/0265943 A1 | 11/2011 | Rosqueta et al. |
| 2011/0282380 A1 | 11/2011 | Davis et al. |
| 2011/0301686 A1 | 12/2011 | Bowman et al. |
| 2011/0313447 A1 | 12/2011 | Strauss |
| 2012/0041470 A1 | 2/2012 | Shrivastava |
| 2012/0041472 A1 | 2/2012 | Tan et al. |
| 2012/0046687 A1 | 2/2012 | Trommeter et al. |
| 2012/0065720 A1 | 3/2012 | Strauss |
| 2012/0313447 A1 | 12/2012 | Park et al. |
| 2012/0316598 A1 | 12/2012 | Becking et al. |
| 2012/0330347 A1 | 12/2012 | Becking et al. |
| 2013/0066360 A1 | 3/2013 | Becking et al. |
| 2013/0085520 A1 | 4/2013 | Liang et al. |
| 2013/0085521 A1 | 4/2013 | Lim |
| 2013/0085522 A1 | 4/2013 | Becking et al. |
| 2013/0123830 A1 | 5/2013 | Becking et al. |
| 2013/0138136 A1 | 5/2013 | Beckham |
| 2013/0211495 A1 | 8/2013 | Halden |

FOREIGN PATENT DOCUMENTS

| | | |
|---|---|---|
| DE | 69627243 | 1/1997 |
| DE | 19547617 | 9/1997 |
| DE | 19607451 | 9/1997 |
| DE | 19610333 | 9/1997 |
| DE | 19647280 | 10/1997 |
| DE | 19952387 | 5/2001 |
| DE | 10010840 | 9/2001 |
| DE | 10118017 | 10/2002 |
| DE | 10155191 | 5/2003 |
| EP | 707 830 | 4/1996 |
| EP | 711 532 | 5/1996 |
| EP | 717969 A2 | 6/1996 |
| EP | 702 838 | 7/1996 |
| EP | 765636 A3 | 7/1997 |
| EP | 820 726 | 1/1998 |
| EP | 830 873 | 3/1998 |
| EP | 829236 A1 | 3/1998 |
| EP | 853 955 | 7/1998 |
| EP | 865 773 | 9/1998 |
| EP | 882 428 | 9/1998 |
| EP | 904 737 | 3/1999 |
| EP | 914 807 | 5/1999 |
| EP | 941 700 | 9/1999 |
| EP | 941 701 | 9/1999 |
| EP | 992 220 | 4/2000 |
| EP | 996372 | 5/2000 |
| EP | 1 005 837 | 6/2000 |
| EP | 1 120 088 | 8/2001 |
| EP | 1 125 553 | 8/2001 |
| EP | 1 129 666 | 9/2001 |
| EP | 1 142 535 | 10/2001 |
| EP | 1 169 969 | 1/2002 |
| EP | 1 188 413 | 3/2002 |
| EP | 1 188 414 | 3/2002 |
| EP | 1 312 312 | 5/2003 |
| EP | 1 316 293 | 6/2003 |
| EP | 1 258 850 | 11/2003 |
| EP | 1400208 | 3/2004 |
| EP | 996372 | 9/2004 |
| EP | 1487526 | 12/2004 |
| EP | 1 669 032 | 6/2006 |
| EP | 1738698 | 1/2007 |
| EP | 832 607 | 4/2008 |
| JP | 6-246004 | 9/1994 |
| JP | 7-155331 | 6/1995 |
| JP | 7-265431 | 10/1995 |
| JP | 7-284534 | 10/1995 |
| JP | 09-149904 | 6/1997 |
| JP | 9-168541 A | 6/1997 |
| JP | 10-127646 | 5/1998 |
| JP | 10-201766 A | 8/1998 |
| JP | 11-47138 | 2/1999 |
| JP | 11-76249 | 3/1999 |
| JP | 2001-513389 A | 9/2001 |
| JP | 2002-523172 A | 7/2002 |
| JP | 2004-500929 A | 1/2004 |

(56) References Cited

FOREIGN PATENT DOCUMENTS

| | | |
|---|---|---|
| JP | 2004/073874 A | 3/2004 |
| JP | 2004-267749 A | 9/2004 |
| JP | 2006-051349 A | 2/2006 |
| JP | 2008-525113 A | 7/2008 |
| JP | 2009-533202 A | 9/2009 |
| WO | WO 88/03817 | 6/1988 |
| WO | WO 89/06984 | 8/1989 |
| WO | WO 90/12616 | 11/1990 |
| WO | WO 91/13592 | 9/1991 |
| WO | WO 92/14408 | 9/1992 |
| WO | WO 92/21400 | 12/1992 |
| WO | WO 93/11719 | 6/1993 |
| WO | WO 93/16650 | 9/1993 |
| WO | WO 94/06502 | 3/1994 |
| WO | WO 94/06503 | 3/1994 |
| WO | WO 94/10936 | 5/1994 |
| WO | WO 94/11051 | 5/1994 |
| WO | WO 94/26175 | 11/1994 |
| WO | WO 95/12367 | 5/1995 |
| WO | WO 96/18343 | 6/1996 |
| WO | WO 96/32153 | 10/1996 |
| WO | WO 96/39950 | 12/1996 |
| WO | WO 97/27888 | 8/1997 |
| WO | WO 97/42881 | 11/1997 |
| WO | WO 98/09570 | 3/1998 |
| WO | WO 98/17183 | 4/1998 |
| WO | WO 98/33452 | 8/1998 |
| WO | WO 98/34546 | 8/1998 |
| WO | WO 98/39048 | 9/1998 |
| WO | WO 98/58590 | 12/1998 |
| WO | WO 99/02094 | 1/1999 |
| WO | WO 99/05977 | 2/1999 |
| WO | WO 99/07292 | 2/1999 |
| WO | WO 99/09893 | 3/1999 |
| WO | WO 99/32037 | 7/1999 |
| WO | WO 99/42038 | 8/1999 |
| WO | WO 99/44538 | 9/1999 |
| WO | WO 99/049812 | 10/1999 |
| WO | WO 99/56636 | 11/1999 |
| WO | WO 00/12016 | 3/2000 |
| WO | WO 00/13593 | 3/2000 |
| WO | WO 00/25680 | 5/2000 |
| WO | WO 00/44306 | 8/2000 |
| WO | WO 00/72781 | 12/2000 |
| WO | WO 01/32085 | 5/2001 |
| WO | WO 01/56500 | 8/2001 |
| WO | WO 01/58365 | 8/2001 |
| WO | WO 01/58382 | 8/2001 |
| WO | WO 01/87184 | 11/2001 |
| WO | WO 01/93937 | 12/2001 |
| WO | WO 02/02018 | 1/2002 |
| WO | WO 02/13705 | 2/2002 |
| WO | WO 02/13706 | 2/2002 |
| WO | WO 02/32496 | 4/2002 |
| WO | WO 02/39911 | 5/2002 |
| WO | WO 02/41753 | 5/2002 |
| WO | WO 02/45596 | 6/2002 |
| WO | WO 02/054943 | 7/2002 |
| WO | WO 02/054980 | 7/2002 |
| WO | WO 02/072168 | 9/2002 |
| WO | WO 02/087449 | 11/2002 |
| WO | WO 02/087651 | 11/2002 |
| WO | WO 02/089676 | 11/2002 |
| WO | WO 02/096273 | 12/2002 |
| WO | WO 02/096301 | 12/2002 |
| WO | WO 03/001970 | 1/2003 |
| WO | WO 03/007823 | 1/2003 |
| WO | WO 03/017852 | 3/2003 |
| WO | WO 03/034927 | 5/2003 |
| WO | WO 03/039624 | 5/2003 |
| WO | WO 03/041615 | 5/2003 |
| WO | WO 03/053257 | 7/2003 |
| WO | WO 03/053281 | 7/2003 |
| WO | WO 03/073914 | 9/2003 |
| WO | WO 03/077776 | 9/2003 |
| WO | WO 03/077984 | 9/2003 |
| WO | WO 03/082128 | 10/2003 |
| WO | WO 03/086240 | 10/2003 |
| WO | WO 03/092547 | 11/2003 |
| WO | WO 03/099370 | 12/2003 |
| WO | WO 2004/008974 | 1/2004 |
| WO | WO 2004/014239 | 2/2004 |
| WO | WO 2004/069059 | 8/2004 |
| WO | WO 2004/069538 | 8/2004 |
| WO | WO 2004/073529 | 9/2004 |
| WO | WO-2006/069123 A1 | 6/2006 |
| WO | WO-2007/070797 A2 | 6/2007 |
| WO | WO 2007/121405 | 10/2007 |
| WO | WO 2008/112435 | 9/2008 |
| WO | WO 2008/112436 | 9/2008 |
| WO | WO-2010/009019 | 1/2010 |
| WO | WO 2010/117883 | 10/2010 |
| WO | WO 2010/123821 | 10/2010 |

OTHER PUBLICATIONS

U.S. Appl. No. 13/308,476, filed Nov. 30, 2011.
U.S. Appl. No. 13/685,754, filed Nov. 27, 2012.

* cited by examiner

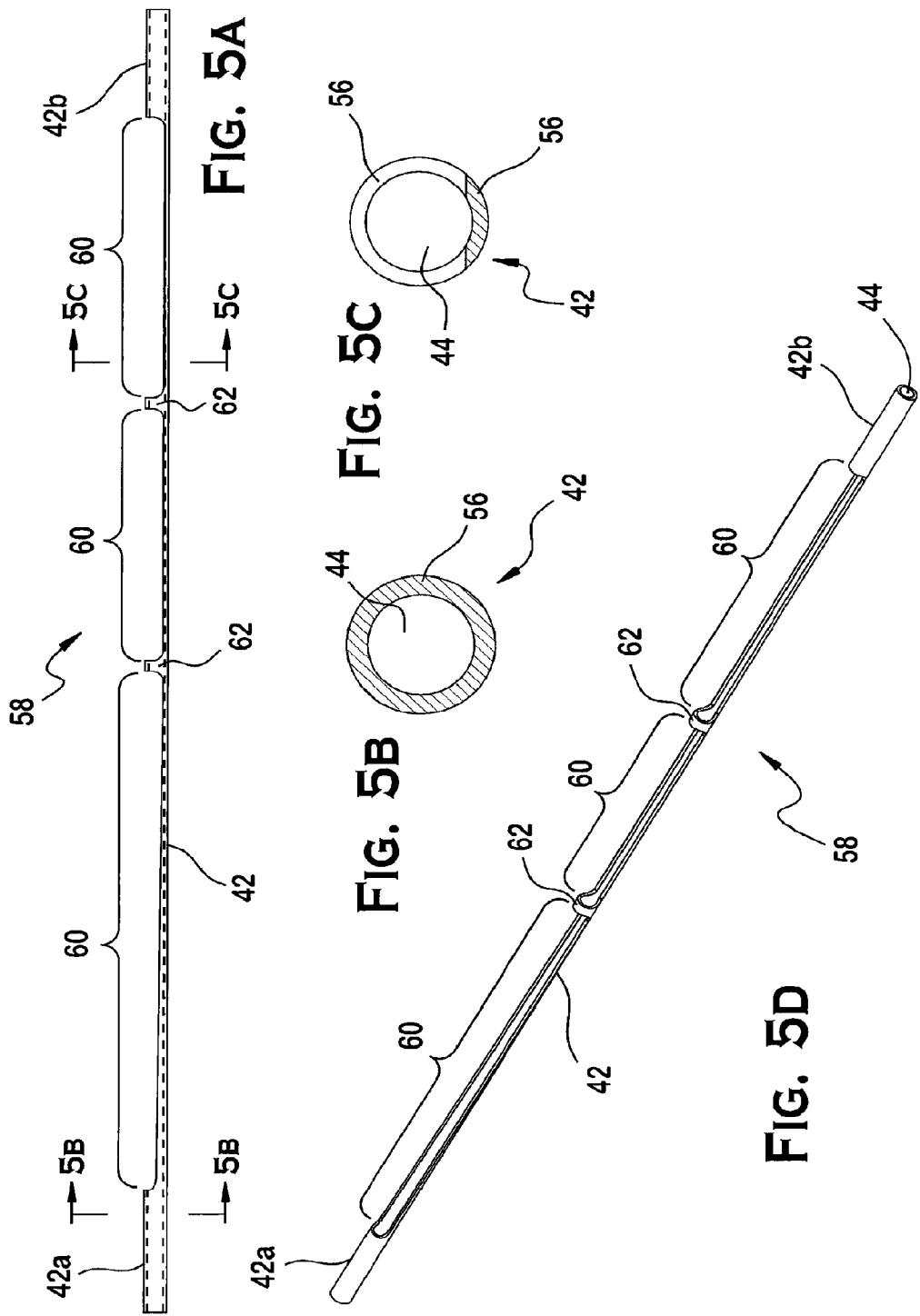

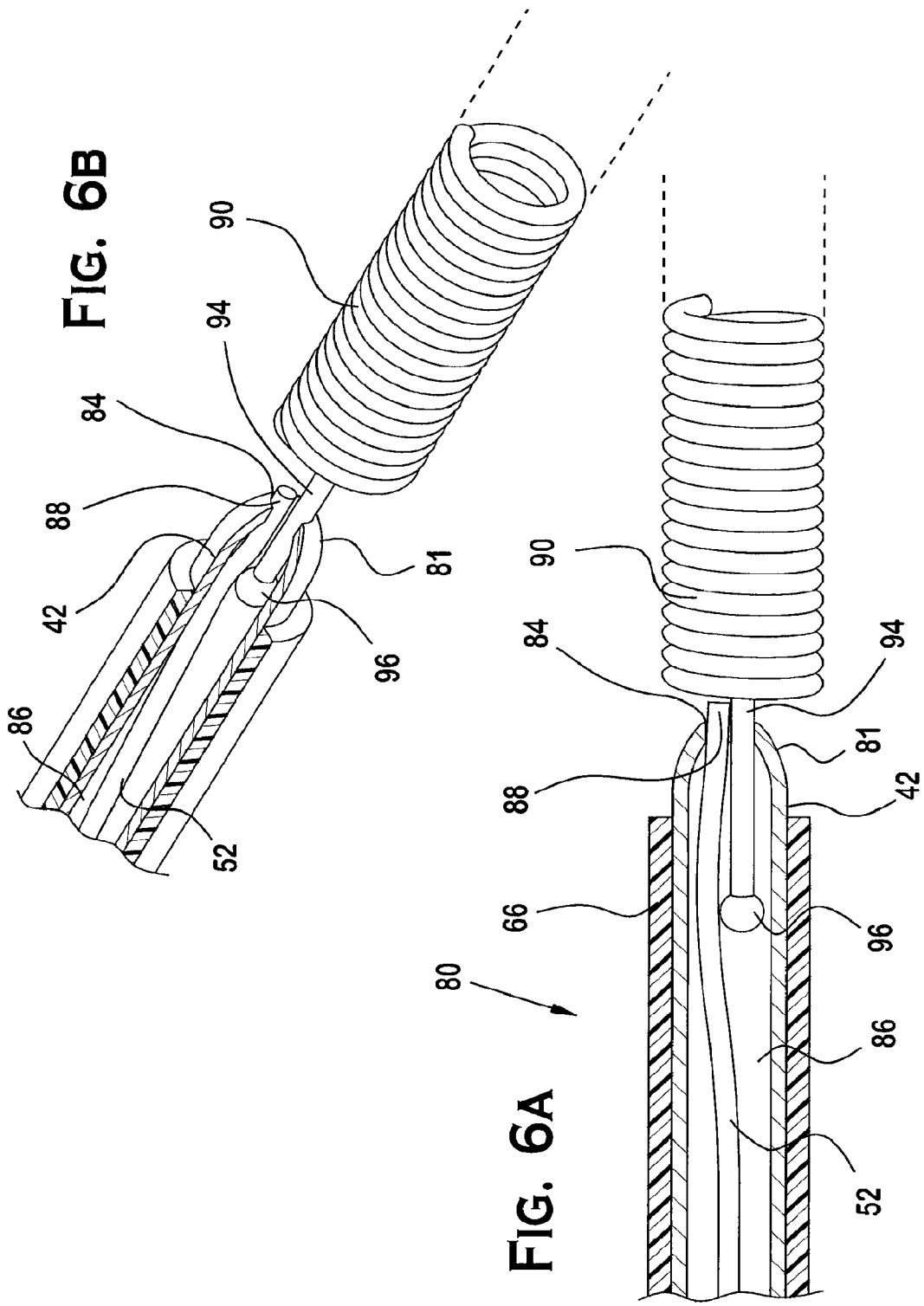

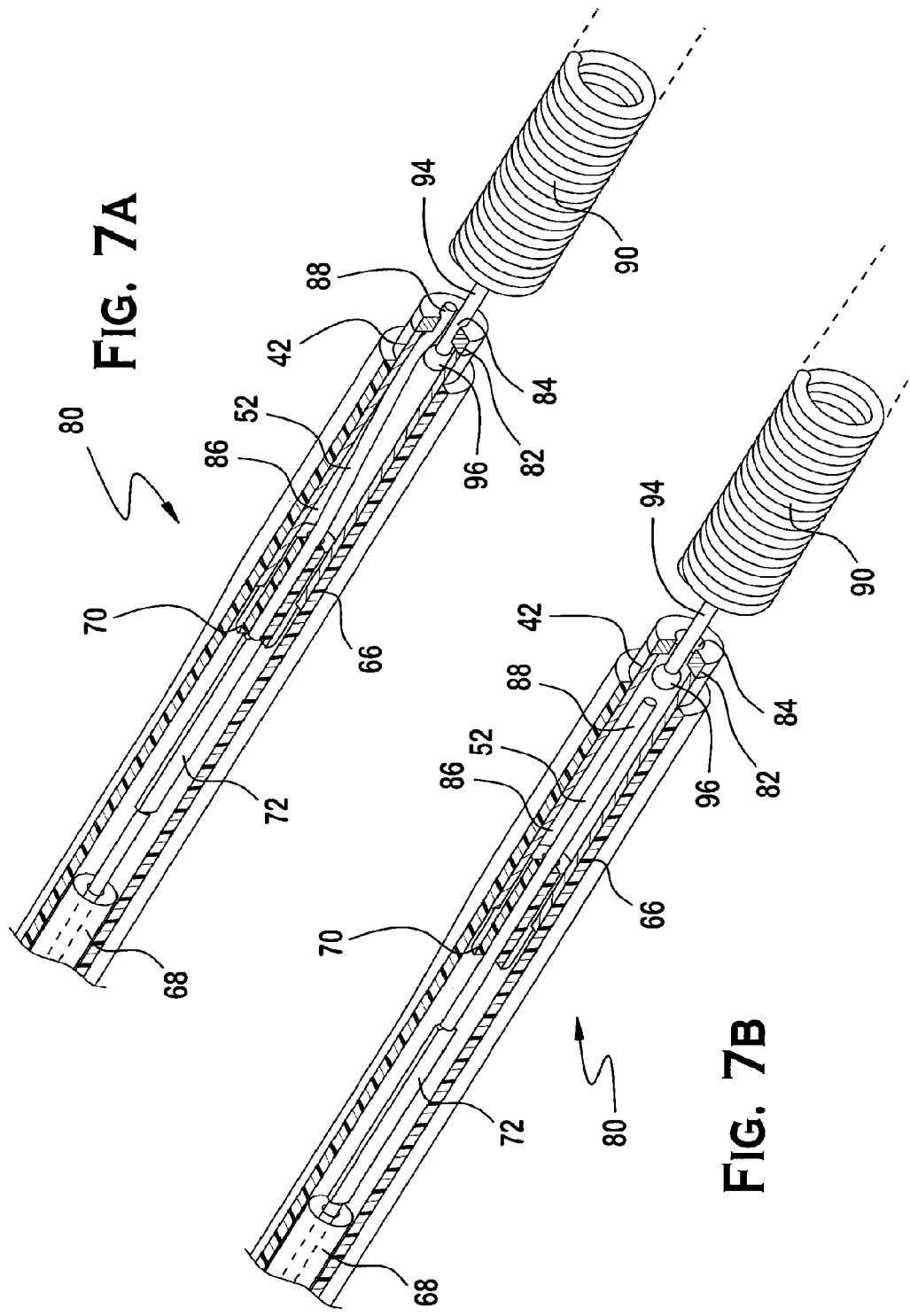

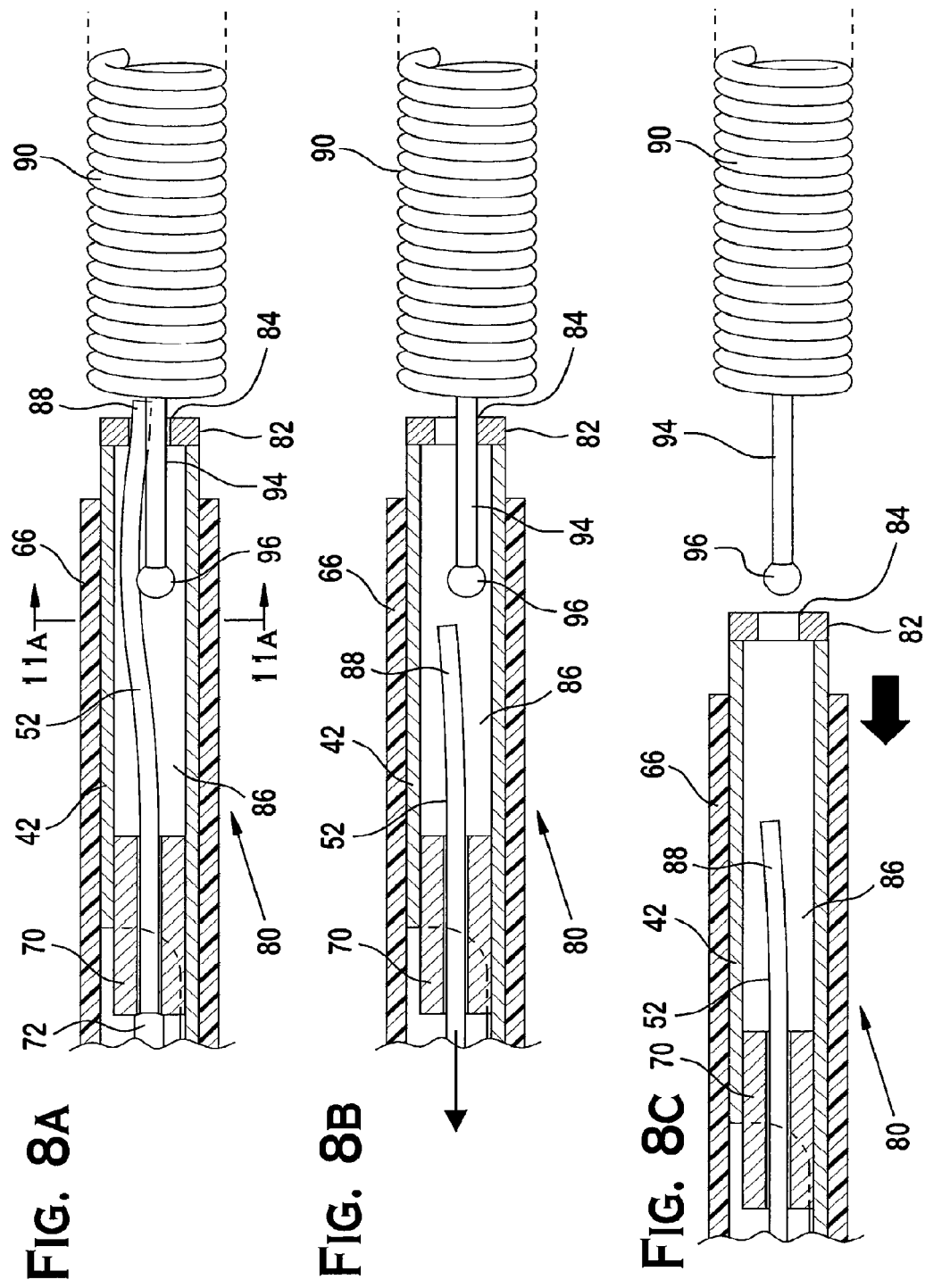

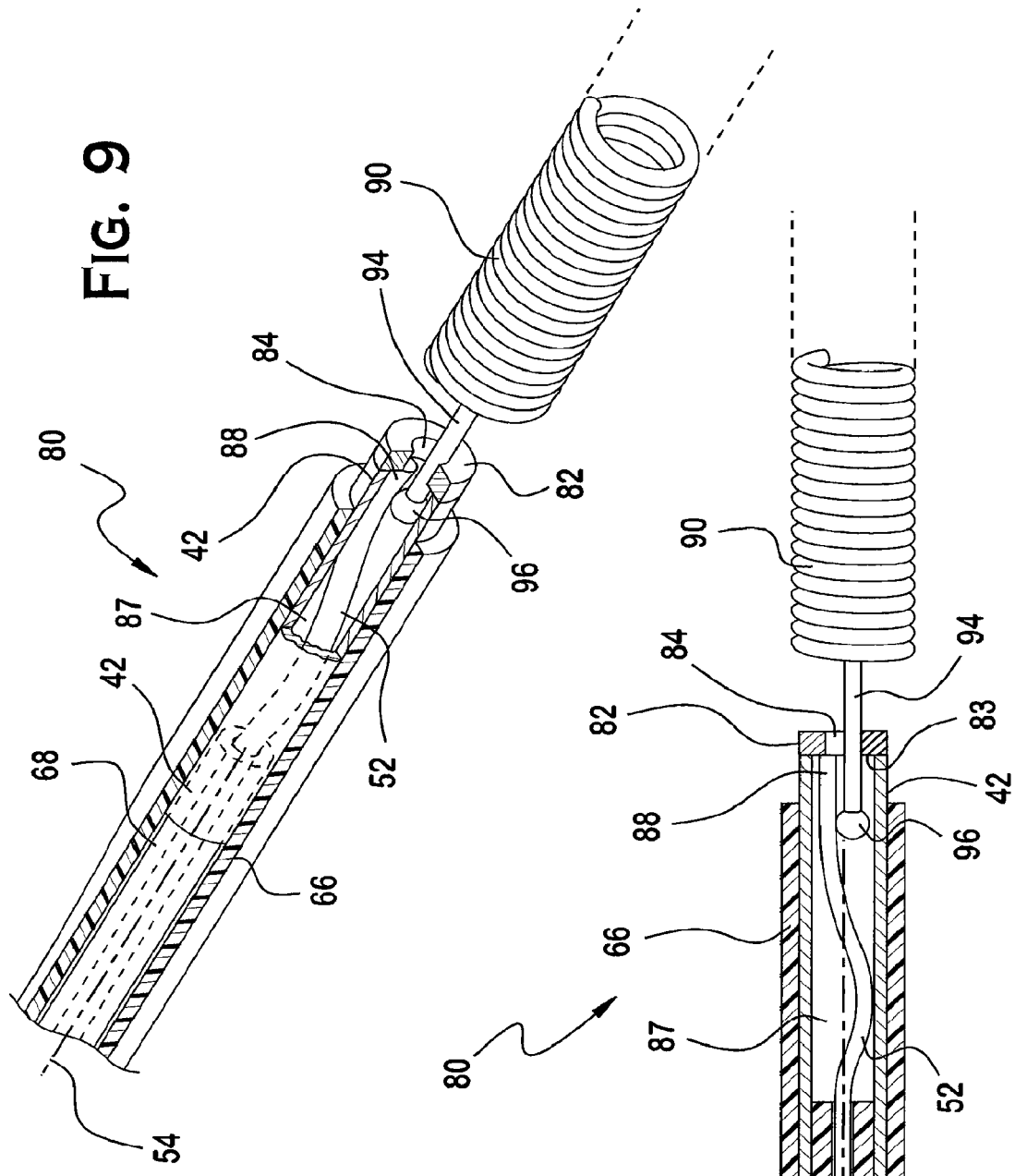

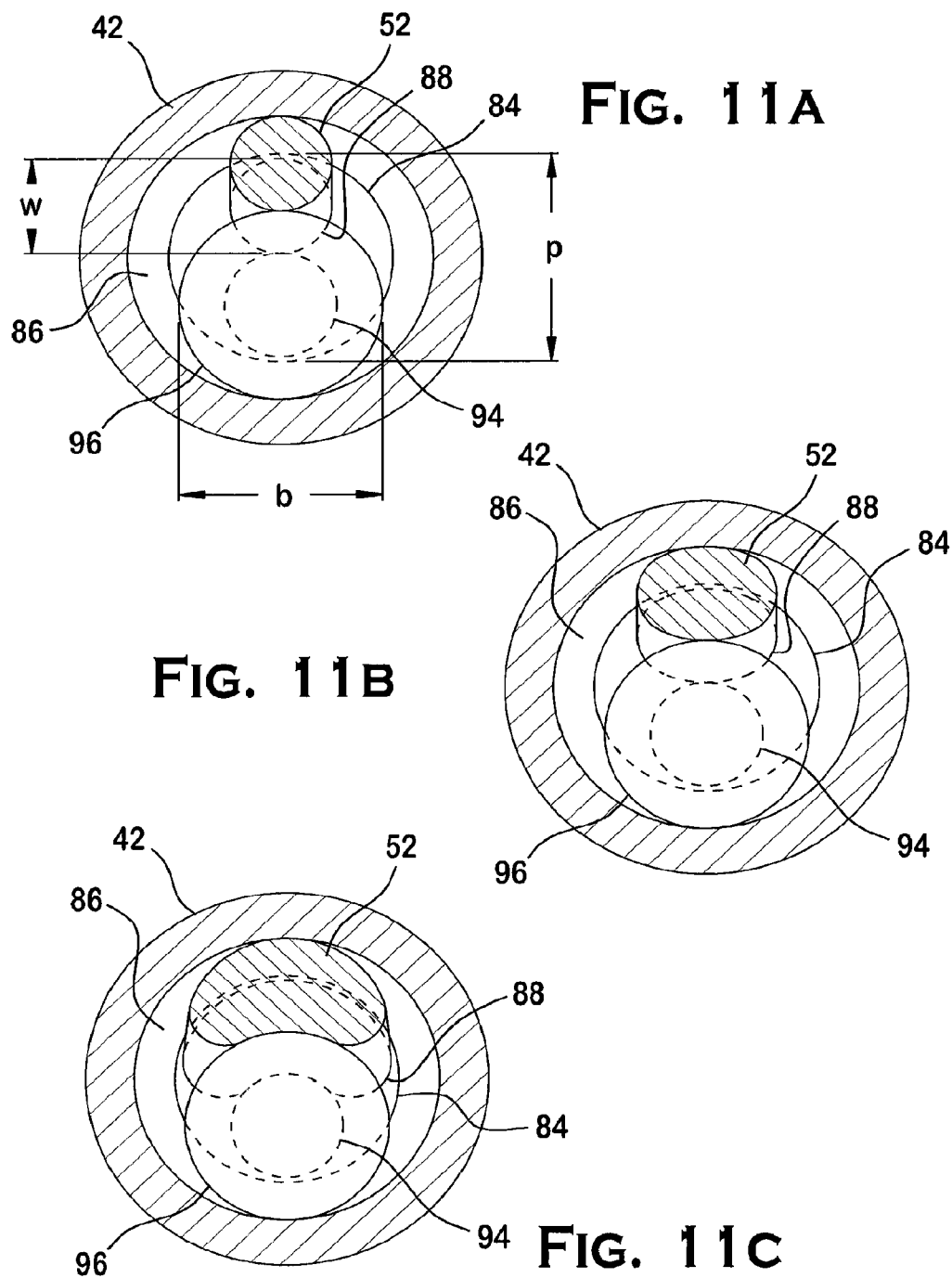

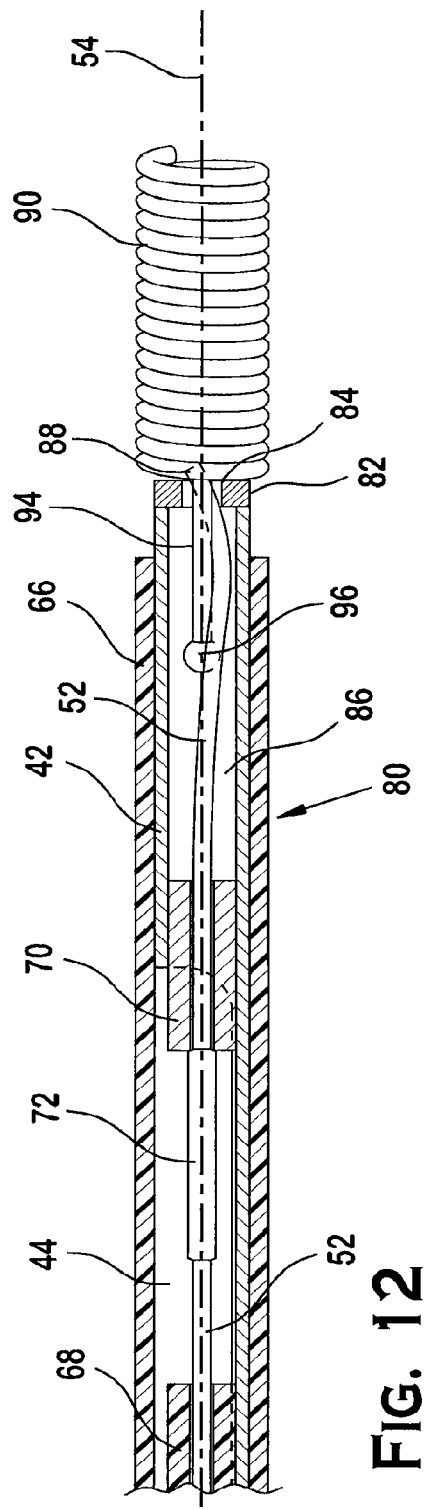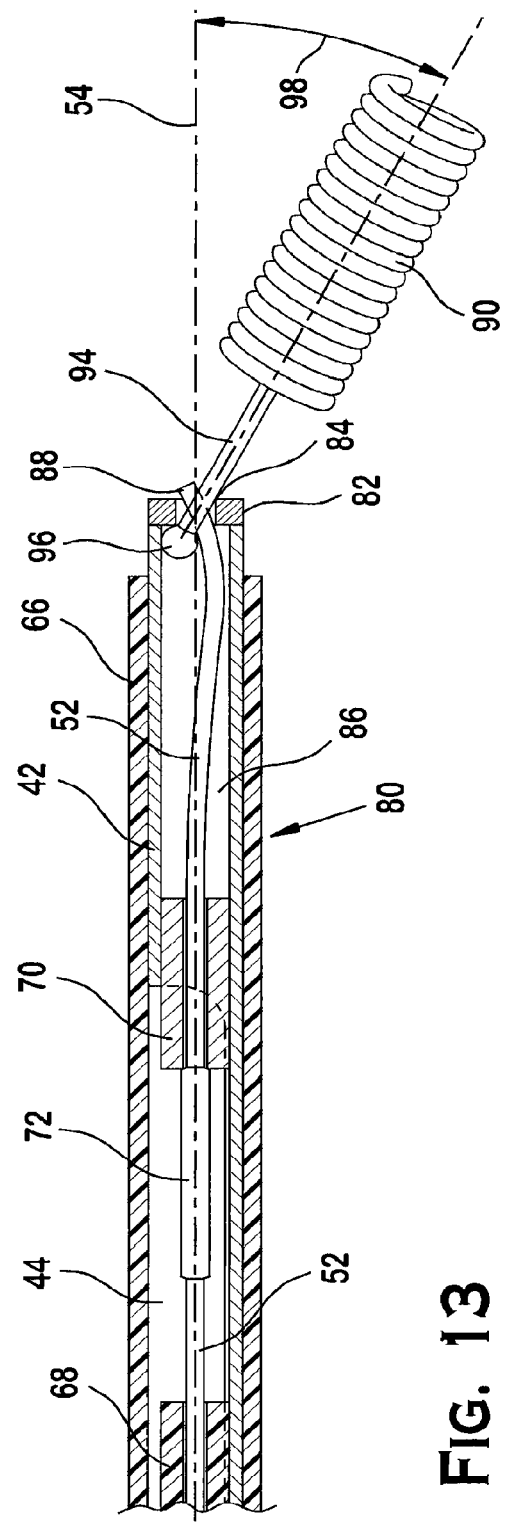
FIG. 12
FIG. 13

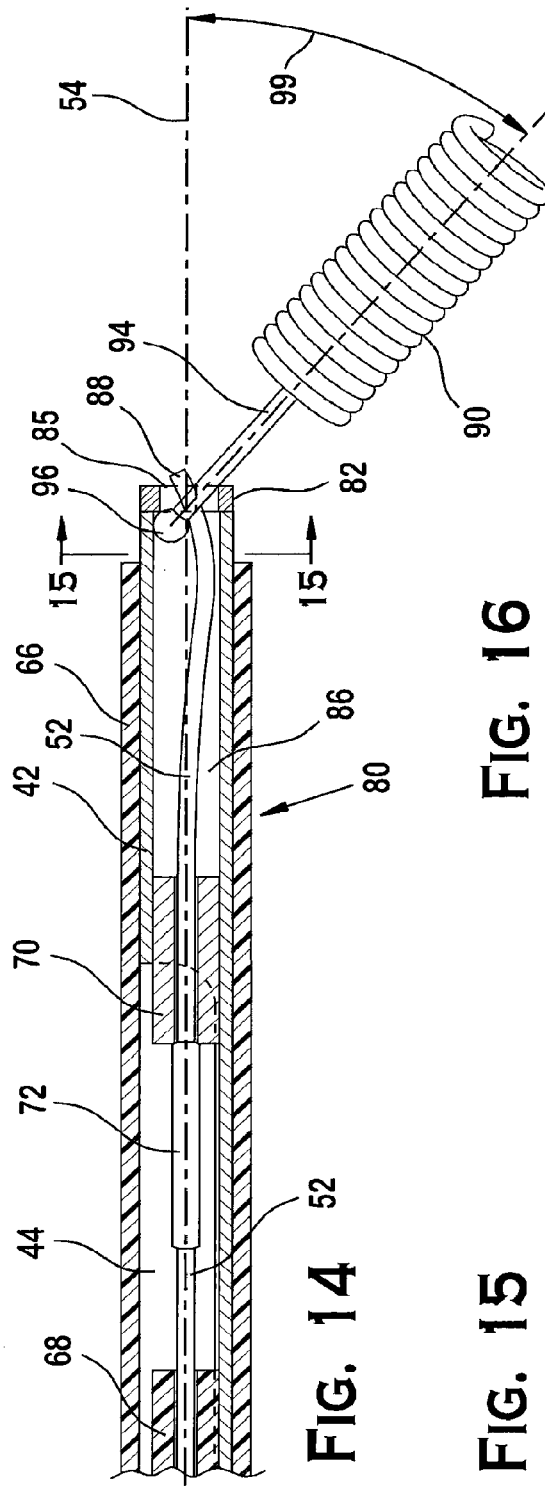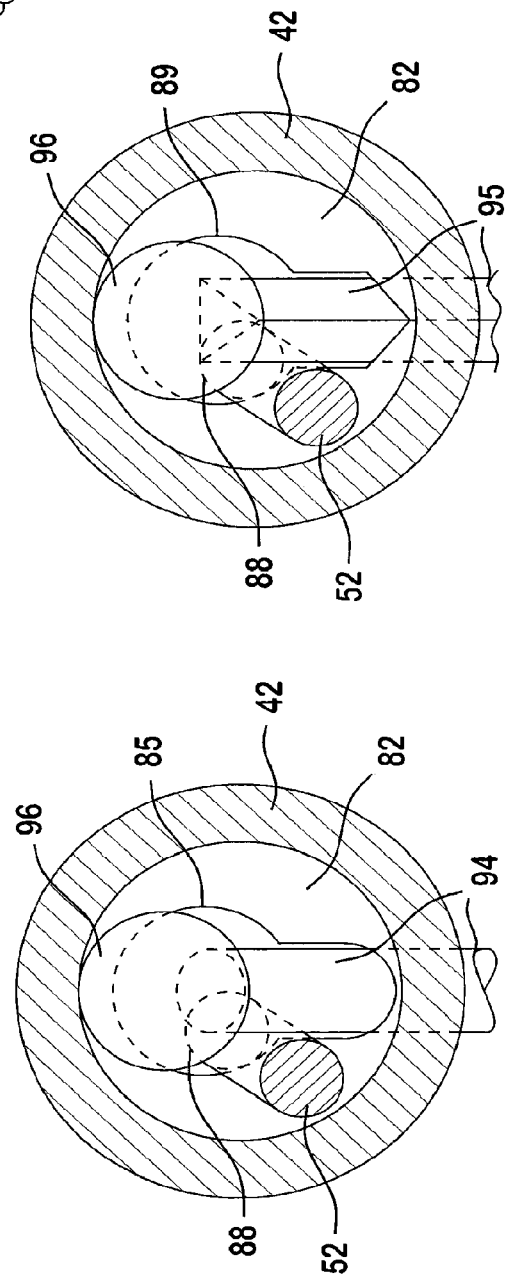

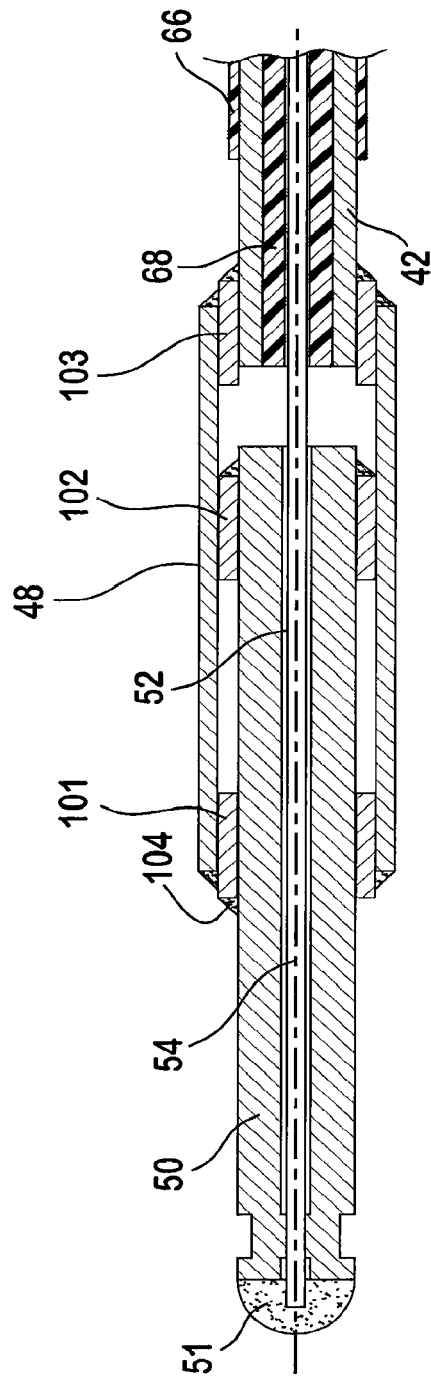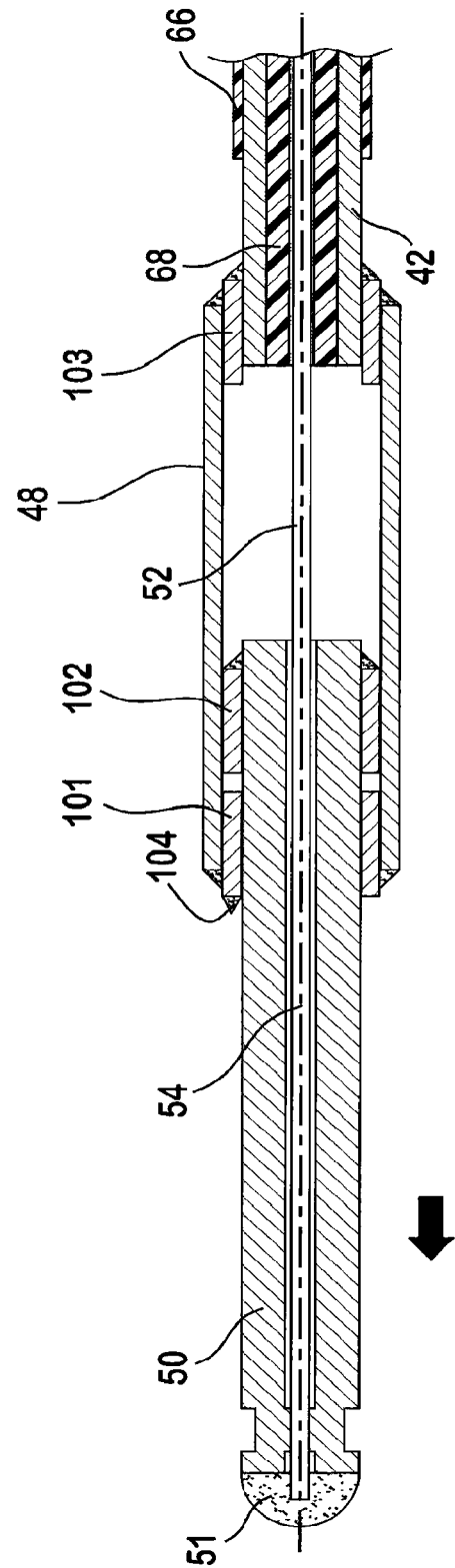
FIG. 20A
FIG. 20B

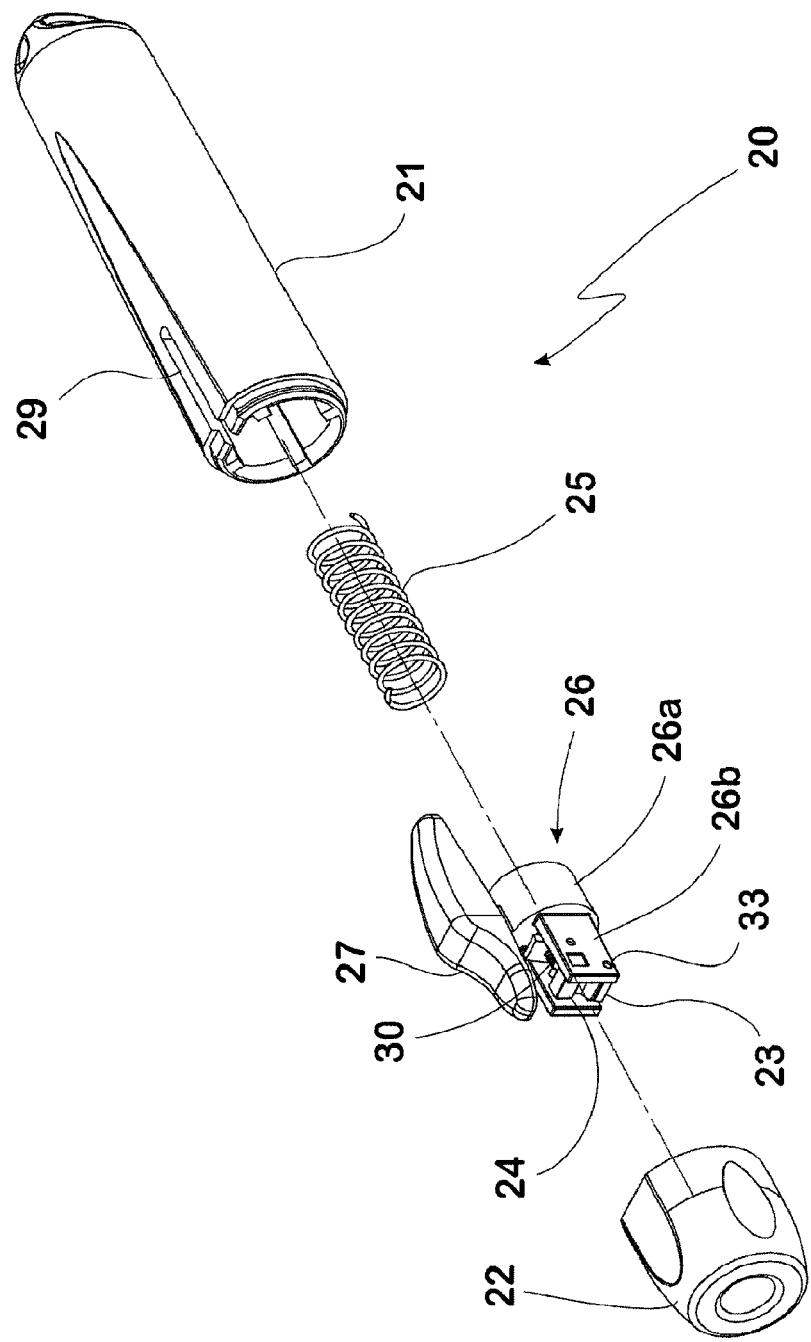

SYSTEM AND METHOD FOR MECHANICALLY POSITIONING INTRAVASCULAR IMPLANTS

PRIORITY DATA AND INCORPORATION BY REFERENCE

This application is a continuation of U.S. patent application Ser. No. 12/297,419, filed Jul. 9, 2009, which is a national stage entry of PCT patent application Ser. No. PCT/US07/66722, filed Apr. 16, 2007, and which claims priority benefit of U.S. Provisional Application Nos. 60/792,414, filed Apr. 17, 2006, and 60/894,589, filed Mar. 13, 2007, each of which are incorporated by reference in their entireties, as if fully set forth herein.

TECHNICAL FIELD

This invention relates to therapeutic implant delivery and retrieval systems and, more particularly, to a system with a member that mechanically engages an implant to be positioned in a body. The positioning includes delivering and deploying an implant at a target site, or removing an implant from the target site. The invention also relates to implants and, more particularly, to implants adapted to be mechanically retained by a delivery and retrieval system.

BACKGROUND ART

Sometimes a body cavity, such as an aneurysm, is located in a surgically remote, delicate, and torturously formed region, such as within the cerebral vasculature, that requires a specialized delivery system to navigate to the region and safely and reliably deliver a coil implant.

U.S. Pat. Nos. 5,122,136 and 5,423,829 describe some existing electrolytic delivery systems having a pusher attached to an implantable platinum coil by detachment segment that can be eroded by an electrolytic process. The coil is advanced by the pusher through a microcatheter to the desired target site within the vasculature and an electrical current is applied to the pusher at the detachment segment. The electrical current causes the electrolytic erosion of the detachment segment that results in the separation of the coil from the pusher and the release of the coil at the target site. It is believed that there are numerous drawbacks and disadvantages to such electrolytic systems. One disadvantage of this design is believed to be that the detachment segment must be positioned distally of microcatheter for release (i.e., the operator cannot "pre-release" the coil within microcatheter if desired). Another disadvantage is believed to be that these systems require electrical insulation and isolation of the detachment segment to reduce the release of metallic particles created during detachment, which may cause unwanted embolization downstream of the target site. Another disadvantage is believed to be that these systems require the practitioner to wait for an unknown amount of time, typically 10-180 seconds, until the implant coil is released, with the release monitored by feedback from a specialized system using complex electrical drivers. Yet another disadvantage is believed to be that these systems generate "false positives" quite often, at a rate of 3-10%, that falsely indicate that the coil has been released when in fact it has not. Further, as with any electrochemical reaction in solution, the system needs to be within ionic fluids to function, and it is believed that undesirable gases are formed at both the anode and the cathode. Additionally, it is believed that there are guide wire and delivery system size limitations because these systems require a constant flow of electrolytes such as saline through the microcatheter to hasten the detachment time of the coil. Because of this need for electrolytes, it is believed that the outer diameter of an electrolytic delivery system is optimized for saline flow rather than for considerations of coil deliverability, pushability, and force transfer of the pusher, and the suppleness of the distal end of the delivery system.

U.S. Pat. Nos. 6,063,100 and 6,607,538 describe hydraulic delivery systems having a pusher attached to an implantable platinum coil with a frictional fit between a pressure cuff on the distal end of the pusher and a cylindrical solid proximal end of the coil. The platinum coil is advanced through a microcatheter by the pusher into the target site. Hydraulic pressure is applied to the proximal end of the pusher, creating hydraulic pressure at the distal end of the pusher and causing the cylindrical solid proximal end of the coil to be pushed out of the pressure cuff to cause the separation of the coil from the pusher. One disadvantage of this design is believed, to be that such systems require complex catheter construction and rigorous purging to avoid the delivery of air emboli. Even after purging, it is believed that some air emboli are usually left in the system and will be inevitably injected into the patient during the detachment process. Another disadvantage is believed to be that these systems are time consuming to use because of the preparation of the pusher and because of the filling and attachment of pressure syringes. These systems are believed to be less reliable than electrolytic systems and at times have either failed to release the coil or prematurely released the coil. Additionally, with this type of design, it is believed that the delivery system is optimally sized for hydraulic detachment, and not sized to facilitate coil delivery or the action of the pusher-coil interface. These delivery systems have generally hollow conduits designed for high hydraulic pressures and, as a result, are rigid. The coil-pusher interface, as well, is stiff because part of the proximal end of the coil is wedged tightly into the distal end of the pusher.

U.S. Pat. No. 5,234,437 describes a mechanical delivery system with a pusher that is attached to an implantable platinum coil by a threaded portion at the distal end of the pusher that screws into the inner winds of the coil. The coil is advanced by the pusher through a microcatheter into the target site. Once positioned, the operator twists the proximal end of the pusher a number of times to unscrew the distal end of the pusher from coil implant. A disadvantage of this design is believed to be that the system will not work well in highly tortuous anatomy due to the diminishing torque transmission of the pusher, that is, the body of the pusher itself twists with little or no rotation of the threaded portion. The unscrewing operation of the pusher is also believed to cause undesirable movement of the entire system that could cause misalignment with the target site and cause the coil to be positioned undesirously within the target vessel. Also, the screw design is believed to require the operator to hyper-extend the pusher beyond the tip of the microcatheter to effect release and is non-retrievable at that point.

U.S. Pat. No. 5,895,391 and U.S. Pat. Publ. No. 2006/0276823 describe mechanical delivery systems. U.S. Pat. No. 5,895,391 describes a mating member attached to a vaso-occlusive member that is held in an opening with an interference wire. The interference wire presses the mating member into an opening through the wall of a holding member. U.S. Pat. Publ. No. 2006/0276823 describes a mechanical interlocking mechanism with engagement member attached to a distal end of a pusher member and that extends through a retaining ring at a proximal end of an embolic device. A detachment member extends through an aperture at the distal end of the engagement member to lock the embolic device onto the pusher member.

Accordingly a need exists for an implant delivery system that is easier to use and more reliable than systems currently on the market and that requires fewer steps and faster detachment.

A further need exists for a technique for treating a vascular defect or lesion with platinum coils without creating metallic or gaseous particulates during the detachment process.

A further need exists for an implant delivery system that has increased reliability measured by fewer false positive detachments and fewer premature detachments.

A further need exists for a coil-to-pusher interface that is less rigid than those of existing systems.

A further need exists for an implant delivery system with superior pushability with a supple distal flexibility profile.

DISCLOSURE OF INVENTION

The positioning system includes an actuator operated by an operator, a positioner engaging the actuator, and an implant interface at the distal end of the positioner that engages a complementary portion of an implant.

The positioner provides the operator the ability to controllably move the implant through a microcatheter or delivery tube and to properly position the implant at a target site. The positioner provides a mechanical system for selectively engaging the implant, while maintaining a narrow profile and sufficient flexibility to navigate the tortuous pathways within the body that are navigated to reach the target site. While providing a small and flexible profile, the positioner has sufficient strength to allow the operator to controllably move the implant through the microcatheter, and the mechanical engagement with the implant remains functional and controllable when subjected to high tortuosity near the target site. The mechanical engagement of the positioner to the implant also maintains the proper orientation of the implant throughout the positioning procedure by allowing the implant to rotate and discharge any torsional threes induced during the movement of the implant to the target site. The positioner also allows the operator to control the movement of the positioner and implant by properly translating the control exerted by the operator into predictable and responsive movements near the target site.

The positioner achieves advantageous performance and overcomes problems believed to be limiting the performance of existing systems by providing a mechanical implant engagement system that permits free rotating movement while retaining the implant, and that provides minimal direct contact with the implant, so as to minimize the build up of torsional forces between the positioner and implant when the implant twists and rotates while moving through the microcatheter. The contact between the positioner and implant is minimized and fully rotatable so that the implant will maintain an acceptable orientation as it progresses to the target site while independently reacting to any forces acting on the implant when navigating the tortuous pathway to the target site. The minimization of contact and torsional forces between the positioner and implant improves the operator's ability to control the positioner, and improves accuracy in the positioning of the implant at the target site. The positioner also achieves advantageous performance by providing a mechanical implant engagement system that is narrow, flexible, and controllable. The positioner provides a narrow profile by employing a mechanical implant engagement system in which the implant moves in an axial direction when engaging or disengaging the positioner, without the need for transverse movement of the implant. The positioner provides improved flexibility by using a support structure that has varying flexibility along its length, with greater flexibility corresponding to more tortuous portions of the pathway to the target site. The positioner provides improved controllability by employing materials and surfaces that provide coefficients of friction selected with regard to the tortuosity of the pathway to the target site, and that are utilized in the positioner so as to correspond to the most tortuous portions of the pathway to the target site. The positioner also provides improved control by more fully and accurately communicating the control movements exerted by the operator to the movement of the positioner at the target site. The positioner also provides a system that permits the mechanical engagement or disengagement of the implant without the use of hydraulic, thermal, electrical, or chemical energy.

The implant interface allows the operator to mechanically control the engagement and disengagement of the implant to the positioner, and allows the positioner to retain the implant in a way that minimally contacts the implant, that permits movement in all directions of motion and rotationally, and that allows the implant to move axially and without radial movement when engaging and disengaging the implant interface. The implant interface provides mechanical control of the engagement and disengagement of the implant by retaining a member engaging the implant. The member is introduced into the implant interface through an opening in the positioning system, and retained at the implant interface by obstructing the opening at least in part, or fully, so as to physically prevent the complete exit of the member back through the opening. The obstructing is achieved with a movable elongate member disposed along the length of the positioning system with a distal end that obstructs the opening. By obstructing the opening and not fixedly restraining the implant, the implant remains free to move according to the limitations defined by the implant interface, which includes movement in the axial and radial directions compared to the axis of the positioning system, rotational movement about an axis of the implant, and angular movement that disposes the implant at an angle as compared to the axis of the positioning system. Furthermore, by obstructing the opening and not directly restraining the implant, the contact between the implant interface and the implant is minimized.

The therapeutic implant can be any implant that can be retained and positioned by the positioning system. The implant is retained by the implant interface with an extension engaging the implant. The extension can be a part of the implant when the implant is made, a modified portion of the manufactured implant, or attached to the implant after initial manufacturing. The extension provides an end that is disposed at a distance from the implant body, and allows the implant interface to engage and secure the implant by securing the end of the extension. The implant body itself, however, is not connected to the implant interface. The end of the extension is preferably a ball, but can take other forms.

The positioning system facilitates the unhindered rotation of the ball and implant, thereby avoiding the sudden or uncontrolled release of energy imparted to the system by the movement of the system to the target site. The free rotation of the implant and ball allows the implant to be deployed from the microcatheter at the target site much more gently than with existing systems having a connection that is rigid or that partly or wholly limits movement and rotation between the implant and delivery system, and the free rotation also lowers the force applied to the vasculature during deployment and positioning of the implant at the target site.

The implant interface also advantageously provides for the unrestrained axial movement of the ball within a cavity of the implant interface. The movement of the ball within the cavity is related to the longitudinal length of the cavity and the length of the rod engaging the implant and disposed in the cavity. When the implant and positioner are both advanced in the distal direction, friction against the surface of the implant will cause the ball to move axially to an extreme proximal position in the cavity and the proximal surface of the implant will abut the distal surface of positioner. When the positioner is advanced in the proximal direction, friction against the surface of the implant will cause the ball to move distally to an extreme distal position in the cavity, and that there will be minimal or no frictional contact between the positioner and implant. The differing frictional characteristics related to the axial movement of the ball in the cavity, and the deuce of contact between implant and the implant interface, provides a "friction push" and a "frictionless pull" to the positioning system that is appealing to the operator because it provides an additional tactile sensation related to the movement of the system.

The axial movement of the ball in the cavity advantageously permits the implant to assume an angled orientation compared to the axis of the positioner, and articulate or pivot around the ball. That angled orientation and articulation advantageously assists in the relaxation and discharge of potential energy or spring forces in the implant, or between the implant and the positioner, as the implant is moved through the microcatheter.

The positioner also advantageously captures or recaptures an implant already located at or proximate the target site.

The actuator interface provides the operator the ability to control the movement of the implant as it is positioned by the positioning system, and to mechanically control the selective engagement and disengagement of the implant and implant interface. The actuator interface controls the movement of the implant by providing a surface upon which the operator can exert control, so that the controlling motions of the operator are accurately transferred to the implant interface and implant through the positioner. The actuator interface provides a relatively stiff proximal end of the positioner that transfers the axially-directed and rotational forces exerted on the actuator interface by the operator to the relatively flexibly distal end of the positioning system with minimal loss due to flexing and twisting of the positioning system. The actuator interface provides control of the engagement and disengagement of the implant from the implant interface with a sliding mechanism that controllably and predictably moves the implant interface between the engaged and disengaged orientations. The actuator interface also connects to an actuator that permits the operator to controllably and predictably move the slider. In addition, the actuator interface establishes and maintains a compressive biasing of the implant interface so that the implant interface remains in the engaged orientation by disposing the slider in a distally forward position.

The actuator provides a mechanism that removably engages the actuator interface and causes the controllable and predictable movement of the actuator interface. The actuator achieves this function by providing a structure that holds the outer tube in a fixed position relative to the body of the actuator, and a pawl and anvil that pinches the slider and pulls the slider in the proximal direction for a predetermined distance with a predetermined force, and then disengages from the slider to allow disengagement from the actuator. The actuator also provides a design that allows the operator to hold the actuator firmly in place, in order to maintain the position of the positioner relative to the target site, and allows the operator to utilize the actuator in a controlled manner that minimizes the movement of the positioner.

In order to minimize the force required from the operator, and to lessen the potential for failure of instrument components, the positioning system advantageously achieves improved pushability. The force applied to the proximal end of the positioner translates to an equal or near equal force at the distal end of the positioner. The positioning system also advantageously achieves improved pushability by reducing friction between the cord and the positioner, and between the positioner and the microcatheter. Advantageous force transfer ratio is achieved by reducing the average friction coefficient at the portions of the positioning system subject to the greatest tortuosity. This is achieved by preferably selecting specific materials and surface characteristics of mating surfaces at the portions of the positioning system subject to the greatest tortuosity.

The positioning system achieves the appropriate level of flexibility by preferably providing a relatively rigid structure at the proximal portion of the positioner, a relatively supple structure at the distal portion the positioner, and a transition region in the middle of the positioner that provides a change in flexibility between the proximal and distal portions. The proximal portion of the positioner preferably provides a flexibility (or stiffness) that remains almost constant along the length of this section of the positioner. The near-constant flexibility of the proximal portion is achieved by the use of a tube structure. The distal portion and the transition region achieve a suppleness with a combination of structural modifications to the tube structure that increases flexibility, the increase in the degree of those structural modifications along the length of the tube structure in the distal direction, and the structural support provided to the positioner by reinforcing structures. The flexibility of the distal portion increases along the length of this section, with the greatest suppleness achieved near or at the distal-most end of the positioner. The near-constant flexibility of the proximal portion is also achieved by a fully-enclosed tube structure of the positioner without the use of skiving. The variable flexibility characteristics of the distal portion and the transition region are achieved by a combination of a tube with skiving, the increase in the degree of the skiving along the length of the tube in the distal direction, and the structural support provided to the positioner by the positioner tube sleeve.

The positioning system achieves a mechanically-operated implant engagement and disengagement system with an appropriate profile, or size, by utilizing materials and surfaces with variable friction coefficients, strengths, and flexibilities appropriate for a positioner subjected to a tortuous pathway. The outer diameter of the distal end of the positioner is small enough to reach the target site while permitting the proper operation of the implant interface from a mechanical system connecting the implant interface to the proximal end of the positioning system.

The positioner avoids or minimizes the development of fatigue-related stresses at the interface between the positioner and implant by permitting the unrestrained movement of the implant relative to the positioner, within the limitations defined by the implant interface. The development of implant interface stresses is minimized or avoided because the ball, rod, and implant are able to move in the axial and radial directions compared to the axis of the positioning system, to rotate about an axis of the rod or implant, and to move angularly so that implant is at an angle as compared to the axis of the positioning system.

The positioning system does not require an additional step of preparing a coil detachment mechanism because the positioner and implant are already in an engaged orientation when removed from packaging and prior to insertion into a patient. The positioner and implant thus provide a system that is ready for use out of the package. The positioning system also provides a direct connection between the actuation of a detachment mechanism and the detachment of the implant from the delivery system, without an intermediary process that must initiate and complete to achieve coil detachment. The positioning system thus achieves a fast preparatory and/or detachment time, which represents a short period of time between the opening of the packaging and the deployment of the implant. The positioning system can be prepared for use without delays relating to the preparation of the coil detachment mechanism, and can achieve detachment of the implant from the positioning system without delays resulting from an intermediate process that must be initiated and completed to achieve the detachment. The absence of such delays, and the connection of the detachment mechanism, provides a system that permits a fast and efficient deployment of implants at a target site. The reduction in the length of time required to prepare the positioning system advantageously increases the efficiency of the procedure because a coil detachment mechanism preparation step is not needed, thereby allowing the practitioner to attend to other duties during the invasive medical procedure. The reduced deployment time advantageously allows the length of the invasive medical procedure to be shortened because time is not needed for the detachment mechanism to achieve coil detachment. The short deployment time also allows the expended positioner to be removed soon after detachment and allow the next implant to be inserted and positioned in a given time interval.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 5A is a plan view of the positioner tube of the embodiment of FIG. 3.

FIG. 5B is a cross-sectional view of a portion of FIG. 5A.

FIG. 5C is a cross-sectional view of another portion of FIG. 5A.

FIG. 5D is an isometric view of the positioner tube of FIG. 5A.

FIG. 6A is a plan cross-sectional view of the implant interface of another embodiment, and a plan view of a portion of an exemplary implant.

FIG. 6B is an isometric view of the implant interface of FIG. 6A, with the implant interface shown in partial quarter section.

FIG. 7A is an isometric view of portions of the positioner and implant of FIG. 3, with the positioner in an engaged orientation, and with the positioner shown in partial quarter section.

FIG. 7B is an isometric view of portions of the positioner and implant of FIG. 3, with the positioner in a disengaged orientation, and with the positioner shown in partial quarter section.

FIG. 8A is a plan cross-sectional view of the positioner and a plan view of the implant of FIG. 7A.

FIG. 8B is a plan cross-sectional view of the positioner and a plan view of the implant of FIG. 7B.

FIG. 8C is a plan cross-sectional view of portions of the positioner and implant of FIG. 3, with the implant removed from the positioner.

FIG. 9 is an isometric view of the implant interface of yet another embodiment, and partial isometric view of an exemplary implant.

FIG. 10 is a plan cross-sectional view of the implant interface and partial plan view of the implant of FIG. 9.

FIG. 11A is a cross-section view of the implant interface from FIG. 8A.

FIG. 11B is an alternative implant interface to the embodiment illustrated in FIG. 11A.

FIG. 11C is another alternative implant interface to the embodiment illustrated in FIG. 11A.

FIG. 12 is a plan cross-sectional view of a portion of the embodiment of FIG. 3 in one orientation.

FIG. 13 is a plan cross-sectional view of a portion of the embodiment of FIG. 3 in another orientation.

FIG. 14 is a plan cross-sectional view of an alternative embodiment to the positioner of FIG. 3, and a plan view of the implant of FIG. 3.

FIG. 15 is a cross-section view from FIG. 14.

FIG. 16 is a cross-section view of an alternative to the embodiment illustrated in FIG. 15.

FIG. 20A is a plan cross-section view of still another embodiment of the actuator interface of FIG. 3 in a first orientation.

FIG. 20B is a plan cross-section view of still another embodiment of the actuator interface of FIG. 3 in a second orientation.

FIG. 28 is an isometric partially-exploded view of the actuator of FIG. 27.

MODE(S) FOR CARRYING OUT THE INVENTION

Figure 1A:
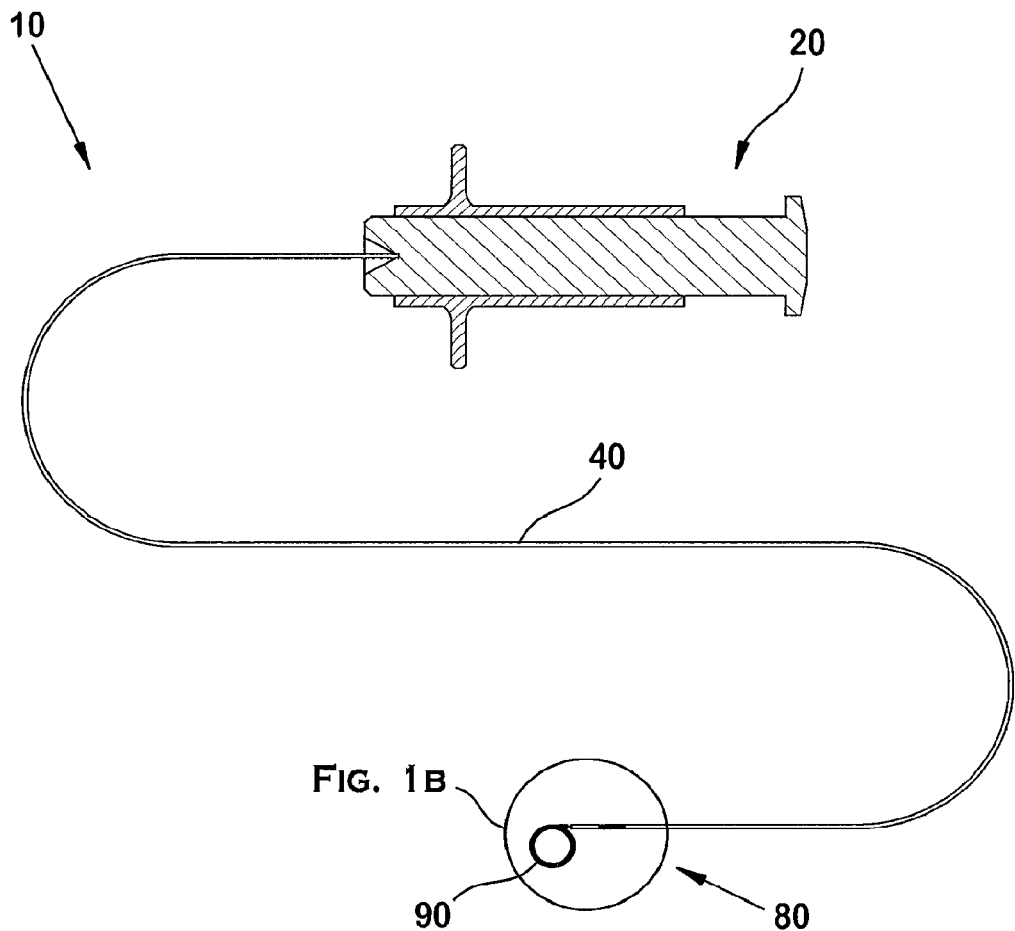
FIG. 1A is a plan view of the positioning system, and a plan view of an exemplary implant.
Figure 1B:
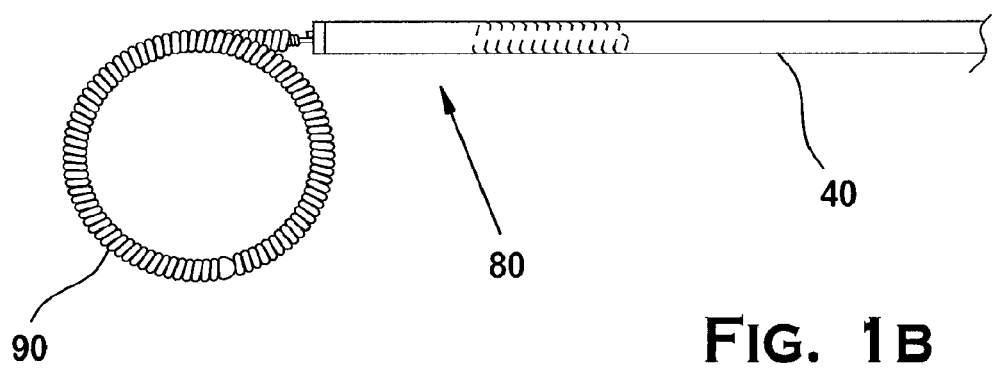
FIG. 1B is a closer view of a portion of FIG. 1A.

As illustrated in FIGS. 1A and 1B, the positioning system 10 preferably includes an actuator 20 operated by an operator, a positioner 40 engaging the actuator 20, and an implant interface 80 at the distal end of the positioner 40. A portion of the implant interface 80 engages a complementary portion of an implant 90.

Figure 2A:
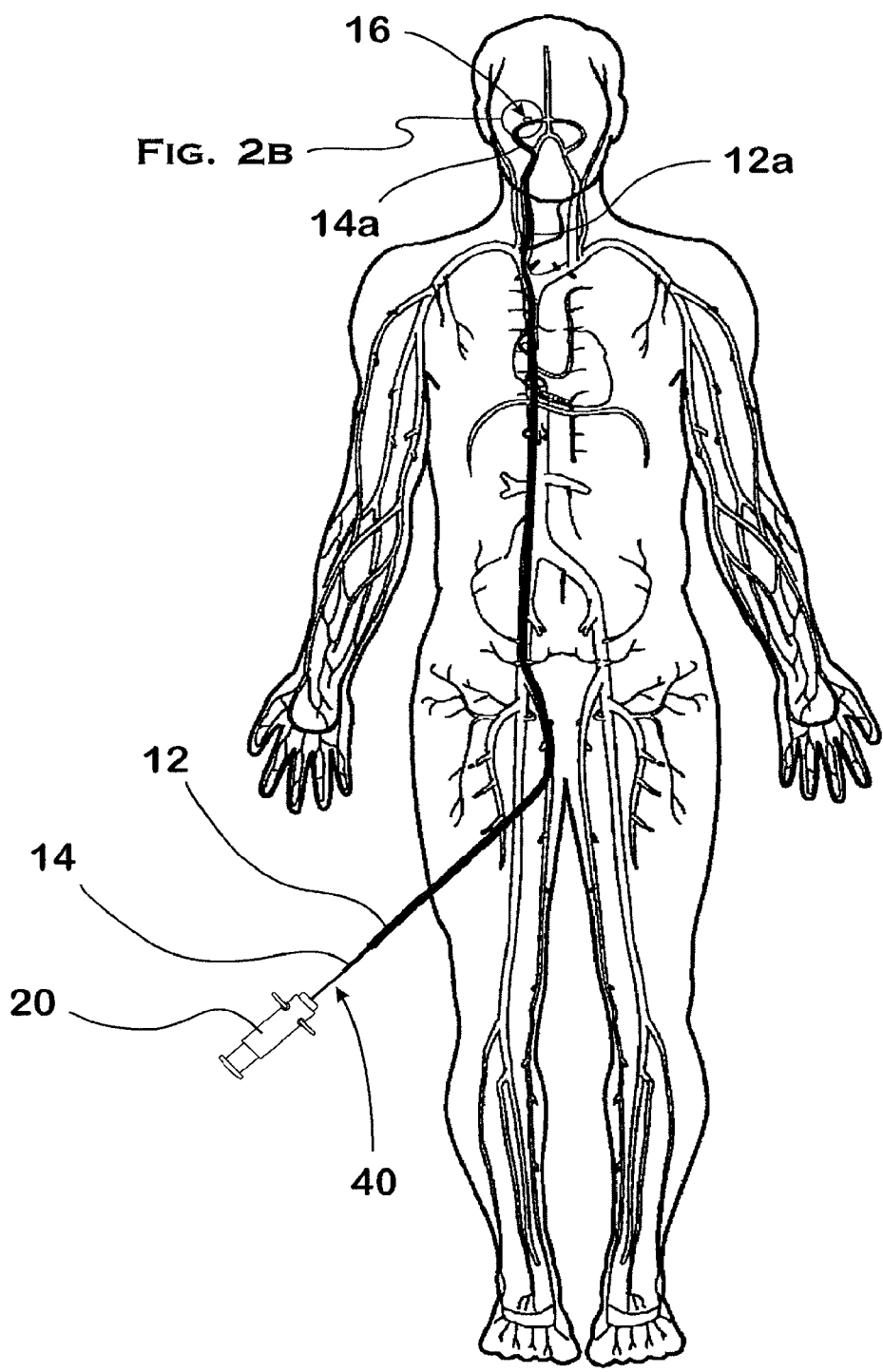
FIG. 2A is a plan view of the positioning system of FIG. 1A within the human body.
Figure 2B:
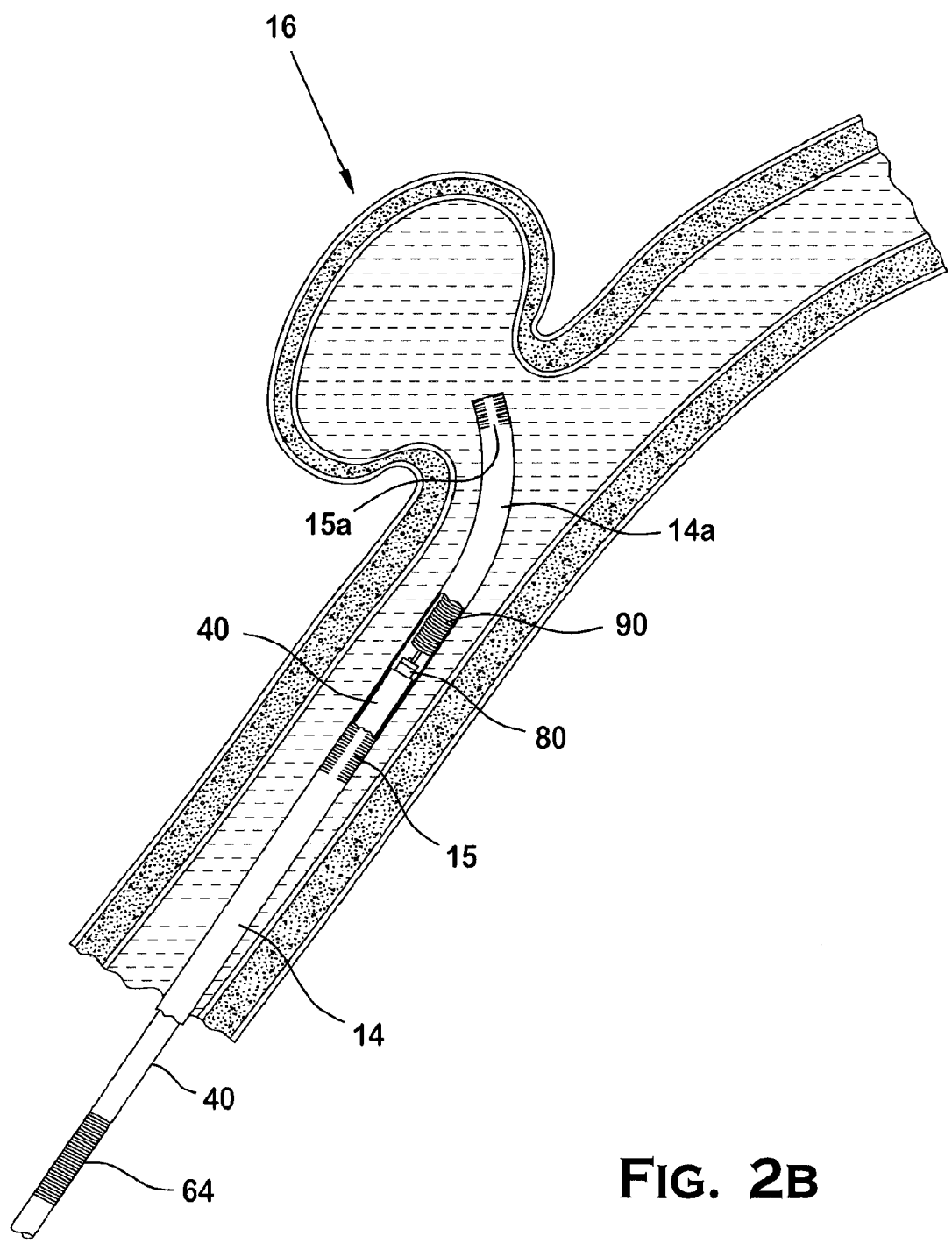
FIG. 2B is a closer view of a portion of FIG. 2A showing the positioning system in partial cross-section and an exemplary implant in a position within the human body.
Figure 2C:
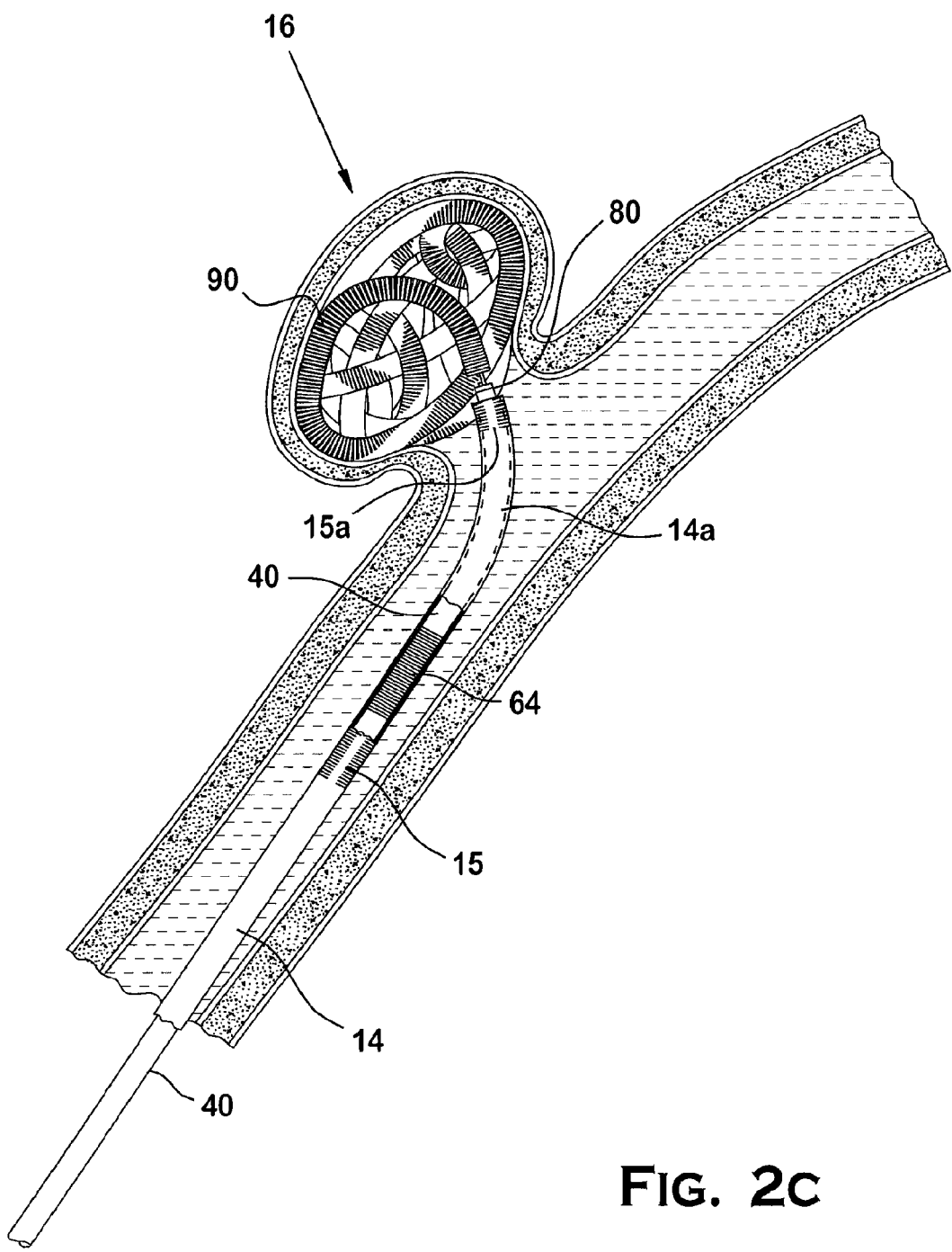
FIG. 2C is a closer view of a portion of FIG. 2A showing the positioning system in partial cross-section and an exemplary implant in another position within the human body.

In the embodiment illustrated in FIGS. 1A and 1B, an operator uses a guide tube or guide catheter 12 to position a delivery tube or microcatheter 14 in a patient's vasculature, as illustrated in FIG. 2A. The procedure involves inserting the guide catheter 12 into the patient's vasculature through an access point such as the groin, and directing the distal end 12a of the guide catheter 12 through the vascular system until it reaches the carotid artery. After removing a guide wire (not shown) from the guide catheter 12, a microcatheter 14 is inserted into the guide catheter 12 and the distal end 14a of the microcatheter 14 subsequently exits the guide catheter distal end 12a and is positioned near the target site 16, such as an aneurysm in the patient's brain. As illustrated in FIGS. 2B and 2C, the microcatheter 14 includes microcatheter markers 15 and 15a that facilitate imaging of the distal end 14a of the microcatheter 14 with common imaging systems and, in the illustrated embodiment, the microcatheter markers 15 and 15a are made of a radiopaque material. After the distal end 14a reaches the target site 16, the positioning system 10 of the illustrated embodiment is then inserted into the microcatheter 14 to position the implant interface 80 at the distal end of the positioner 40 near the target site 16, as illustrated in FIG. 2C. If the implant 90 is being delivered in the procedure, the implant 90 is attached to the implant interface 80 prior to inserting the positioning system 10 into the microcatheter 14. This mode of implant delivery is illustrated in FIGS. 2A-2C. The delivery of the implant 90 is facilitated by disposing the microcatheter marker 15a near the target site 16, and aligning the microcatheter marker 15 with a positioner marker 64 in the positioner 40 which, when the two markers (markers 15 and 64) are aligned with each other as illustrated in FIG. 2C, indicates to the operator that the implant interface 80 is in the proper position for the release of the implant 90 from the positioning system 10. After depositing the implant 90 at the target site 16, a second implant 90 can be deposited at the target site 16 by removing the positioning system 10 from the microcatheter 14 and inserting a second positioning system 10 with an attached second implant 90 into the microcatheter 14 in a manner similar to the method used with the insertion of the first implant 90. The same procedure can be used for a third implant 90 and subsequent implants if clinically necessary. If the implant 90 is already in the patient's body to be retrieved or repositioned, the positioning system 10 is inserted into the microcatheter 14 without the implant 90.

Positioner

The positioner provides the operator the ability to controllably move the implant through the microcatheter and to properly position the implant at the target site. The positioner provides a mechanical system for selectively engaging the implant, while maintaining a narrow profile and sufficient flexibility to navigate the tortuous pathways within the body to reach the target site. While providing a small and flexible profile, the positioner has sufficient strength to allow the operator to controllably move the implant through the microcatheter, and the mechanical engagement with the implant remains functional and controllable when subjected to high tortuosity near the target site. The mechanical engagement of the positioner to the implant also maintains the proper orientation of the implant throughout the positioning procedure by allowing the implant to rotate and discharge any torsional forces induced during the movement, of the implant to the target site. The positioner also allows the operator to control the movement of the positioner and implant by properly translating the control exerted by the operator into predictable and responsive movements near the target site.

The positioner achieves advantageous performance and overcomes problems believed to be limiting the performance of existing systems by providing a mechanical implant engagement system that permits free rotating movement while retaining the implant, and that provides minimal direct contact with the implant, so as to minimize the build up of torsional forces between the positioner and implant when the implant twists and rotates while moving through the microcatheter. The contact between the positioner and implant is minimized and fully rotatable so that the implant will maintain an acceptable orientation as it progresses to the target site while independently reacting to any forces acting on the implant when navigating the tortuous pathway to the target site. The minimization of contact and torsional forces between the positioner and implant improves the operator's ability to control the positioner, and improves accuracy in the positioning of the implant at the target site. The positioner also achieves advantageous performance by providing a mechanical implant engagement system that is narrow, flexible, and controllable. The positioner provides a narrow profile by employing a mechanical implant engagement system in which the implant moves in an axial direction when engaging or disengaging the positioner, without the need for transverse movement of the implant. The positioner provides improved flexibility by using a support structure that has varying flexibility along its length, with greater flexibility corresponding to more tortuous portions of the pathway to the target site. The positioner provides improved controllability by employing materials and surfaces that provide coefficients of friction selected with regard to the tortuosity of the pathway to the target site, and that are utilized in the positioner so as to correspond to the most tortuous portions of the pathway to the target site. The positioner also provides improved control by more fully and accurately communicating the control movements exerted by the operator to the movement of the positioner at the target site. The positioner also provides a system that permits the mechanical engagement or disengagement of the implant without the use of hydraulic, thermal, electrical, or chemical energy.

Figure 3:
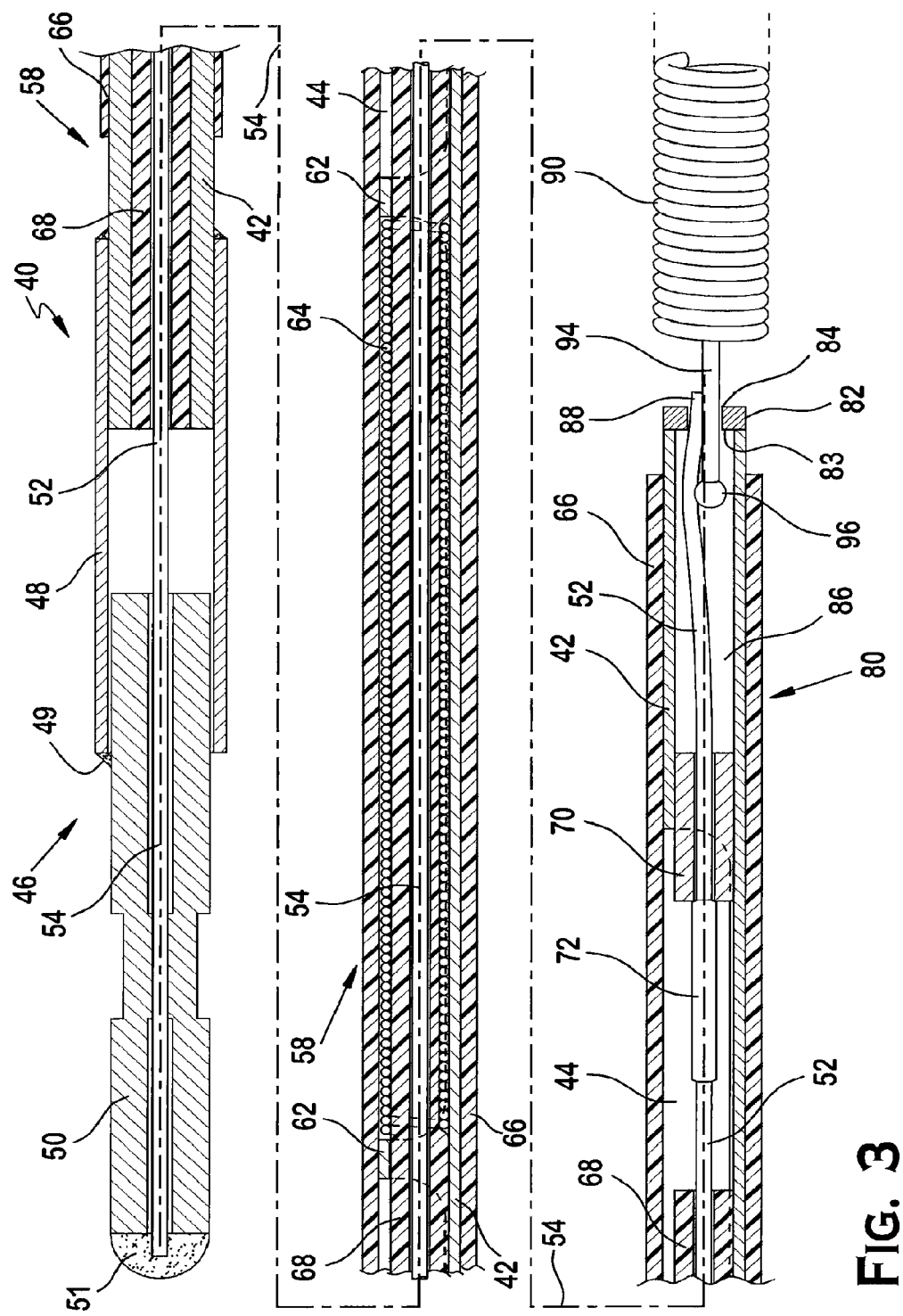
FIG. 3 is a plan cross-sectional view of the positioner of the embodiment illustrated in FIG. 1, and a plan view of a portion of an exemplary implant.
Figure 4:
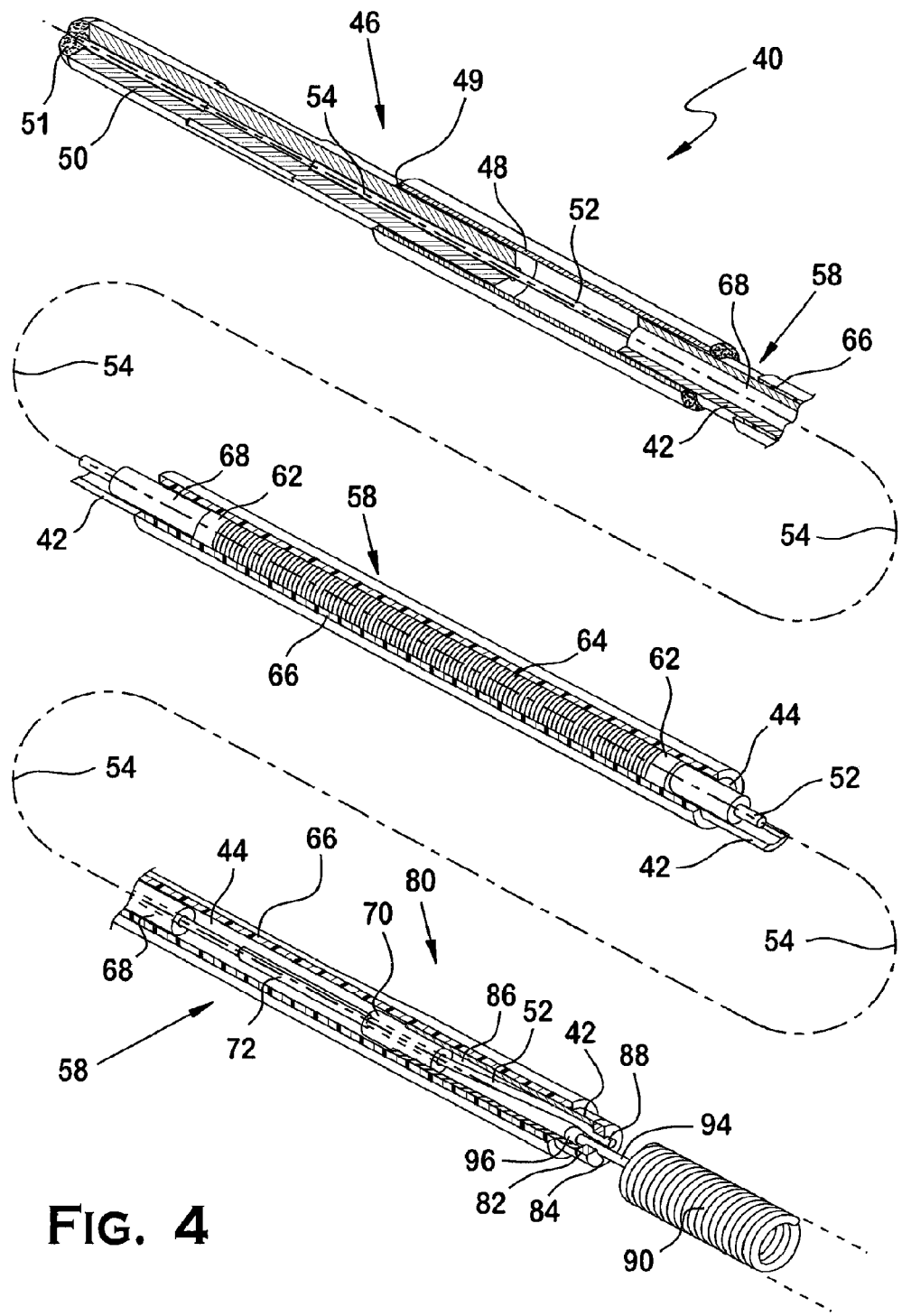
FIG. 4 is an isometric view of the positioner and exemplary implant of FIG. 3, with the positioner shown in partial quarter section.
Figure 24:
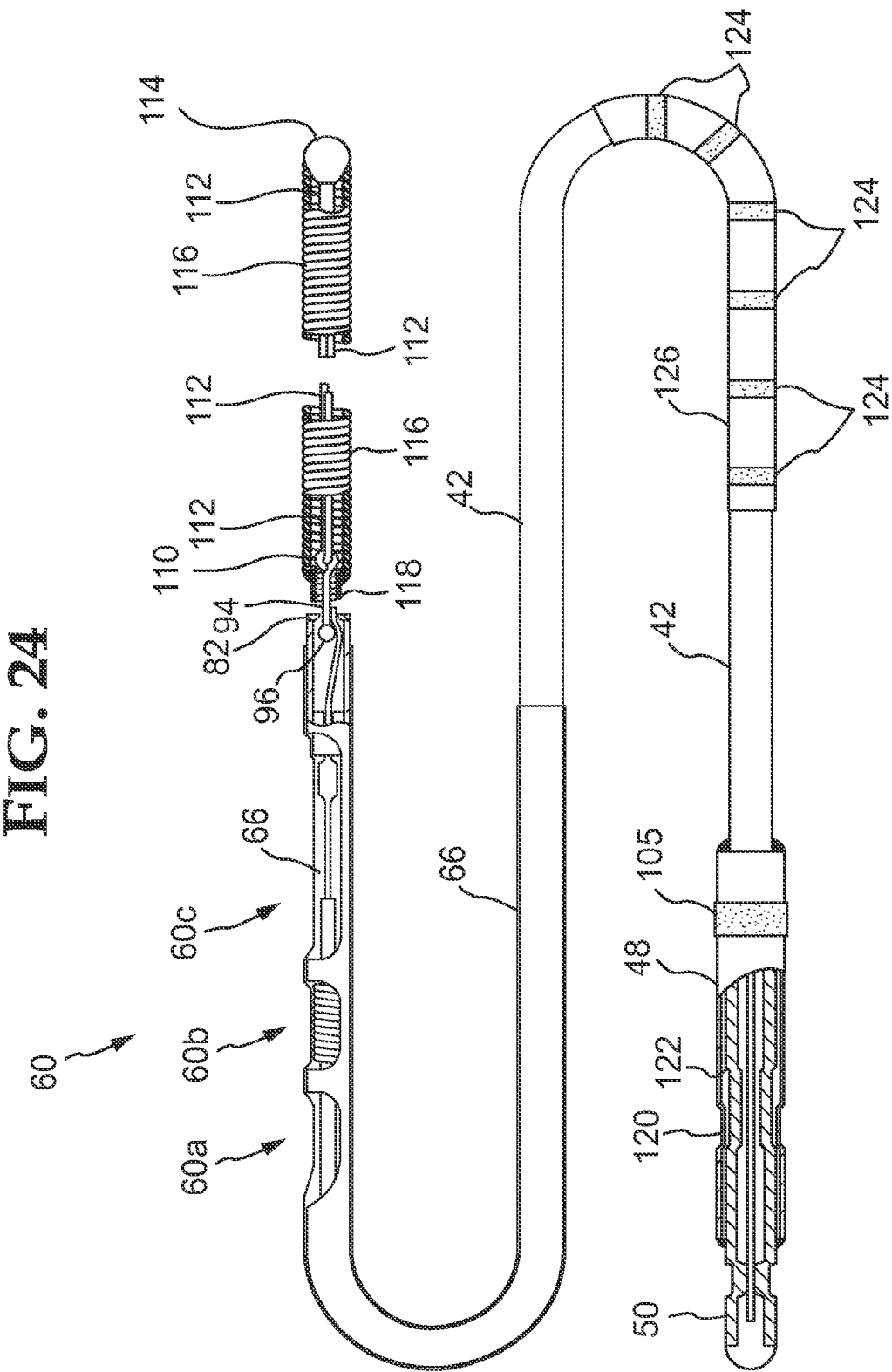
FIG. 24 is a plan view of another embodiment of the positioning system of FIG. 1 with partial cross-sectional views, and with a partial cross-sectional plan view of a preferred implant.

The positioner is an elongate, flexible structure that transfers the controlling force applied by the operator at the proximal end to the implant interface at the distal end. As illustrated in FIGS. 3 and 4, the positioner 40 preferably includes a positioner tube 42 that is an elongate tube containing a lumen 44. At the proximal end of the positioner tube 42 is an actuator interface 46 that has an outer tube 48 fixed to the proximal end of the positioner tube 42. The proximal end of the outer tube 48 encloses a distal end of a slider 50 that slides within the outer tube 48. The slider 50 receives the proximal end of the cord 52, and pulls or pushes the cord 52 when moved by the operator. Proximal to the slider 50 is an end weld 51 connecting to the proximal-most end of the cord 52. The distal end of the positioner tube 42 engages the implant interface 80 and terminates at an end cap 82. The end cap 82 has a port 84 through which the lumen 44 communicates with the exterior environment of the positioner 40 or the interior of the microcatheter 14, depending on the position of the positioner 40 in relation to the microcatheter 14. The end cap 82 also provides an end cap surface 83 that opposes the cord 52, and that prevents the disengagement of the implant 90 from the implant interface 80. As illustrated in FIG. 24, the proximal edges of the end cap 82 at the port 84 are preferably rounded or chamfered.

As also illustrated in FIGS. 3 and 4, and illustrated in FIGS. 5A-5D, the positioner tube 42 has a central axis 54 and a wall 56 running the length of the positioner tube 42. At the proximal end 42a and distal end 42b of the positioner tube 42, the wall 56 is circumferential and forms a fully enclosed tube around the lumen 44. A middle portion 58 of the positioner tube 42 has a wall 56 that is skived for most of the length of the middle portion 58, where the wall 56 does not fully circumferentially surround the lumen 44, as illustrated in FIGS. 5A, 5C, and 5D. "Skived" can also include a channel or a scalloped or gouged opening in the wall 56 of the positioner tube 42. In the skived sections 60 of the middle portion 58, the wall 56 only partially encloses the lumen 44 and forms a longitudinal aperture exposing the lumen 44. Because the wall 56 in the skived sections 60 of the middle portion 58 has less material, it is more flexible than the fully enclosed wall 56 of the proximal and distal ends of the positioner tube 42 when subjected to a bending force curving the axis 54 of the positioner tube 42 or to a rotational force twisting the positioner tube 42 about the axis 54. The thickness of the wall 56 also varies over the length of the positioner tube 42, with a relatively thick wall 56 towards the proximal end 42a and a relatively thin wall 56 towards the distal end 42b, as illustrated in FIGS. 5B and 5C. As illustrated in FIGS. 5A and 5D, the degree of skiving in the skived section 60 also varies along the length of the positioner tube 42, with greater skiving occurring towards the distal end 42b of the positioner tube 42.

At two points 62 along the length of the middle portion 58 there are areas where the wall 56 transitions from a partial wall to a full wall circumferentially enclosing the lumen 44, similar to the wall 56 in the proximal and distal ends of the positioner tube 42. Between these two points 62 is a positioner marker 64, as illustrated in FIGS. 3 and 4, which is detectable by common imaging systems. Positioner marker 64 has an outer diameter that is greater than the inner diameter of the lumen 44, in order to maximize the visibility of the positioner marker 64 when viewed with common imaging techniques. The two points 62 provide a precise location along the length of the positioner tube 42 for the positioning of the positioner marker 64, and prevent the positioner marker 64 from migrating during assembly or use. In use, the positioner marker 64 aids in the proper alignment of the positioner 40 with a microcatheter marker 15 as illustrated in FIG. 2C, and indicates when the positioner 40 is in the correct position relative to the microcatheter 14 for the disengagement of the implant 90. Preferably, one or both of the two points 62 are disposed at a predetermined distance or distances from each other, from the end cap 82, from either end of the positioner tube 42, and/or from a positioner marker such as marker 124. Most preferably, the predetermined distance is within a 0.2 mm tolerance.

Referring to FIGS. 3 and 4, enclosed around the longitudinal length of the positioner tube 42 is a positioner tube sleeve 66 that provides a sliding exterior surface to the positioner tube 42 that facilitates the insertion and sliding of the positioner tube 42 into and through the microcatheter 14. The positioner tube sleeve 66 increases lubricity between the positioner tube 42 and the inner lumen surface of the microcatheter 14 and increases the structural integrity of the positioner tube 42. It is particularly advantageous to reduce friction between the positioner tube 42 and the microcatheter 14 at the distal one third of the positioning system 10 as this distalmost portion is subject to tortuous anatomy that causes additional friction between moving components. The wall thickness of the positioner tube sleeve 66 varies along its longitudinal length, and, as best illustrated, in FIG. 3, generally has a relatively thick wall thickness towards the distal end 42b of the positioner tube 42, oppositely arranged as compared to the varying thickness of the wall 56 of the positioner tube 42. The combination of the thickness of the wall of the positioner tube sleeve 66 and the oppositely arranged thickness of the wall 56 of the positioner tube 42 provides a consistent outer diameter of the positioner 40 along portions of the length of the positioner 40, and a profile that slidably engages the interior of the microcatheter 14. As illustrated in FIG. 24, portions of the positioner tube sleeve 66 preferably conforms to the shape of the structure contained within the sleeve, thereby having an smaller outer diameter where the sleeve 66 covers the skived sections 60 of the positioner tube 42 as compared to the larger outer diameter where the sleeve 66 covers non-skived sections of the positioner tube 42. As also illustrated in FIG. 24, the positioner tube sleeve 66 preferably covers only the distal half of the positioner 40. As further illustrated in FIG. 24, the skived sections 60 preferably includes multiple skived sections that are identified as skived sections 60a, 60b, and 60c, with one or all of the skived sections disposed at a predetermined distance from each other from the end cap 82, from either end of the positioner tube 42, and/or from a positioner marker such as marker 124.

A cord liner 68 disposed upon the inner surface of positioner tube 42 within the lumen 44 encloses the cord 52 to provide a sliding surface that guides the cord 52, preferably along the axis 54. The cord liner 68 also passes through the interior of the positioner marker 64, reducing in diameter where it engages the positioner marker 64. It is advantageous to insert a low-friction material between the surface of the cord 52 and the positioner tube 42 in order to reduce the frictional drag acting on the cord 52 when moved within the positioner tube 42, it is particularly advantageous to reduce friction at the distal one third of the positioner tube 42 and the cord 52 as these distal-most portions are subject to tortuous anatomy causing additional friction between the cord 52 and the cord liner 68.

The cord 52 slides within the lumen 44, and the lumen of the cord liner 68, from the actuator interface 46 to the implant interface 80. As illustrated in FIGS. 3 and 4, at the implant interface 80, the positioner tube 42 encloses a stopper 70 fixed within the inside of the positioner tube 42 near where the positioner tube 42 transitions from a skived portion to a fully-enclosed portion. The stopper 70 functions to guide and control the movement of the distal portion of the cord 52. Just proximal of the stopper 70, the cord 52 is limited from further distal movement within the positioner tube 42 by a coining area 72, which is an enlarged portion of the cord 52 that is too large to pass distally through the central lumen of the stopper 70. The configuration of the stopper 70 and coining area 72 allows the cord 52 to be compressively biased in the distal direction against the stopper 70, which aids in assembly and maintains the distal end of the cord 52 in a distally forward position. The compression of the cord 52 can cause a portion of the cord 52 to flex and assume a position that is adjacent to the axis 54, and possibly against the inner surface of positioner tube 42.

More preferably, the positioner tube 42 is made from a material that is flexible and strong enough to transfer forces applied by the operator at the proximal end to the implant interface 80, such as 304 stainless steel hypotube, polymeric extrusion, braided extrusion, or non-elongating polymeric material that has a 0.010-0.018 inch outer diameter and a 0.005-0.012 inch inner diameter, with a 10-60 cm length of the distal end of the positioner tube 42 ground to a 0.008-0.016 inch outer diameter to reduce girth and increase flexibility. The outer tube 48 is more preferably made of 304 stainless steel hypotube, polymeric extrusion, braided extrusion, or non-elongating polymeric material with a 0.012-0.020 inch outer diameter, a 0.010-0.018 inch inner diameter, and a length of 1-15 cm, fitted over the proximal 1-50 mm of the positioner tube 42 and circumferentially welded to the positioner tube 42. The slider 50 is more preferably made of a 304 stainless steel hypotube segment, polymeric extrusion, or steel alloys and crimped to the proximal end of the cord 52, with a 0.010-0.018 inch outer diameter, a 0.001-0.016 inch inner diameter, and a length of 1-15 cm. The end cap 82 is more preferably made of a 0.001-0.005 inch thick 304 stainless steel, polymeric material, or steel alloy retainer ring with a 0.008-0.018 inch outer diameter and a 0.003-0.009 inch diameter port welded or bonded to the distal end of the positioner tube 42. The positioner marker 64 is more preferably a radiopaque platinum/iridium or platinum/tungsten coil disposed in the lumen 44 and having a 0.008-0.018 inch outer diameter, a 0.005-0.015 inch inner diameter, and a 1-6 mm length. The positioner tube sleeve 66 is more preferably made of a polytetrafluoroethylene (PTFE) or low-friction polymeric material having a friction coefficient of 0.2 or less, heat shrunk onto all or at least the distal most portion of the positioner tube 42. The cord liner 68 is more preferably made of PTFE or other low-friction materials and has a 0.002-0.006 inch inner diameter and a 0.004-0.008 inch outer diameter. The cord 52 is more preferably a cord, wire, rod, tube, thread or filament made of a metal or polymer with a circular cross section and a 0.001-0.005 inch outer diameter. The stopper 70 is more preferably made of 304 stainless steel, polymeric extrusion, braided extrusion, or non-elongating polymeric material with approximately a 0.001-0.012 inch inner diameter, and is welded to the interior of the positioner tube 42. The coining area 72 more preferably has a 0.0015-0.0120 inch width. The length of the cord 52 proximal to the stopper 70 (e.g., between the proximal end of the positioner tube 42 and the proximal end of the stopper 70) is more preferably slightly longer than the corresponding length of the structure adjacent to the length of the cord 52 (e.g., the length of positioner tube 42 corresponding to the length of the cord 52) by 0.001-0.040 inches, thereby compressively biasing the cord 52 so that it maintains the coining area 72 against the stopper 70 until the cord 52 is moved in the proximal direction.

Most preferably, the positioner tube 42 is made from 304 stainless steel hypotube and has a 0.012 inch outer diameter and a 0.007 inch inner diameter, and a 50-60 cm length of the distal end of the positioner tube 42 is ground to a 0.010 inch outer diameter to reduce girth and increase flexibility. The outer tube 48 is most preferably made of 304 stainless steel hypotube with a 0.016 inch outer diameter, a 0.0122 inch inner diameter, and a length of 6 cm, fitted over the proximal 5 mm of the positioner tube 42 and circumferentially welded to the positioner tube 42. The slider 50 is most preferably made of a 304 stainless steel hypotube segment crimped to the proximal end of the cord 52, with a 0.012 inch outer diameter, a 0.003 inch inner diameter, and a length of 4 cm. The end cap 82 is most preferably a 0.002-0.003 inch thick 304 stainless steel retainer ring with an approximate 0.010 inch outer diameter and an approximate 0.0043 inch diameter port welded to the distal end of the positioner tube 42. The positioner marker 64 is most preferably a radiopaque platinum/tungsten coil disposed in the lumen 44 and having an 0.008 inch outer diameter, a 0.006 inch inner diameter, and a 3 mm length. The positioner tube sleeve 66 is most preferably made of PTFE, heat shrunk onto most of the length of the positioner tube 42. The cord liner 68 is most preferably made of PTFE and has a 0.003 inch inner diameter and a 0.005 inch outer diameter. The cord 52 is most preferably a 304 stainless steel Hyten™ cord sold by Fort Wayne Metals of Indiana, with a circular cross section and an 0.00185 inch outer diameter. The stopper 70 is most preferably made of 304 stainless steel with a 0.0022 inch inner diameter, and is welded to the interior of the positioner tube 42. The coining area 72 most preferably has a 0.0028 inch width. The length of the cord 52 between the proximal end of the positioner tube 42 and the proximal end of the stopper 70 is most preferably longer than the corresponding length of the positioner tube 42 by 0.027 of an inch, thereby compressively biasing the cord 52 so that it maintains the coining area 72 against the stopper 70 until the cord 52 is moved in the proximal direction.

Although specific materials, dimensions, and characteristics are described in regard to the illustrated embodiments, it is appreciated that alternative designs can achieve the same operational objectives of the described components and structures. For example, to control the flexibility of the positioner tube 42, instead of skived sections 60 of the wall 56 at the middle portion 58, the wall 56 can fully or partially enclose the lumen 44 and include a plurality of slots or gaps to increase the flexibility of the wall. The slots or gaps can have a depth that reaches through the entirety of the wall 56 to form holes communicating with the lumen 44, or the slots and gaps can have a depth that reaches only partially into the surface of the wall 56. The slots or gaps can be longitudinal and parallel with the axis 54, transverse or orthogonal to the axis 54, or at an angle to the axis 54. Instead of slots or gaps, the wall 56 can have circular or oval holes partially or fully through the wall 56. In another alternative, the middle portion 58 of the wall 56 can have a spiral cut along all or part of the length of the middle portion 58 to increase the flexibility of the wall. In yet another alternative, the thickness of all or part of the wall 56 in the middle portion 58 can be reduced to increase flexibility. In still another alternative, instead of a tube or a skived tube, the positioner tube 12 can have a series of tubes and/or partial tubes longitudinally aligned with a stiffening member between the tubes and/or partial tubes. Likewise, the end cap 82 can be replaced by a partial or whole loop, ring, or eyelet defining a port 84, and/or carried by a stiffening member disposed at a distance from the positioner tube 42.

In another alternative, instead of the end cap 82, the distal end of the positioner tube 42 can be formed to have an end crimp, cone shape, or dome shape to reduce the diameter of the distal end of the positioner tube 42 and form the port 84, and to also form a surface that engages the cord 52 and implant 90 to prevent the disengagement of the implant 90 from the implant interface 80. An alternative in which the end cap 82 is replaced with an end dome 81, made from the crimping of the distal end of the positioner tube 42, is illustrated in FIGS. 6A and 6B.

In yet another alternative, instead of a positioner tube sleeve 66, the exterior of the positioner tube 42 or the interior of the microcatheter 14 can be coated with a lubricating material or a lubricant. Also, instead of being disposed on the inner surface of the lumen 44, the cord liner 68 can be disposed on a portion of the cord 52. In another alternative, the exterior of the cord 52 or the inner surface of lumen 44 can be coated with a lubricating material or a lubricant.

In yet another alternative, instead of the coining area 72, the outer diameter of the cord 52 at the position of the coining area 72 can be made larger than the lumen of the stopper 70 by fixing a bushing to the cord 52. In another alternative, instead of modifying the dimensions of the cord 52 at the coining area 72 to limit its distal movement through the lumen of the stopper 70, the cord 52 can instead be provided with a bend or twist that impedes the distal movement of the cord 52 into the lumen of the stopper 70. Yet another alternative is for the cord 52 to be fixed in a distally forward position by an adhesive that can be broken when the cord 52 is subjected to sufficient force.

Another aspect of the compressively biased arrangement that maintains a portion of the cord 52 in a distally forward position, at coining area 72 and its alternatives, is that the positioner tube 42 must be sufficiently strong to maintain the arrangement so that the distal end of the cord does not leave its position proximate the port 84 or permit the premature release of the ball 96 from the cavity 86. Preferably, the positioner tube 42 can maintain the position of the cord 52 relative to the port 84 when subjected to an elongation force of more than 3 Newtons, and more preferably, an elongation force of more than 2 Newtons.

Implant Interface

The implant interface allows the operator to mechanically control the engagement and disengagement of the implant to the positioner, and allows the positioner to retain the implant in a way that minimally contacts the implant, that permits movement in all directions of motion and rotationally, and that allows the implant to move axially and without radial movement when engaging and disengaging the implant interface. The implant interface provides mechanical control of the engagement and disengagement of the implant by retaining a member engaging the implant. The member is introduced into the implant interface through an opening in the positioning system, and retained at the implant interface by obstructing the opening at least in part, or fully, so as to physically prevent the complete exit of the member back through the opening. The obstructing is achieved with a movable elongate member disposed along the length of the positioning system with a distal end that obstructs the opening. By obstructing the opening and not fixedly restraining the implant, the implant remains free to move according to the limitations defined by the implant interface, which includes movement in the axial and radial directions compared to the axis of the positioning system, rotational movement about an axis of the implant, and angular movement that disposes the implant at an angle as compared to the axis of the positioning system. Furthermore, by obstructing the opening and not directly restraining the implant, the contact between the implant interface and the implant is minimized.

As illustrated in FIGS. 3 and 4, the cord 52 is preferably disposed at the implant interface 80. A distal tip 88 of the cord 52 is positioned in the port 84 of the end cap 82 so that it partially obstructs the port 84 when the cord 52 is at its most distally advanced position in the positioner tube 42. The distal tip 88 is preferably deformable so that it can be offset from the axis 54 of the positioner tube 42 and enter the port 84 near the edge of the port. The positioner tube 42, the end cap 82, and the distal surface of the stopper 70 define a cavity 86 within the implant interface 80.

The cord 52 preferably has engaged and disengaged orientations illustrated, respectively, in FIGS. 7A and 7B. In the engaged orientation illustrated in FIG. 7A, the cord 52 is at its most distally advanced position in the positioner tube 42 with, in the illustrated embodiment, the coining area 72 abutting the stopper 70. The distal tip 88 of the cord 52 is disposed within the port 84 in the end cap 82, and the cord 52 is maintained in the engaged orientation by the actuator interface 46. In the disengaged orientation illustrated in FIG. 7B, the cord 52 has been moved in the proximal direction relative to the positioner tube 42, with the coining area 72 disposed at a distance proximal to the stopper 70. The distal tip 88 of the cord 52 is proximal of the port 84 in the end cap 82 and no longer obstructing or fully obstructing the port 84, and the cord 52 is maintained in the disengaged orientation by the actuator interface 46. After achieving the disengaged orientation, a ball 96 carried by a rod 94 and engaging the implant 90 is free to move distally through the port 84 or, alternatively, the positioner tube 42 or the entire positioner 40 can be moved in the proximal direction to allow the ball 96 to exit the positioner tube 42. The engaged orientation, disengaged orientation, and the exit of the ball 96 from the implant interface 80 are illustrated in FIGS. 8A, 8B, and 8C, respectively. As illustrated in FIG. 24, the proximal edges of the end cap 82 at the port 84 are preferably rounded or chamfered to facilitate the exit of the ball 96 from the implant interface 80.

In an alternative embodiment illustrated in FIGS. 9 and 10, the distal tip 88 of the cord 52 is not disposed in the port 84 of the end cap 82 but instead abuts against the proximal end cap surface 83 of the end cap 82 in the engaged orientation illustrated in FIGS. 9 and 10. The diameter or thickness of the distal tip 88 is sufficient to obstruct the port 84 in the engaged orientation, and the proximal movement of the distal tip 88 removes the obstruction from the proximal edge of the port 84 to assume the disengaged orientation illustrated, in FIG. 7B. Since the end cap 82 provides an abutting end cap surface 83 that opposes the distal movement of the cord 52, the obstruction of the port 84 can be achieved with or without the stopper 70 and coining area 72, and the cord liner 68 can be disposed more distally into the implant interface 80, as illustrated in FIGS. 9 and 10. The compressive biasing of the cord 52 can be maintained by compressing the distal tip 88 against the end cap surface 83 of the end cap 82, and the cavity 87 can be defined by positioner tube 42, the end cap 82, the end cap surface 83, and the distal surface of the cord liner 68.

Implant

The implant can be any implant that can be retained and positioned by the positioning system. The implant is retained by the implant interface with an extension engaging the implant. The extension can be a part of the implant when the implant is made, a modified portion of the manufactured implant, or attached to the implant after initial manufacturing. The extension provides an end that is disposed at a distance from the implant body, and allows the implant interface to engage and, secure the implant by securing the end of the extension. The implant body itself, however, is not connected to the implant interface.

In the embodiment illustrated in FIGS. 1A-1B and 2B-4, the implant 90 is a neurological coil. The neurological coil implant 90 illustrated in FIGS. 1A-1D is shown in a coiled orientation prior to insertion into the microcatheter 14, and the neurological coil implant 90 shown in FIGS. 2B-4 is shown in a truncated form for simplicity and disposed in alignment with the axis 54 and the interior of the microcatheter 14 (not shown in FIGS. 2B-4). The neurological coil implant 90 shown in FIG. 2C is shown in an implanted state, disposed in an aneurysm. The implant 90 preferably has a rod 94 engaging the implant 90 in the proximal direction, with the rod 94 including an eyelet 110 engaging a stretch-resistant member 112, as illustrated in FIG. 24. More preferably, the stretch-resistant member 112 can pass through the eyelet 110 and wrap the eyelet 110 to form a knot and, most preferably, form a hitch knot. As illustrated in FIGS. 3-4, when engaging the implant interface 80, the rod 94 is disposed in the port 84 in the end cap 82 and terminates with the ball 96 disposed proximal of the end cap 82 in the cavity 86. The ball 96 has a cross sectional area that is less than a cross sectional area of the port 84, which allows the ball 96 to pass freely through the port 84 when the positioner 40 is in the disengaged orientation illustrated in FIG. 7B. When in the engaged orientation illustrated in FIGS. 3-4 and 7A, the distal tip 88 of the cord 52 obstructs a portion of the port 84 in the end cap 82, with another portion of the port 84 obstructed by the rod 94. The obstruction of the port 84 by the distal tip 88 reduces the available area of the port 84 so that the ball 96 can not pass through the port 84. Although physically obstructed from passing distally through the port 84 when the cord 52 is in the engaged orientation, the ball 96 and rod 94 are otherwise unrestrained and free to move and rotate within the cavity 86 and the port 84. Also, the ball 96 is retained, at the implant interface 80 but not connected to any portion of the positioning system 10. The ball 96 is thus free to move independently of the positioning system 10 in any direction within the confines of the cavity 86 and, particularly, is free to move in the direction parallel or radial to the axis 54 of the positioner tube 42, free to move in to a position in which a central axis of the implant 90 is at an angle relative to the axis 54, and free to rotate around the central axis of the implant 90.

The freedom to rotate the ball 96 and implant 90, facilitated by the illustrated embodiment, is advantageous. It is believed that in existing systems, the implant or a portion of the implant is firmly held by the delivery system and not free to rotate and, when the implant and delivery system are advanced distally to the target site through a microcatheter, the surface of the implant (especially the helical surface of some neurological coils) can induce a torque within the implant when moved along the inner surface of a microcatheter. That torque is stored as a potential energy in a compressed spring within the implant itself and within the connection between the implant and the delivery system. When the implant then emerges from the microcatheter at the target site, it is believed that the potential energy can be released suddenly and cause the implant to twist unpredictably and deposit itself in an undesirable location. The positioning system 10 facilitates the unhindered rotation of the ball 96 and implant 90, thereby avoiding this problem that is believed to exist with existing delivery systems. The free rotation of the implant 90 and ball 96 allows the implant 90 to be deployed from the microcatheter 14 at the target site 16 much more gently than with existing systems having a connection that is rigid or that partly or wholly limits movement and rotation between the implant and delivery system, and the free rotation also lowers the force applied to the vasculature during deployment and positioning of the implant 90 at the target site 16.

The relationship between the implant interface and the implant establishes some of the dimensions of these components. The implant interface provides an opening having a first opening area and a second opening area. The implant provides an extension that is disposed in the implant interface through the opening, and that has a portion (such as the ball 96) that can pass through the first opening area but can not pass through the second opening area. The portion of the extension has an obstruction dimension that defines a structural arrangement that prevents the portion from passing through the structure defining the second opening area at the opening. The obstruction dimension also defines the structural arrangement that permits the portion to pass through the structure defining the first opening area. This relationship can be expressed as follows:

$$\text{first opening area} > \text{obstruction dimension} > \text{second opening area} \quad \text{Equation (1)}$$

The implant interface and implant extension use this relationship by having implant interface structure that forms the second opening area to be smaller than the obstruction dimension of the implant extension, to physically block passage of the portion of the extension through the opening, and implant interface structure that forms the first opening area to be larger than the obstruction dimension, to allow passage of the portion of the extension through the opening.

In the embodiment illustrated in FIG. 11A, the principles of Equation (1) can be applied to relate the size of the ball 96 to the dimensions of the port 84 and distal tip 88 of the cord 52 by the following relationship:

$$p > b > (p-w) \quad \text{Equation (2)}$$

where "p" is the cross sectional dimension of the port 84, "b" is the cross sectional dimension of the ball 96, and "p−w" is the cross sectional dimension of the port 84 less the cross section dimension of the distal tip 88 of the cord 52. In the illustrated embodiment, the relationship of Equation (2) is applied to structures having circular cross sections. However, it is appreciated that the principles of Equation (1) can be applied to structures having non-circular geometries, such as a rod 95, with a triangular cross section, or ports 85 and 89, with a non-circular shape, as illustrated, in FIGS. 15 and 16.

In alternative embodiments, the ball 96 can be replaced with another structure that can effectively pass through an unobstructed port 84 but not pass through an obstructed port 84, such as a disc, hook, or ring structure. Likewise, the distal tip 88 can be modified to obstruct only selected portions of the port 84, or to more closely abut against the inner surface of positioner tube 42 within cavity 86 in order to provide a larger space for the ball 96 to freely rotate or otherwise move within the cavity 86. In another alternative, the distal tip 88 can have a cross-sectional shape that is noncircular. For example, as illustrated, in FIG. 11B, the cross-section shape of the distal tip 88 can be ovoid and, as illustrated in FIG. 11C, the cross-section shape of the distal tip 88 can be arcuate. Also, in another alternative, the rod 94 can engage the implant 90 at an angle relative to a central axis of the implant 90, or at an angle relative to the axis 54 of the positioner tube 42.

The illustrated embodiment advantageously provides for the unrestrained axial movement of the ball 96 within the cavity 86 of the implant interface 80. The movement of the ball 96 within the cavity 86 is related to the longitudinal length of the cavity 86 and the length of the rod 94 engaging the implant 90 into the cavity 86. As illustrated in FIG. 12, the rod 94 is of sufficient length to allow the axial movement of the ball 96 and implant 90 in the direction of the axis 54 of the positioner tube 42. When the implant 90 and positioner tube 42 are both advanced in the distal direction, as illustrated in FIG. 12, it can be appreciated that friction against the surface of the implant 90 will cause the ball 96 to move axially to an extreme proximal position in the cavity 86 and the proximal surface of the implant 90 will abut the distal surface of the end cap 82 and align the implant 90 with the axis 54 of the positioner tube 42. When distally advanced, with the implant 90 abutting the end cap 82, there is a slight frictional adhesion where the implant 90 and the end cap 82 contact each other.

When the positioner tube 42, or implant 90 and positioner tube 42, are advanced in the proximal direction as illustrated in FIG. 13, it can also be appreciated that friction against the surface of the implant 90 will cause the ball 96 to move distally to an extreme distal position in the cavity 86, and that there will be minimal or no frictional contact between the end cap 82 and the implant 90. The differing frictional characteristics related to the axial movement of the ball 96 in the cavity 86, and the degree of contact between implant 90 and the implant interface 80, provides a "friction push" and a "frictionless pull" to the positioning system 10 that is appealing to the operator because it provides an additional tactile sensation related to the movement of the system, it is believed that existing systems that do not permit axial movement of the implant, or that do not provide a reduced or variable friction or frictionless interaction between the implant and delivery system, provide the operator less tactile sensation when moving these existing delivery systems.

Also, the axial movement of the ball 96 in the cavity 86 advantageously permits the implant 90 to assume an angled orientation compared to the axis 54 of the positioner tube 42, and articulate or pivot around the ball 96. As illustrated in FIG. 13, the rod 94 can be disposed at an angle 98 to the axis 54 of the positioner tube 42, and that angle 98 is increased as the ball 96 nears an extreme distal position in the cavity 86. That angled orientation and articulation advantageously assists in the relaxation and discharge of potential energy or spring forces in the implant 90, or between the implant 90 and the positioning system 10, as the implant is moved through the microcatheter 14. The angulation can preferably be approximately 10-50 degrees between the centerline of the rod 94 and the axis 54 of the positioner tube 42, and more preferably be approximately 30 degrees. Also, when the implant 90 is observed to have an angled orientation with an imaging system, the operator can readily determine that the implant 90 is not experiencing potential energy or spring forces that could be later released when the implant 90 is deposited at the target site 16. It is believed that existing delivery systems that do not permit angulation or articulation of the implant do not provide this information to the operator.

In an alternative embodiment illustrated in FIGS. 14-15, the port 85 of the end cap 82 can be non-circular or have a notch that advantageously permits a greater angulation or articulation than can be achieved with the circular-shaped port 84, permitting an angle 99 between the centerline of the rod 94 and the axis 54 of the positioner tube 42. Similarly, the rod can have various cross-sectional shapes, such as a triangular shape of rod 95 as illustrated in FIG. 16, that interfaces with a complimentary-shaped port 89 in order to maintain a specific articulation (by the alignment of the triangular shape of rod 95 with a triangular notch of port 89) when the implant interface 80 is operated to orientate the rod 95 so that the implant 90 is disposed in a specific direction. It can be appreciated, that a slight proximal movement of positioner 40 may be necessary to maintain sufficient contact between the rod 95 and the port 89 illustrated in FIG. 16. As also can be appreciated from FIGS. 13-16, the angulation can also be increased or decreased by the adjusting the inner diameter of the port 84 or by adjusting the thickness of the end cap 82. Specifically, a greater inner diameter of the port 84 will allow the rod 94 to assume a greater angle 98, and a thinner end cap 82 will allow the ball 96 to assume a more distal position in the cavity 86 and permit a greater angle of the rod 94 through the port 84. As can be further appreciated, a desired angulation can be preset in the design of the implant interface 80 by controlling the length and cross-sectional dimensions of the rod 94, the diameter of the port 84, and the thickness of the end cap 82.

Also, for example, the port 84 can have a conical shape or a shape in which one end of the port 84 is wider than the other end of the port 84, so that the rod 94 can assume a greater or a preset angle relative to the positioner 40.

The positioning system 10 of the illustrated embodiment also advantageously captures or recaptures an implant 90 already located at or proximate the target site 16. As can be appreciated in the reverse sequence of FIGS. 8A-8C, in the order of 8C to 8B to 8A, with the directional arrows of FIGS. 8B and 8C reversed, the positioner tube 42 can be advanced distally through the microcatheter 14 (without the implant 90) to an implant 90 already positioned at the target site 16 or, if the implant 90 was just released from the implant interface 80, the positioner tube 42 can be maneuvered proximate to the just-released implant 90. As can also be appreciated from FIG. 8C, the end cap 82 can be moved over the ball 96 so that the ball 96 passes through the port 84 and into the cavity 86 of the implant interface 80, and the distal tip 88 of the cord 52 can be distally advanced to obstruct the port 84 to retain the ball 96 and assume the engaged orientation. The implant 90 can then be moved or entirely withdrawn from the target site 16. In an alternative embodiment, the ball 96 and end cap 82 can be made of a material that can be imaged with standard imaging technologies, such as a radiopaque material, in order to assist with the positioning of the end cap 82 in relation to the ball 96.

Figure 17A:
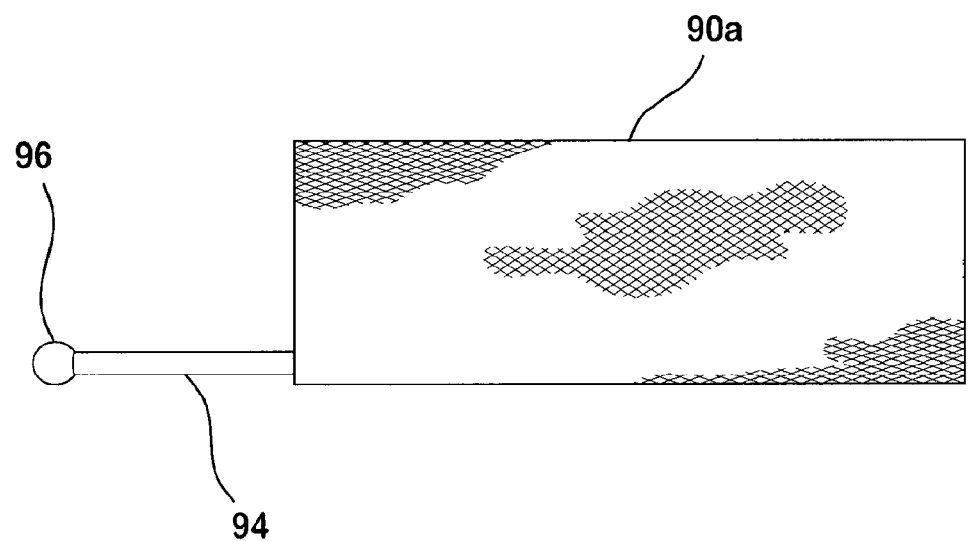
FIG. 17A is a plan view of an alternative implant.
Figure 17B:
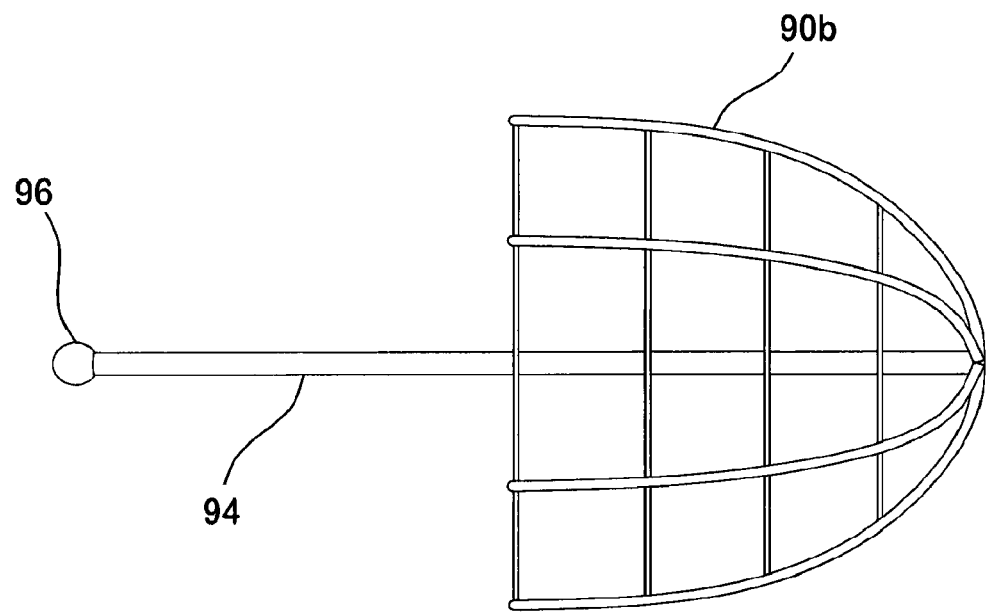
FIG. 17B is a plan view of another alternative implant.

Commercially available embolic coils suitable for use with the delivery system 10, when modified to include the ball 96 or a combination of the rod 94 and ball 96, include the Sapphire™, NXT™, and Nexus™ embolic coils, commercially available from EV3, Inc. of Plymouth, Minn. USA. Although the implant 90 of the illustrated embodiment is a neurological coil, the implant 90 can be any implant that can be inserted with a catheter, such as a stent stent-graft 90a as illustrated in FIG. 17A or an embolic filter 90b as illustrated in FIG. 17B. Commercially available stents suitable for use with the delivery system 10, when modified to include the ball 96 or a combination of rod 94 and hall 96, include the IntraCoil®, IntraStent®, ParaMount™, PRIMUS™, and PROTÉGÉ® stents, commercially available from EV3, Inc. of Plymouth, Minn. USA. A commercially available embolic protection device suitable for use with the delivery system 10, when modified to include the ball 96 or a combination of rod 94 and hall 96, is the SpideRX® embolic protection device, commercially available from EV3, Inc, of Plymouth, Minn. USA.

Actuator Interface

The actuator interface provides the operator the ability to control the movement of the implant as it is positioned by the positioning system, and to mechanically control the selective engagement and disengagement of the implant and implant interface. The actuator interface controls the movement of the implant by providing a surface upon which the operator can exert control, so that the controlling motions of the operator are accurately transferred to the implant interface and implant through the positioner. The actuator interface provides a relatively stiff proximal end of the positioner that transfers the axially-directed and rotational forces exerted on the actuator interface by the operator to the relatively flexibly distal end of the positioning system with minimal loss due to flexing and twisting of the positioning system. The actuator interface provides control of the engagement and disengagement of the implant from the implant interface with a sliding mechanism or slider that controllably and predictably moves the implant interface between the engaged and disengaged orientations. The actuator interface also connects to an actuator that permits the operator to controllably and predictably move the slider. In addition, the actuator interface establishes and maintains a compressive biasing of the implant interface so that the implant interface remains in the engaged orientation by disposing the slider in a distally forward position.

Figure 26:
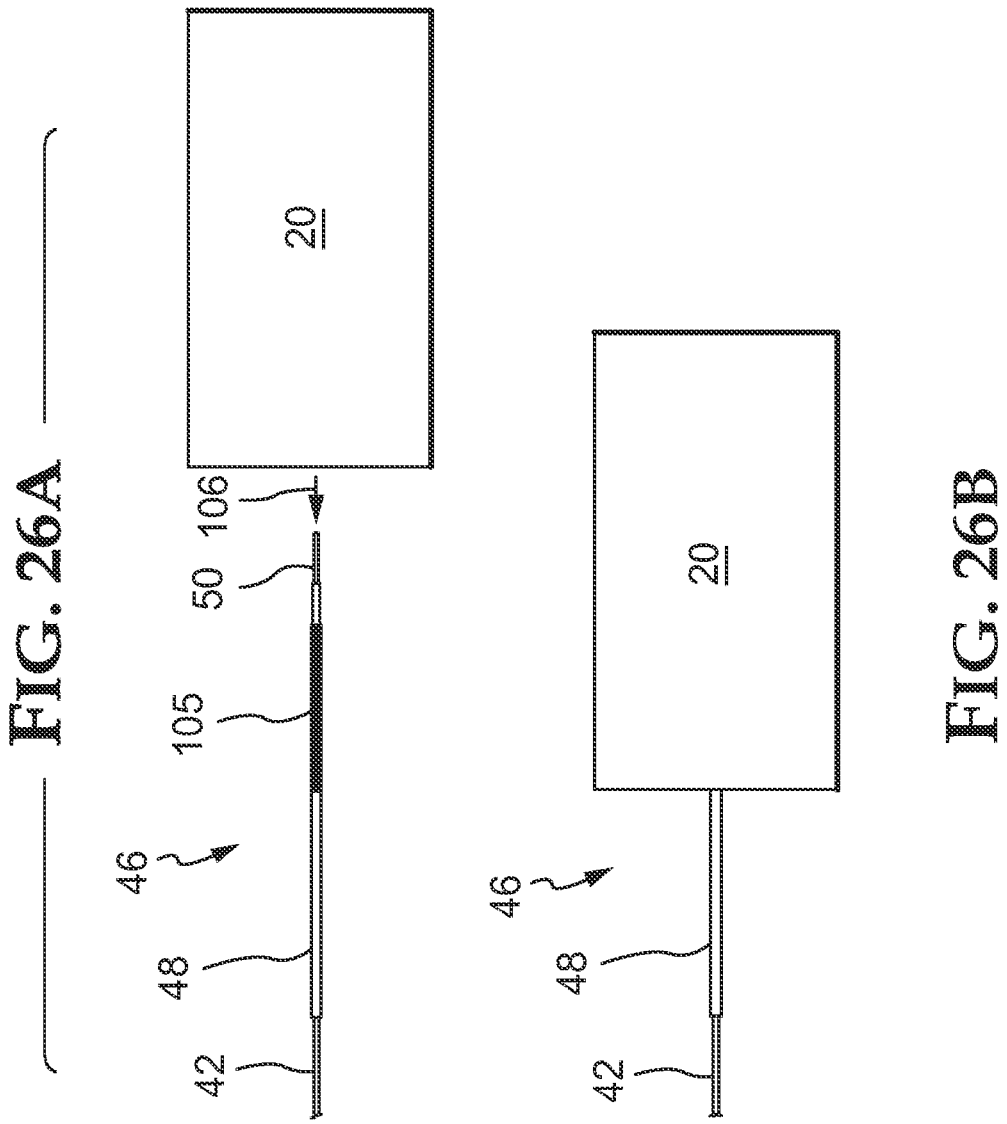
FIGS. 26A and 26B are schematic plan views of yet another embodiment of the actuator interface of FIG. 3, and of the actuator of FIGS. 21A-22B.

The compressive biasing of the cord 52 that presses the coining area 72 distally against proximal end of the stopper 70 is preferably established at the actuator interface 46. In the embodiment illustrated in FIG. 3, the proximal end of the positioner tube 42 is fixed to the outer tube 48 by a circumferential weld. The slider 50 is slidably fitted into the lumen of the outer tube 48 from the proximal end of the outer tube 48. The cord 52 is then preloaded or biased in the distal direction to create compression in the cord 52 in the coining area 72 against the stopper 70 and the slider 50 is tack welded with tack weld 49 to the outer tube 48 while preloaded, to temporarily fix the slider 50 and outer tube 48 together and maintain the implant interface 80 in the engaged orientation. When the disengaged orientation is desired, the operator slidably moves the slider 50 in the proximal direction, relative to the outer tube 48, with sufficient force to break the tack weld 49 and free the slider 50 so that it can move within outer tube 48. More preferably, a tensile force in the range of approximately 200-500 grams is required to break the tack weld 49, and little or no particulate matter is liberated with the breaking of the tack weld 49. As illustrated in FIG. 24, the outer tube 48 preferably includes a band 105 viewable by the operator of the actuator that indicates when the actuator is properly inserted into the actuator 20, in the direction of arrow 106. Specifically, when the outer tube 48 is inserted into the actuator 20, a correct depth of insertion is indicated when the marker 105 is completely within the actuator 20 and no longer viewable by the operator of the actuator, as illustrated in FIGS. 26A and 26B.

Alternatively, the biasing, fixing, and movement of the cord 52 within the positioner 40 can be achieved with a variety of designs. The slider 50 can be threaded and received into corresponding threads of the outer tube 48, with the slider 50 axially held in place relative to the outer tube 48 by the threads, and with the biasing and movement of the slider 50 controlled by the rotational movement of the slider 50 relative to the outer tube 48. In another alternative, instead of the tack weld 49, the biasing of the cord 52 and the fixing of the slider 50 can be achieved with a removable locking pin fitted through a common hole through the outer tube 48 and slider 50, temporarily fixed together with an adhesive or the pin can be breakable or bendable with a force that is similar to the force applied when breaking the tack weld 49. The slider 50 can also be temporarily fixed in place by a deformable crimp in the outer tube 48 that presses the outer tube 48 against the outer surface of the slider 50, to hold the slider 50 in place relative to the outer tube 48.

Figure 18:
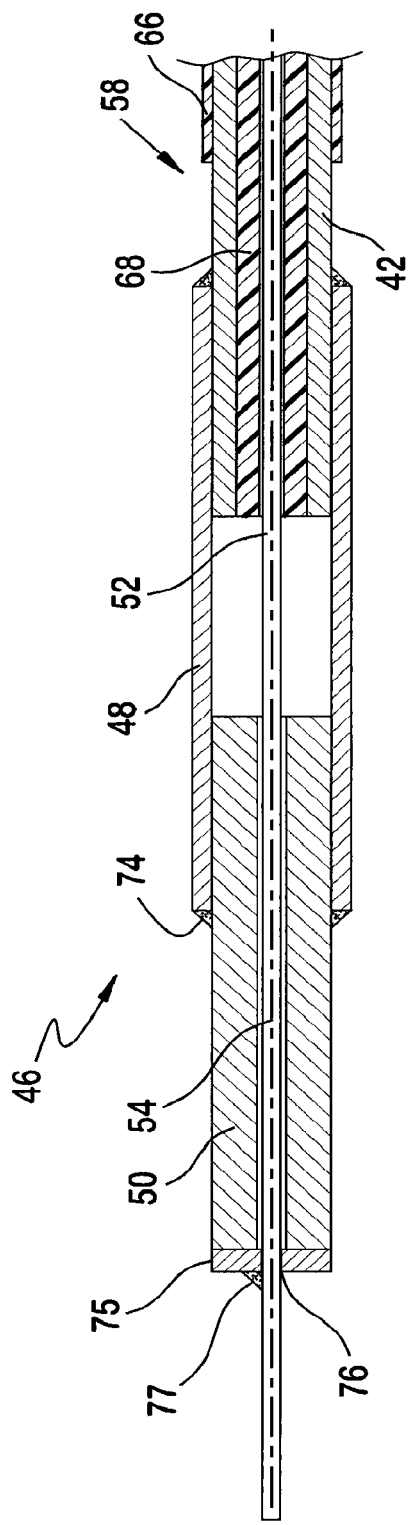
FIG. 18 is a plan cross-section view of another embodiment of the actuator interface of FIG. 3.

In another alternative embodiment illustrated in FIG. 18, the slider 50 is fixed to the outer tube 48 with a circumferential weld 74 instead of the tack weld 49 and the end weld 51 is replaced with an end cap 75 that is similar to the end cap 82 at the implant interface 80, hut having a port 76 that temporarily holds the cord 52 to the end cap 75 with a tack weld 77 similar to the tack weld 49. The proximalmost end of the cord 52 is disposed proximal to the port 76. The tack weld 77 secures the cord 52 to the end cap 75 and maintains the positioner 40 in the engaged orientation until a predetermined proximally-directed force is applied to the proximalmost portion of the cord 52 that is sufficient to break the tack weld 77. Alternatively, the end cap 75 and tack weld 77 can be replaced with a ratchet mechanism that controls or limits movement of the cord 52 in the distal direction to maintain the engaged orientation, and that permits movement of the cord 52 in the proximal direction after the cord 52 is pulled in the proximal direction by a predetermined force similar to the force required to break tack weld 77.

Figure 19:
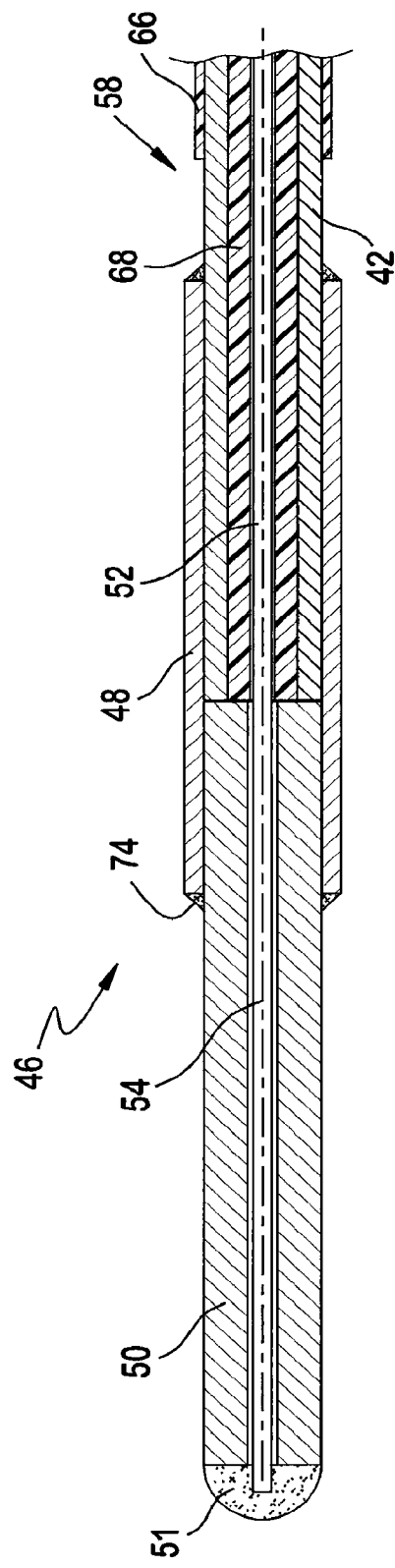
FIG. 19 is a plan cross-section view of yet another embodiment of the actuator interface of FIG. 3.

In another embodiment illustrated in FIG. 19, instead of the tack weld 49, the slider 50 is connected to the outer tube 48 with a circumferential weld 74. The cord 52 is held in the center of the positioner tube 42 along the axis 54 for the entire length of the proximal end of the positioner tube 42, with the proximal end of the cord 52 completely enclosed and held in the location of the axis 54 by the slider 50, the positioner tube 42, and the cord liner 68. In the embodiment of FIG. 19, the external components of the proximal end of the positioner 40 are fixed to each other, but the internal cord 52 remains slidably disposed along the axis 54 except at the proximalmost end of the cord 52 where it is fixed at the end weld 51. The actuator interface 46 is of sufficient length so that the operator can hold and bend the actuator interface 46 around a cylindrical object (not shown), such as the operator's finger or a cylindrical object of a predetermined diameter. When the actuator interface 46 is held against and wrapped around the cylindrical object, the cord 52 is forced to conform to an arcuate path that has a radius that is greater than a radius of a corresponding arcuate path defined by the outer surfaces of the positioner tube 42 and outer tube 48 that abut the cylindrical object, as measured from a center of the cylindrical object. As can be appreciated, the arcuate path of the cord 52 around the cylindrical object is longer than the corresponding arcuate path at the outer surfaces of the positioner tube 42 and outer tube 48 abutting the cylindrical object, which induces a movement of the cord 52 (and a movement of the distal tip 88) in the proximal direction relative to the actuator interface 46 (and relative to the end cap 82) without the use of the actuator 20. The appropriate number of times that the proximal end of the positioner tube 42 must be wrapped around the cylindrical object to cause sufficient movement of the distal tip 88 and achieve the disengaged orientation can be determined by trial and error or calculated for various sizes of the positioning system 10. In another alternative of the embodiment illustrated in FIG. 18, the outer tube 48 and the slider 50 can be omitted and the positioner tube 42 and the cord 52 can both directly engage the end weld 51.

In the embodiment illustrated in FIGS. 20A and 20B, the outer tube 48 encloses bushings 101, 102, and 103 which are disposed within the outer tube 48 and around the slider 50 and the positioner tube 42. As illustrated, the hushing 101 is fixed to the inner surface of the outer tube 48 with a circumferential weld at the proximal end of the outer tube 48, and the slider 50 is slidably disposed within the inner surface of the bushing 101 but temporarily fixed to the bushing 101 with a tack weld 104 at the proximal end of the bushing 101. The tack weld 104 functions similarly to the tack weld 49 described in the embodiment illustrated in FIG. 3. The bushing 102 is slidably disposed within the outer tube 48, and the distal end of the slider 50 is disposed within the bushing 102 and fixed to the bushing 102 with a circumferential weld at the distal end of the slider 50. The bushing 103 is fixed to the inner surface of the outer tube 48 with a circumferential weld at the distal end of the outer tube 48, and the proximal end of the positioner tube 42 is disposed within the inner surface of the bushing 103 and fixed to the bushing 103 with a circumferential weld at the distal end of the bushing 103. Features that are identical to the other embodiments are not again identified.

When the implant interface 80 is in the engaged orientation, the slider 50 is disposed in a distal position within the outer tube 48 and temporarily held in place by the tack weld 104, as illustrated in FIG. 20A. When desired by the operator, a predetermined force is applied to the slider 50 in the proximal direction relative to the outer tube 48, and the tack weld 104 is broken to free the slider 50 to slidably move in the proximal direction within the bushing 101. The operator then moves the slider 50 into a proximal position illustrated in FIG. 20B, which corresponds to the disengaged orientation at the implant interface 80. The slider 50 is retained in the outer tube 48 by the interference between the bushing 102 and the bushing 101, thereby preventing the removal of the slider 50 from the outer tube 48. In an alternative, the bushing 102 can be replaced with a flared distal end of slider 50 having an outer diameter that is greater than the inner diameter of bushing 101. In another alternative, the bushing 101 can be replaced by a crimped proximal section of the outer tube 48 that has an inner diameter that is less than the outer diameter of the bushing 102, and the tack weld 104 can instead temporarily fix the proximal end of the outer tube 48 to the exterior of the slider 50. In yet another alternative, a crimp can be added to the outer tube 48 just distal of the bushing 101 to establish an abutting surface that will impede the proximal movement of the bushing 102.

Figure 25:
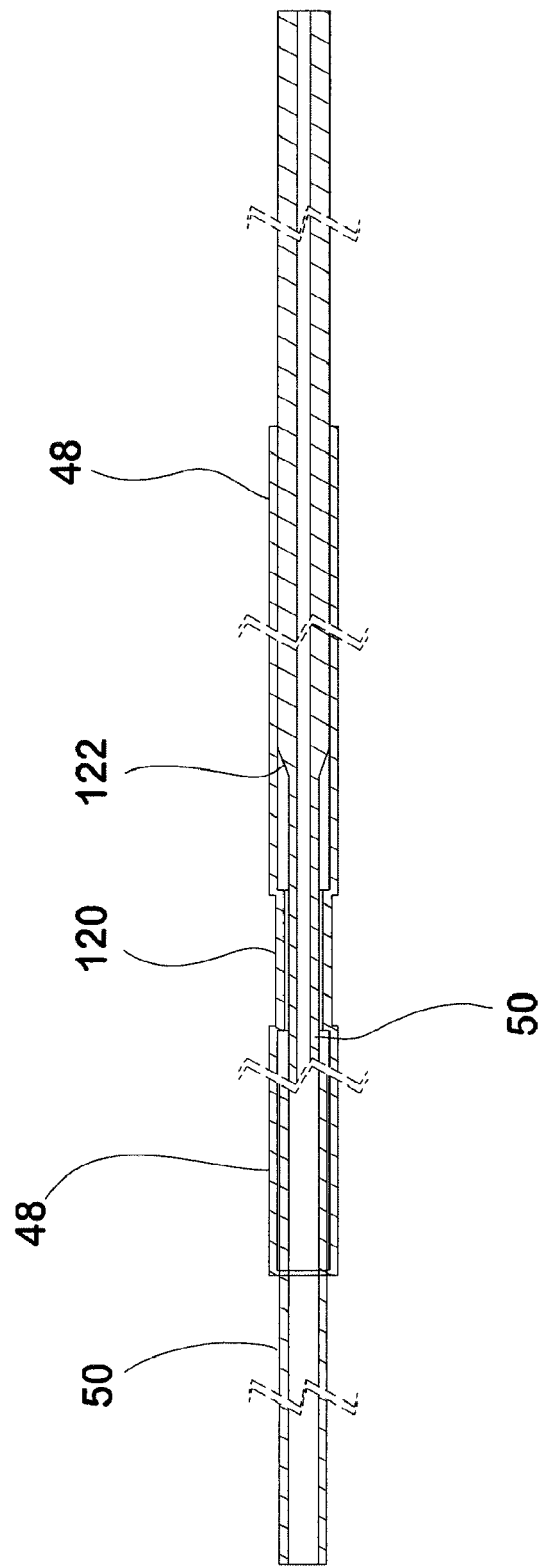
FIG. 25 is a plan cross-section view of another embodiment of the actuator interface of FIG. 3.

In yet another embodiment illustrated in FIG. 24, the outer tube 48 preferably has a crimp 120 that forms an internal surface with a diameter that is less than the outer diameter of a portion of the slider 50, so that when the slider moves in the proximal direction an edge 122 abuts the inner surface formed by the crimp 120 and stops the further proximal movement of the slider 50. As also illustrated in FIG. 24, the positioner 42 preferably includes one or more markers 124 on a sleeve 126, which are preferably fluoro-safe markers. FIG. 25 illustrates another embodiment functioning similarly to the embodiment of FIG. 24. Features that are identical to the other embodiments are not again identified in FIGS. 24 and 25.

Actuator

The actuator provides a mechanism that removably engages the actuator interface and causes the controllable and predictable movement of the actuator interface. The actuator achieves this function by providing a structure that holds the outer tube in a fixed position relative to the body of the actuator, and a pawl and anvil that pinches the slider and pulls the slider in the proximal direction for a predetermined distance with a predetermined, force, and then disengages from the slider to allow disengagement from the actuator. The actuator also provides a design that allows the operator to hold the actuator firmly in place, in order to maintain the position of the positioner relative to the target site, and allows the operator to utilize the actuator in a controlled manner that minimizes the movement of the positioner.

As illustrated in FIG. 1, the proximal end of positioner 40 preferably engages a distal end of the actuator 20. As illustrated in FIGS. 21A-22B, the actuator 20 includes a body 21, a receiver section 22, a pawl 23, an anvil 24, a slide return spring 25, a sliding frame 26, and a gripper 27. The body 21 is preferably tubular and provides support for the proximal portion 26a of the sliding frame 26, the receiver section 22, and the slide return spring 25. Enclosing part of the body 21 is the gripper 27 which has two prongs that are pulled by the operator in the proximal direction when operating the actuator 20. The gripper 27 is fixed to a pin 28 that passes radially through the gripper 27, through slot 29 in the body 21, and is fixed to the sliding frame proximal portion 26a. The sliding frame proximal portion 26a is also moveably connected to the proximal end of the body 21 by the slide return spring 25. As can be appreciated from FIGS. 21A-22B, the sliding flame 26, the gripper 27, and the pin 28 are fixed to each other and move as one when the operator grasps the two prongs of the gripper 27 and the proximal end of the body 21 and slidably moves the gripper 27 in the distal direction relative to the body 21 from the position illustrated in FIG. 21A to the position illustrated in FIG. 21B.

Figure 21A:
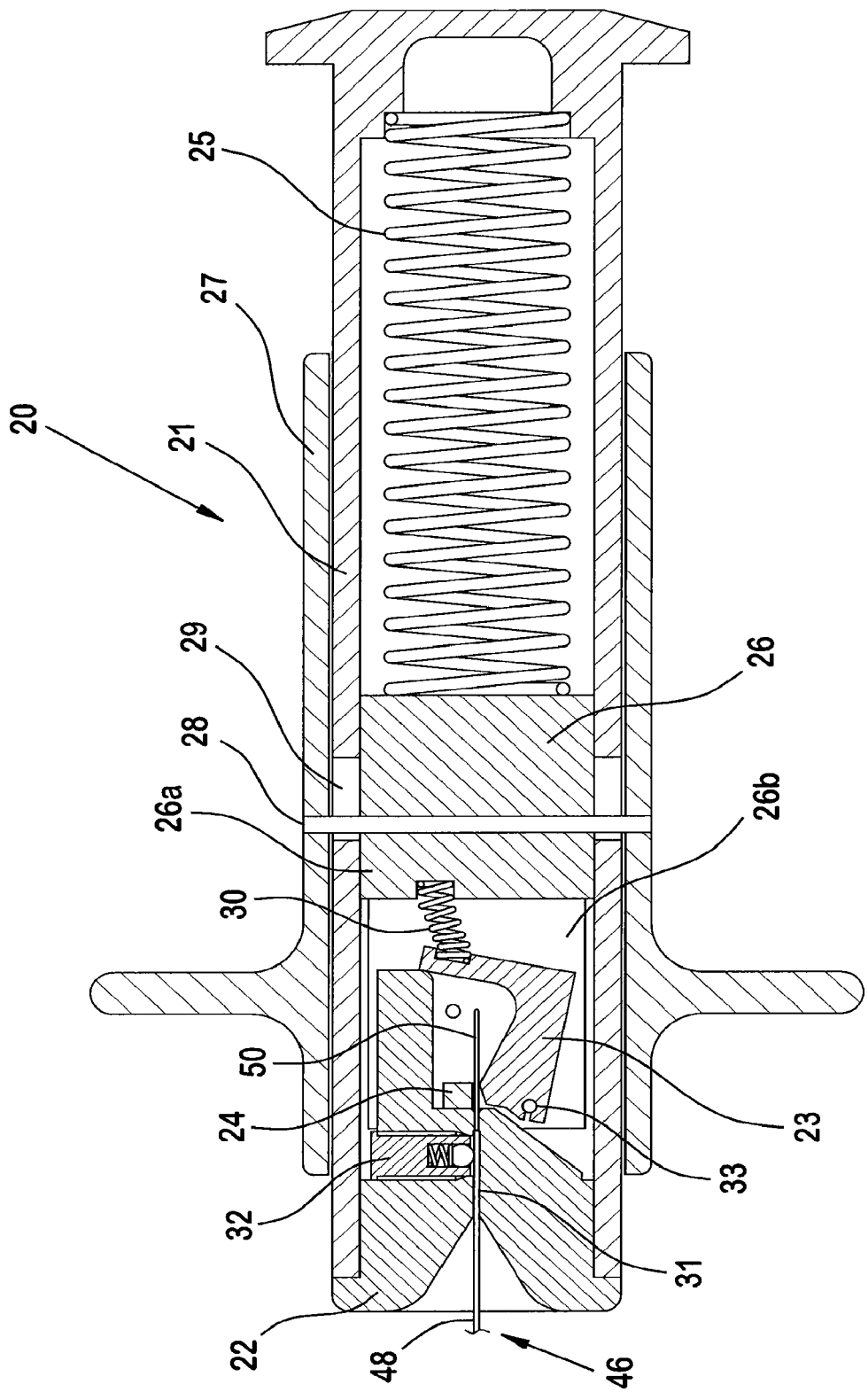
FIG. 21A is a plan partial cross-section view of the actuator of FIG. 3 in a deactivated position.
Figure 21B:
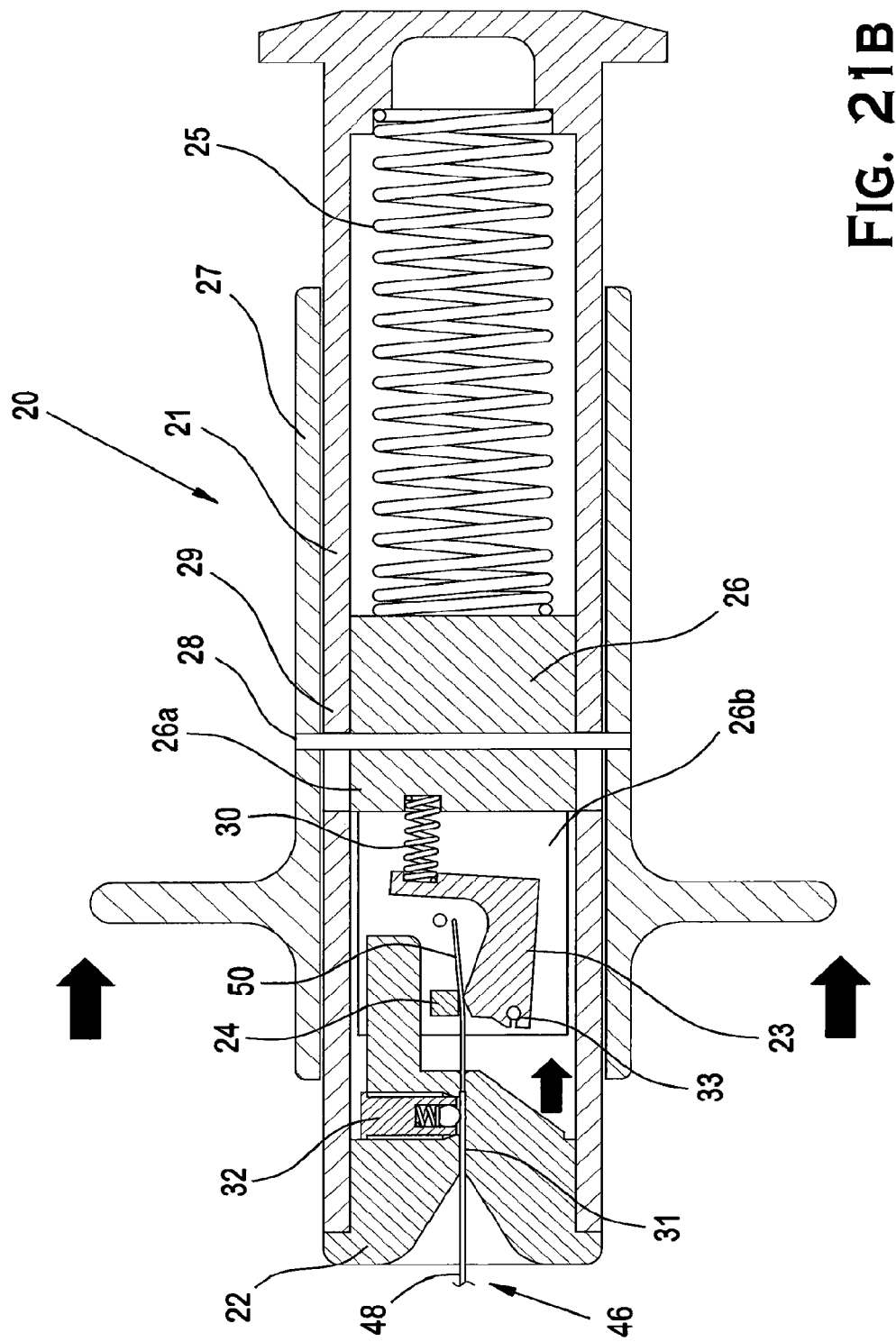
FIG. 21B is a plan partial cross-section view of the actuator of FIG. 3 in an activated position.
Figure 22A:
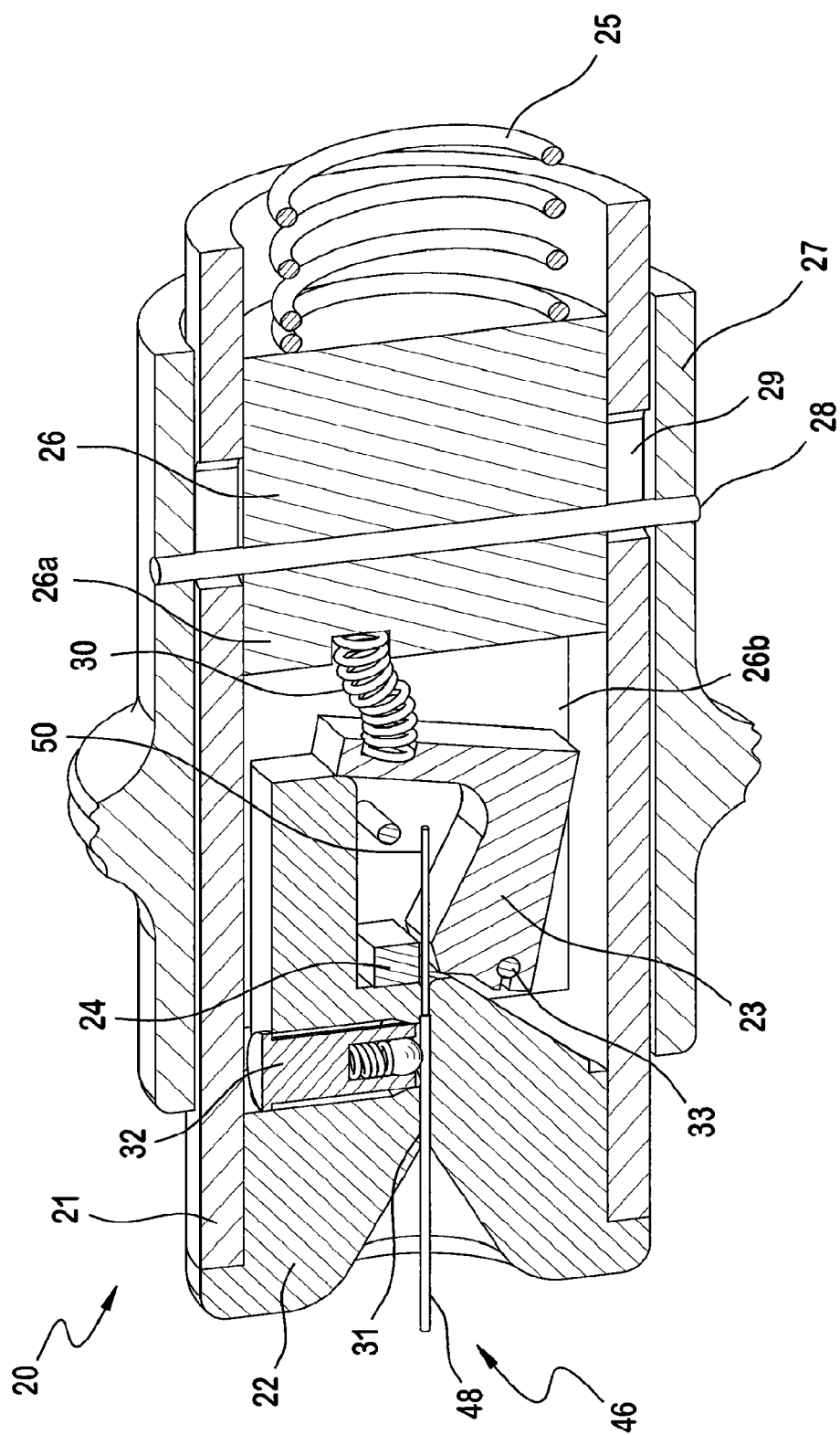
FIG. 22A is a isometric partial cross-section view of a portion of the actuator of FIG. 21A.
Figure 22B:
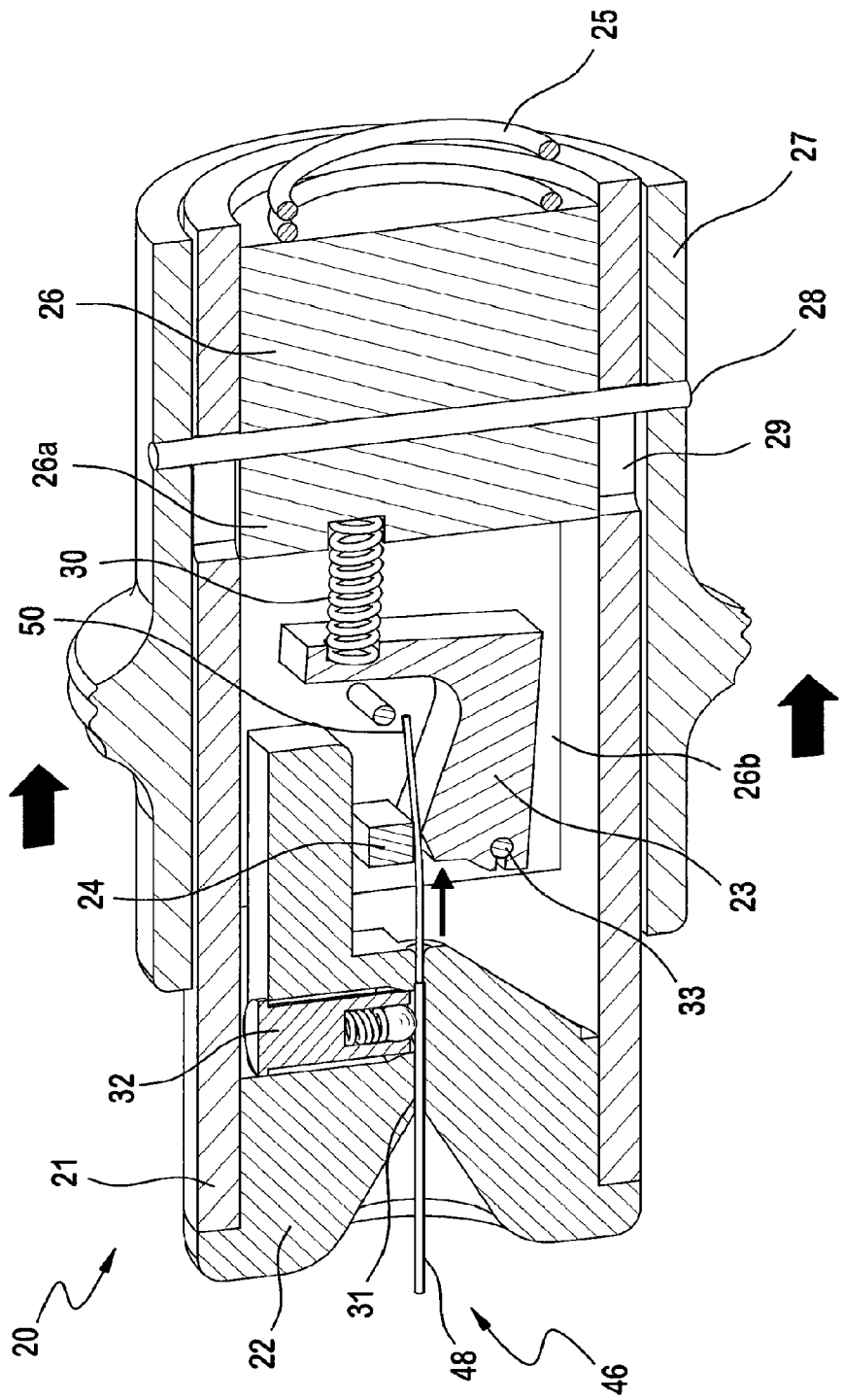
FIG. 22B is a isometric partial cross-section view of a portion of the actuator of FIG. 21B.

FIGS. 21A and 22A illustrate the actuator 20 in a deactivated position that permits insertion of the actuator interface 46 into the actuator 20. FIGS. 21B and 22B illustrate the actuator 20 in an activated position in which the slider 50 has been pulled in the proximal direction relative to the outer tube 48 to cause the implant interface 80 to move from the engaged orientation to the disengaged orientation.

As illustrated in FIGS. 21A and 22A, the body 21 is preferably tubular, and has a distal end connected to the receiver section 22, and an interior lumen slidably containing the partly-cylindrical sliding frame 26. The receiver section 22 has a distal surface that includes a funnel that directs the insertion of the actuator interface 46 into a central lumen 31. The central lumen 31 has two internal diameters adjacent to each other along the length of the central lumen 31 that correspond to the outer diameters of the slider 50 and the outer tube 48, and an edge between the two diameters that functions as a stop when abutting the proximal end of the outer tube 48. The edge of the central lumen 31 limits the proximal movement of the actuator interface 46 when inserted into the central lumen 31, and orientates the slider 50 so that it is disposed in a proximal direction from the central lumen 31 to a predetermined position between the pawl 23 and the anvil 24. The proximal end of the body 21 has an enclosed end containing the slide return spring 25 under compression. The enclosed end of the body 21 also provides a surface that the operator can hold in place when moving the prongs of the gripper 27 to change the actuator 20 from the deactivated position to the activated position. The slide return spring 25 also serves to return the actuator 20 to the deactivated position once the operator releases the prongs of the gripper 27.

The receiving section 22 also includes a detent 32 fixed in a channel directed radially into the receiving section 22 and into the central lumen 31. The detent 32 includes a ball positioned in the channel that is biased towards the central lumen 31 by an internal spring. A portion of the ball of the detent 32 is pressed into the central lumen 31 by the internal spring and, when the actuator interface 46 is inserted into the central lumen 31, the ball presses against the outer surface of the outer tube 48 and frictionally retains the outer tube 48 in the central lumen 31.

Slidably disposed in the interior of the body 21 is the sliding frame 26. The proximal portion 26a of the sliding frame 26 is sized to conform to the interior surface of the body 21, to align and guide the movement of the sliding frame 26 within the body 21. The sliding frame 26 is biased in the body 21 to move in the distal direction by the slide return spring 25. The distal portion 26b of the sliding frame 26 engages the proximal portion 26a (behind the pawl 23 and the anvil 24 in the cross-sectional views presented in FIGS. 21A-22B) and abuts the proximal surface of the receiver section 22, and provides a generally flat surface that is parallel to and adjacent to the portion of the slider 50 disposed proximal to the central lumen 31. The sliding frame distal portion 26h is composed of two opposing members that extend from the cylindrical sliding frame proximal portion 26a, with each member disposed on opposing sides of the pawl 23 and the anvil 24, to hold the pawl 23, the anvil 24, and a pawl spring 30 in position between the two opposing members. In the cross-sectional views presented in FIGS. 21A-22B, only the rear-most (of the view presented) of the two opposing members of the sliding frame distal portion 26b is illustrated.

A hinge 33 also is disposed on the flat surface of the sliding frame distal portion 26b (between the two opposing members of the sliding frame distal portion 26b) and engages the pawl 23, and the pawl spring 30 biases the proximal end of the pawl 23 away from the sliding frame proximal portion 26a rotatably around the hinge 33, and presses the proximal end of the pawl 23 against the proximal end of the receiver section 22. The anvil 24 is carried by the flat surface of the sliding frame distal portion 26b (between the two opposing members of the sliding frame distal portion 26b) and, in the deactivated position illustrated in FIGS. 21A and 22A, a space is maintained between the pawl 23 and the anvil 24 sufficient to permit the insertion of the slider 50 between the pawl 23 and the anvil 24.

Referring to FIGS. 21B and 22B, when the sliding frame 26 is moved a predetermined distance in the proximal direction relative to the body 21 and away from the receiving section 22, the pawl 23 and anvil 24 also move because they are engaged to the sliding frame distal portion 26b. The proximal movement of the sliding frame 26 also causes the proximal end of the pawl 23 to rotate around hinge 33 because of the bias from pawl spring 30, which is under compression, and causes the distal end of the pawl 23 to press the slider 50 against the anvil 24, thereby pinching and securing the slider 50. The slider 50, now secured between the pawl 23 and the anvil 24, is pulled in the proximal direction by the proximal movement of the sliding frame 26, while the outer tube 48 is retained by the edge within the central lumen 31 of the receiver section 22, thereby causing the tack weld. 49 to break and move the implant interface 80 into the disengaged orientation. As illustrated in FIGS. 21B and 22B, the slider 50 is ultimately moved in the proximal direction, relative to the outer tube 48, by almost the same distance traveled by the anvil 24 and the sliding frame 26 in the proximal direction relative to the body 21 and the receiver section 22.

More preferably, the receiver section 22 is made of polycarbonate or ABS, and the pawl 23, the anvil 24, the slide return spring 25, and the pawl spring 30 are made of steel. Also more preferably, the funnel of the receiver section 22 is a cone with an angle of 10-120 degrees, and the central lumen 31 has a diameter of 0.010-0.030 of an inch to receive the outer tube 48 and a diameter of 0.006-0.026 of an inch to receive the slider 50.

Most preferably, the receiver section 22 is made of polycarbonate, and the pawl 23, the anvil 24, the slide return spring 25, and the pawl spring 30 are made of stainless steel. Also most preferably, the funnel of the receiver section 22 is a cone with an angle of 30 degrees, and the central lumen 31 has a diameter of 0.018 of an inch to receive the outer tube 48 and a diameter of 0.014 of an inch to receive the slider 50.

Figure 27:
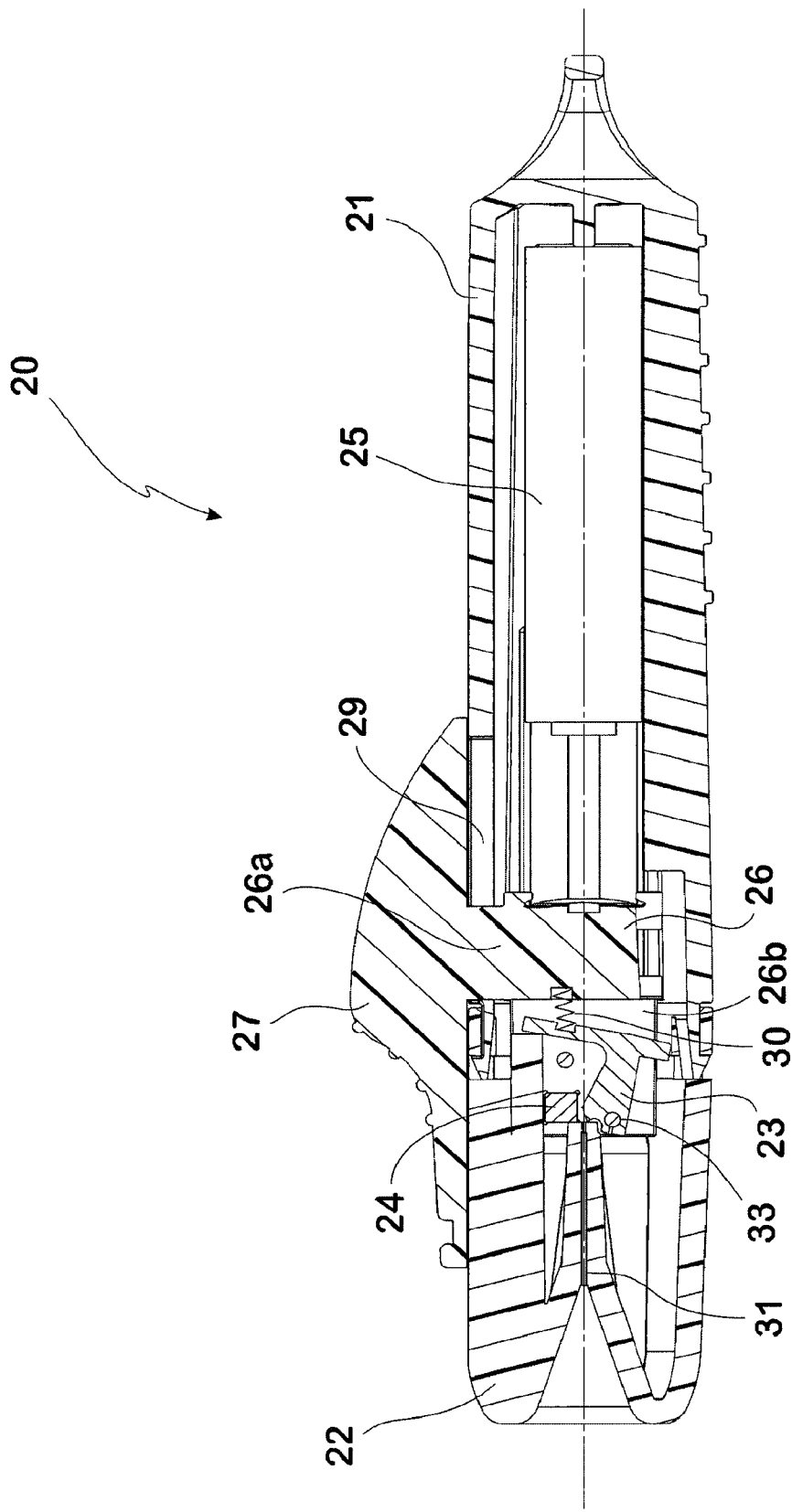
FIG. 27 is a plan partial cross-section view of another embodiment of the actuator of FIG. 3 in an activated position.

The operator-manipulated interface surface used by the operator to move the actuator 20 from the deactivated position, illustrated in FIG. 21A, to the activated position, illustrated in FIG. 21B, can be implemented with a variety of alternative designs that provide the structure necessary to move the sliding frame 26 proximally relative to the receiver section 22 (i.e., the gripper 27 and the prongs disposed on the gripper 27 can be replaced with alternative structures that can controllably move the internal components within gripper 27 as illustrated in FIGS. 21A and 22B). In the embodiment illustrated in FIG. 1, and as illustrated in FIGS. 21A-22B, the actuator 20 involves the operator compressing the actuator 20 an that the prongs of the gripper 27 (fixed to the sliding frame 26) are moved proximally in relation to the proximal end of the body 21 (fixed to the receiver section 22). In alternative embodiments, instead of the operator compressing the actuator 20 with the gripper 27, the internal components (i.e., the components within gripper 27) of the actuator 20 remain essentially the same, but the external components interfacing with the operator are adapted to facilitate a variety of actuating motions, such as the actuating motions of squeezing a trigger, sliding a switch, turning a wheel, pushing a button, or moving a lever. Another embodiment of the actuator 20 is illustrated in FIGS. 27 and 28, with features identical to the other embodiments not identified again. As illustrated in FIG. 27, the body 21 is held by the operator and the gripper 27 is slid in the proximal direction to move the actuator 20 from the deactivated position to the activated position illustrated in FIG. 27.

Pushability

The vasculature of the brain is more tortuous than the vasculature leading to the brain from the groin, a typical access point into a patient's body. An instrument disposed in a patient's body between the groin and the brain thus experiences the most tortuous pathway at the distal end of the instrument. This tortuous pathway forces the instrument to bend and subjects the instrument body to increased stresses. Also, any sliding member slidably moved within the instrument, such as a cord, is subjected to greater frictional forces against the sides of the instrument when the instrument is bent or curved. These increased frictional forces require the operator of the instrument to exert additional force to move the sliding member through the instrument, and the increased stresses on the instrument from bends or curves can cause permanent deformation of the instrument or failure of the instrument body or sliding member. Also, high frictional forces at the distal end of the instrument body can impede the movement of the instrument through a catheter, or the movement of a cord through the instrument. Namely, high frictional forces at the distal end of the instrument can cause the middle and proximal portions of the sliding member or cord to buckle, i.e., to have the axial movement of the sliding member or cord redirected in a undesirable non-axial or radial direction instead of a desired axial direction, or form kinks in the sliding member or cord.

In order to minimize the force required from the operator, and to lessen the potential for failure of instrument components, the positioning system advantageously achieves improved "pushability." Specifically, pushability can be characterized by a ratio of the force applied to the positioner or cord by the operator at the proximal end of the system ("F1") and the force observed at the distal end of the system ("F2"). Ideally, when the ratio of F1 to F2 approaches unity, this indicates that the force applied to the proximal end translates to an equal or near equal force at the distal end. As can be appreciated, buckling or kinking of the positioner or cord would produce a ratio of F1 to F2 that is not at or not near unity. The ratio of F1 to F2 can also be represented as a percentage, indicating that a certain percentage of the force at the proximal end was observed at the distal end. As shown in Table 1, the positioning system 10 preferably provides a pushability that is nearer to unity (100%) than that observed with an existing delivery system ("Nexus/NXT Pusher" refers to a pusher used with the Nexus™ and NXT™ coils, commercially available from EV3, Inc. of Plymouth, Minn. USA).

TABLE 1

| Sample System | Average pushability | Standard deviation |
| --- | --- | --- |
| Positioning system | 94.6% | 1.9% |
| Nexus/NXT Pusher | 79% | 4.6% |

The positioning system also advantageously achieves improved "pushability" or "slidability" by reducing friction between the cord 52 and the positioner tube 42, and between the positioner tube 42 and the microcatheter 14. The following equation is a characterization of the frictional forces relating to a flexible inner cylindrical member enclosed within a flexible outer cylindrical member, with the outer member conforming to a curved surface defining a tortuous path, and with the inner member slidably moved within the outer member:

$$F_1/F_2 = e^{\mu \Theta} \quad \text{Equation (3)}$$

where,
- $F_1$ is the force applied to the inner member at a proximal end of the interface between the inner and outer tubes over the length of the tortuous path,
- $F_2$ is the resisting force exerted by the outer member at a distal end of the interface between the inner and outer tubes over the length of the tortuous path,
- e is the base of natural logarithms,
- $\mu$ is the average coefficient of friction along the length of the interface between the inner and outer tubes over the length of the tortuous path, and
- $\Theta$ is total tortuosity over the length of the tortuous path, i.e., the sum of angular contact between the inner member and the outer member, in radians.

The smallest force transfer ratio ($F_1/F_2$) possible is desired so that there is only a small frictional loss related to the movement between the inner and outer tubes. As it is well known that $e^0 = 1$, it can be appreciated that, in order for the force transfer ratio to be as small as possible, the product of $\mu$ and $\Theta$ must likewise be a small value.

When the principles of Equation (3) and knowledge of vasculature anatomy are applied in the various embodiments, an advantageous force transfer ratio is achieved by reducing the average friction coefficient at the portions of the positioning system 10 subject to the greatest tortuosity. This is achieved by preferably selecting specific materials and surface characteristics of mating surfaces at the portions of the positioning system 10 subject to the greatest tortuosity, preferably in the distal-most third of the positioner 40. More preferably, the positioning system 10 performs within a range of tortuosity of 900-4000 degrees, with a three transfer ratio of 16 or less, and an average friction coefficient of 0.045 or less over the length of the 4000-degree tortuous path. Most preferably, the positioning system 10 performs within a range of tortuosity of 2000-4000 degrees, with a force transfer ratio of 16 or less, and an average friction coefficient of 0.045 or less over the length of the 4000-degree tortuous path.

Materials capable of providing a friction coefficient of 0.045 or less are limited. Preferably, the cord 52 is a stainless steel cord with a roughness of less than 50 microinches and the cord liner 68 is a polymer with a roughness of less than 200 microinches, the cord liner 68 and the cord 52 has a hydrophilic coating, or the space between the cord liner 68 and the cord 52 is loaded with a liquid polysiloxane containing a concentration of stearic acid in the range of 2-10%. More preferably, the cord 52 is a 304 stainless steel cord with a roughness of less than 50 microinches and the cord liner 68 is PTFE with a roughness of less than 200 microinches.

Preferably, the materials for the cord 52 and the cord liner 68 are used for the entire lengths of the cord and cord liner. However, the preferred materials need only be provided in the portions of the positioner 40 that are subjected to the 4000 degrees of tortuosity, which is mostly the distal third of the positioner 40. For the proximal two thirds of the positioner 40, a wider selection of materials is available because this portion of the positioner 40 is subjected to less tortuosity (less than 2000 degrees) than the distal third of the positioner 40. Preferably, for the proximal two thirds of the positioner 40, the positioner 40 performs with a force transfer ratio of 15 or less and an average friction coefficient of 0.11 or less over the length of a 2000 or less-degree tortuous path in the proximal two thirds of the positioner 40. The materials capable of providing a friction coefficient of 0.11 or less are not as limited as with the distal third of the positioner 40. Preferable materials suitable for use in the proximal two thirds of the positioner 40 include polyethylene, acetal, or fluoropolymer for the cord liner 68, and a steel or polymer material with a surface roughness of less than 50 microinches for the cord 52. More preferably materials are polyethylene for the cord liner 68 and steel with a surface roughness of less than 50 microinches for the cord 52.

An advantageous force transfer ratio is also achieved at another mating surface of the positioning system 10, where the positioner tube sleeve 66 slidably moves within the microcatheter 14. Applying the same principles of Equation (3) as described above for the cord 52 and the cord liner 68, the preferred material for the positioner tube sleeve 66 is a PTFE heat shrunk material and the preferred material for the microcatheter 14 is a polymer with a relatively smoother surface.

Flexibility

The flexibility of the positioning system along the length of the system can affect system design and performance, as the flexibility of the system relates to the ability of the operator to control the positioner and the "feel" of the system from the proximal end manipulated by the operator. Also, the suppleness of the distal tip of the positioner relates to the ability of the operator to direct the positioner into the desired position. Maintaining the desired flexibility of a system with a mechanical implant engagement and disengagement system is particularly difficult because the length of the system must provide a mechanical connection between the proximal and distal ends of the system that is both small in size but strong enough to cause the engagement and disengagement of the implant from the system.

The positioning system achieves the appropriate level of flexibility by preferably providing a relatively rigid structure at the proximal portion of the positioner, a relatively supple structure at the distal portion the positioner, and a transition region in the middle of the positioner that provides a change in flexibility between the proximal and distal portions. The proximal portion of the positioner preferably provides a flexibility (or stiffness) that remains almost constant along the length of this section of the positioner. The near-constant flexibility of the proximal portion is achieved by the use of a tube structure. The distal portion and the transition region achieve a suppleness with a combination of structural modifications to the tube structure that increases flexibility, the increase in the degree of those structural modifications along the length of the tube structure in the distal direction, and the structural support provided, to the positioner by reinforcing structures. The flexibility of the distal portion increases along the length of this section, with the greatest suppleness achieved near or at the distal-most end of the positioner. More preferably, the near-constant flexibility of the proximal portion is achieved by a fully-enclosed tube structure of the positioner without the use of skiving. The variable flexibility characteristics of the distal portion and the transition region are achieved by a combination of a tube with skiving, the increase in the degree of the skiving along the length of the tube in the distal direction, and the structural support provided to the positioner by the positioner tube sleeve.

Figure 23A:
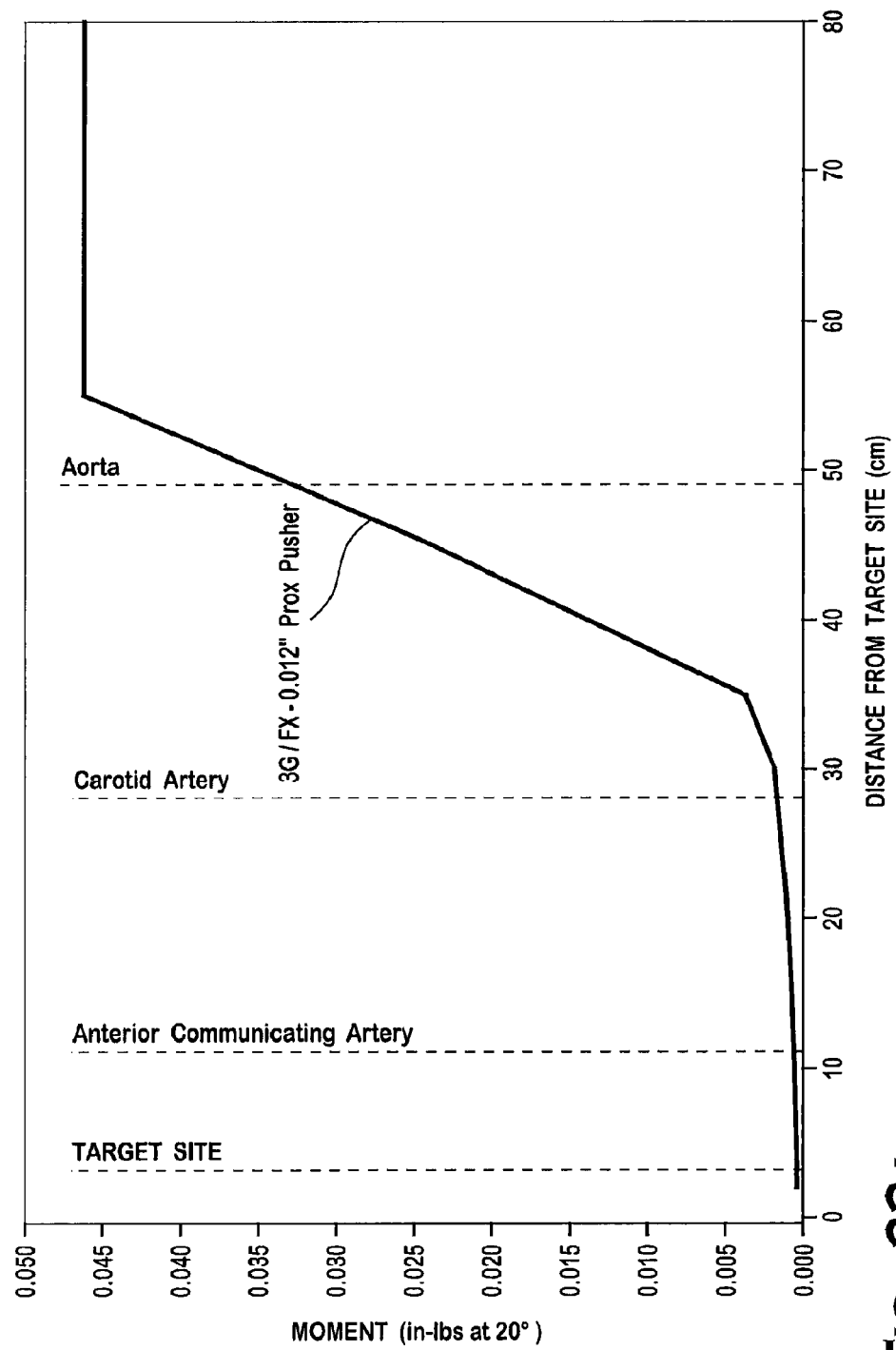
FIGS. 23A-23C illustrate flexibility profiles fir existing systems and the positioner illustrated in FIGS. 3 and 4.
Figure 23B:
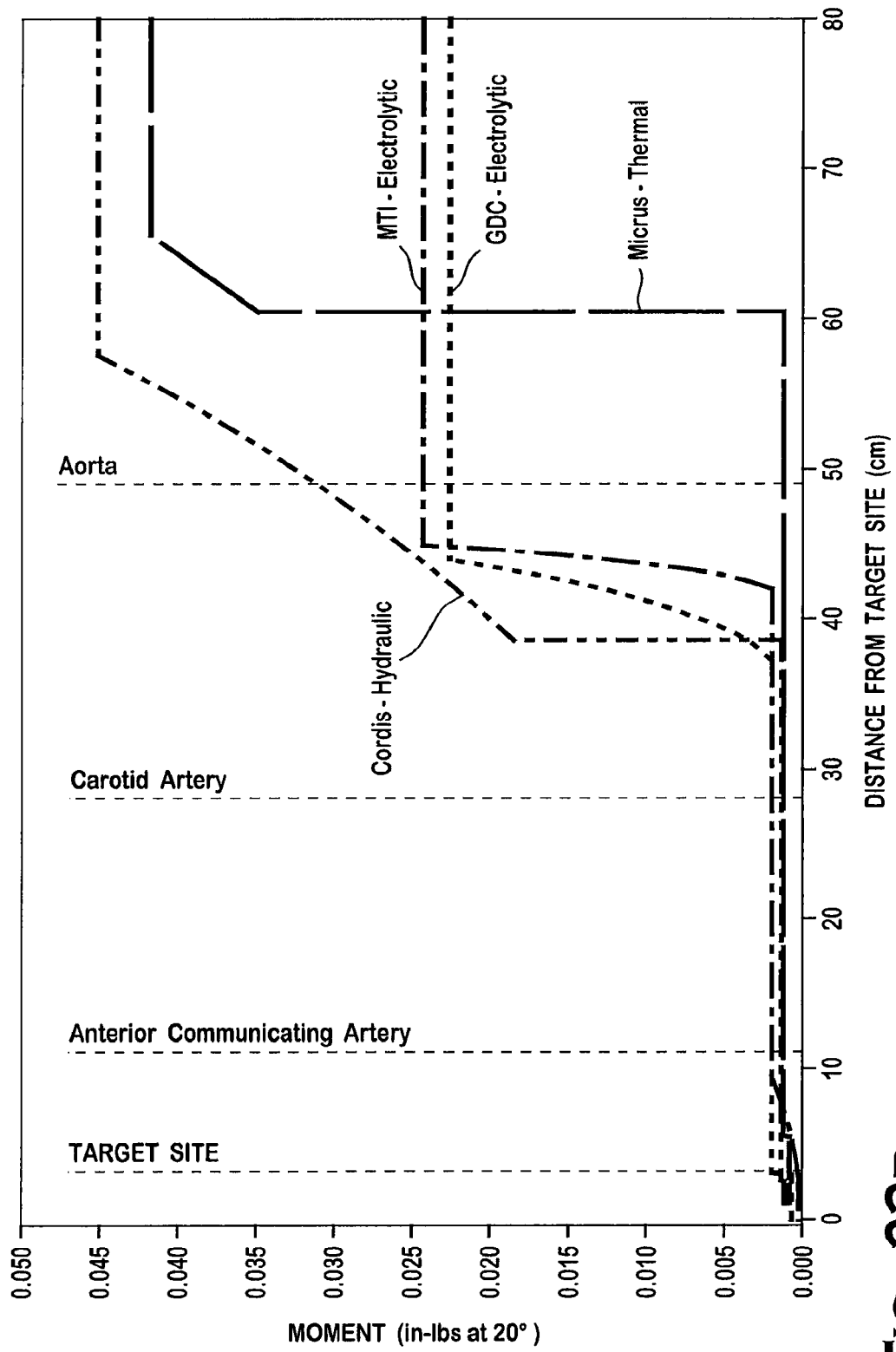
Figure 23C:
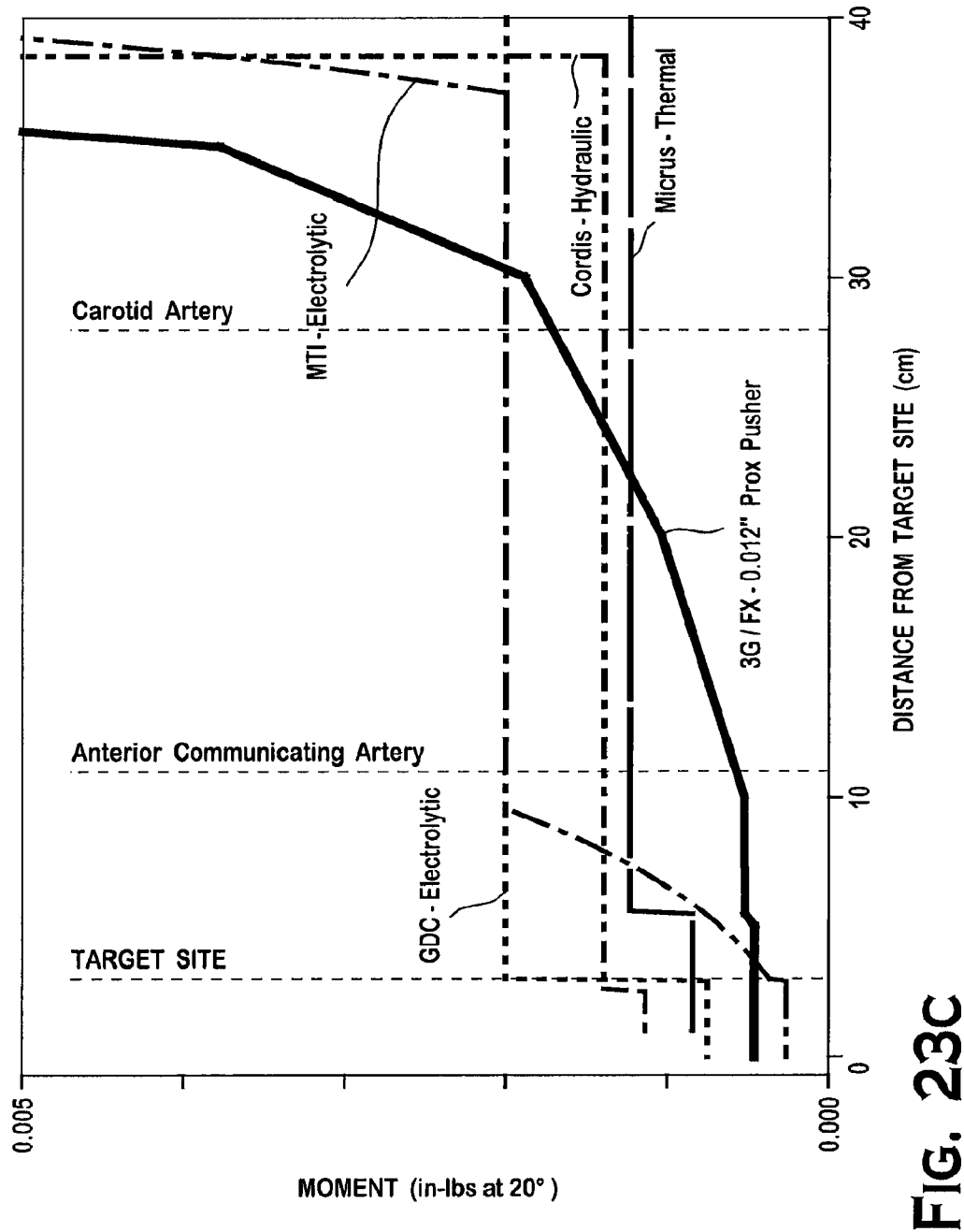

FIG. 23A illustrates the flexibility of the positioner 40 of the embodiment illustrated in FIGS. 3 and 4 (identified as "3G/FX—0.012" Prox Pusher" in FIGS. 23A and 23C). The horizontal axis in FIG. 23A (labeled "distance from target site") corresponds to the length of the positioner 40, with the end cap 82 (proximate to or within the area of the target site, as illustrated in FIG. 2C) defining the zero point on the horizontal axis and each marking on the horizontal axis identifying a distance from the end cap 82 in the proximal direction. The horizontal axis also corresponds to the anatomical areas in the human body illustrated in FIG. 2A when the end cap 82 is disposed near the target site 16, with distances proximal from the end cap 82 and target site 16 corresponding to the various anatomical features identified in FIG. 23A until the proximal end of the positioner 40 ultimately exits the human body at the groin as illustrated in FIG. 2A. The vertical axis in FIG. 23A (labeled "moment") corresponds to the amount of resistance provided by the positioner 40 along its length when subjected to a 20° deflection.

When subjected to a 20° deflection, the positioner 40 resists the deflection, which corresponds to flexibility, by generating a moment. As illustrated in FIG. 23A, the moment observed at the proximal portion of the positioner 40 is approximately constant proximal to the portion of the positioner 40 disposed near the aorta, indicating a near-constant flexibility in this portion of the positioner 40. The moment observed at the distal portion of the positioner 40 decreases distal to the portion of the positioner 40 disposed in the carotid artery, indicating a variable flexibility in this portion of the positioner 40 that increases in the distal direction. As also illustrated in FIG. 23A, the moment changes at an approximately linear rate in the transition region of the positioner 40 that corresponds to a length of the positioner 40 disposed between the aorta (approximately) and carotid artery (approximately), indicating an approximate linear change in flexibility in this portion of the positioner 40, from a lesser flexibility to a greater flexibility in the distal direction. The near-constant flexibility in the proximal portion of the positioner 40, and the approximately linear change in positioner flexibility in the transition region, provides a combined flexibility that is interpreted as a good "feel" to the operator manipulating the outer tube 48. The flexibility profile illustrated in FIG. 23A also advantageously provides a relatively supple distal end in the tortuous anatomy within the brain and distal to the carotid artery. The relatively stiff proximal end provides the operator the ability to control the positioner 40. Also, the portion of the positioner 40 where the greatest transition from rigid to supple takes place (in the transition region) is disposed as distal as possible in the positioner 40, but just proximal of the carotid artery where the anatomy begins to become more tortuous towards the brain and where increased suppleness is desired.

As also illustrated in FIG. 23A, the positioner 40 provides a variable flexibility profile over the length of the positioner 40. At the proximal portion of the positioner 40, the moment measured preferably is 0.01-0.50 in-lbs at 20° of deflection between the proximal end of the positioner 40 and the portion of the positioner 40 disposed near the aorta, between 55 cm and 80 cm proximally from the target site 16. At the distal portion of the positioner 40, the moment measured preferably is 0.0001-0.0100 in-lbs 20° of deflection between the portion of the positioner 40 disposed in the carotid artery and the end cap 82, between 0 cm and 35 cm proximally from the target site 16. At the transition region of the positioner 40 between the proximal and distal portions, the moment measured preferably changes from 0.001 in-lbs to 0.100 in-lbs at 20° of deflection between 35 cm and 50 cm from the target site 16. More preferably, the flexibility of the proximal portion is approximately 0.045 in-lbs at 20° of deflection, the flexibility of the transition region changes form 0.0005 to 0.045 in-lbs at 20° of deflection, and the flexibility of the distal portion is approximately 0.0005 in-lbs 20° of deflection.

As further illustrated in FIG. 23A, the flexibility of the positioner 40 changes at specific rates over the length of the positioner 40, as determined from the measurement of moment in the positioner 40. At the proximal portion of the positioner 40, the flexibility preferably does not change between the proximal end of the positioner 40 and the portion of the positioner 40 disposed near the aorta, between 55 cm and 80 cm proximally from the target site 16. At the distal portion of the positioner 40, the flexibility preferably changes at a rate of 100-800% between the portion of the positioner 40 disposed in the carotid artery and the end cap 82, between 0 cm and 35 cm proximally from the target site 16. At the transition region of the positioner 40 between the proximal and distal portions, the flexibility preferably changes at a rate of 100-1000% between 35 cm and 55 cm from the target site 16. More preferably, the flexibility of the proximal portion is constant, the flexibility of the transition region changes at a rate of approximately 800%, and the flexibility of the distal portion changes at a rate of approximately 700%.

As illustrated in FIG. 23B, the flexibility profiles of existing thermal, electrolytic, and hydraulic systems are comparable to the flexibility profile of the embodiment illustrated in FIGS. 3 and 4 (In FIGS. 23B and 23C, "Cordis" refers to Cordis Corporation of Miami Lakes, Fla. USA, "MTI" refers to Micro Therapeutics, Inc. of Irvine, Calif. USA, "GDC" refers to the Gugliehni Detachable Coil or GDCID® Detachable Coil commercially available from Boston Scientific Corporation of Natick, Mass., USA, and "Micrus" refers to Micrus Endovascular Corporation of San Jose, Calif. USA). As can also be appreciated from a comparison of FIGS. 23A and 23B, the illustrated embodiment has a less flexible proximal portion, between the proximal end of the positioner 40 and the portion of the positioner disposed near the aorta, than existing thermal, electrolytic, and hydraulic systems.

FIG. 23C is a closer and more detailed view of the information presented in FIGS. 23A and 23B, between the distances of 0 and 40 cm (on the x-axis) and between the moments of 0.000 and 0.005 in-lbs (on the y-axis). As can be seen in FIG. 23C, in the distal portion of the positioner 40, between 0 and 35 cm from the end cap 82 (or from the distal ends of the respective existing systems), the moment observed decreases (and the flexibility of the positioner 40 increases) continuously until reaching the last 4 cm, where measurements become less reliable. As can also be seen in FIG. 23C, the existing non-mechanical systems of FIG. 23B produce a moment that does not change between 10 and 35 cm and that quickly reduces to a minimal moment between 0 and 10 cm. It is believed that this comparatively abrupt change in moment in the distal-most 10 cm of existing devices demonstrates that existing devices do not have continuously varying flexibility in their respective distal portions. The positioner 40 of the illustrated embodiment, however, has a flexibility that changes continuously along the length of the distal portion, and especially between the 5-35 cm proximal to the end cap 82. As can also be seen from FIG. 23C, the distal end of the positioner 40 provides a flexibility that changes in the distal direction by 100-800% between 35 cm and 0 cm from the end cap 82, and more preferably changes by approximately 700%. As can also be seen from FIG. 23C, the distal end of the positioner 40 provides a flexibility that changes in the distal direction between 35 cm and 10 cm from the end cap 82, decreasing by 100-900%, and more preferably by 500%. Referring to FIG. 23C, it is believed that existing non-mechanical systems do not provide distal portions with flexibilities that change as significantly as seen with the positioner 40, and it is also believed that existing non-mechanical systems do not provide distal portions with flexibilities that change between 10 and 35 cm from the distal-most end of these systems.

The flexibility of the tip of the positioner 40 is important to proper positioning of the implant 90 at the target site 16. The distal tip flexibility of the embodiment illustrated in FIGS. 3 and 4 has been demonstrated to provide a more flexible tip as compared to other systems when subjected to a longitudinally compressive three, as shown in Table 2.

TABLE 2

| Sample System | Buckling Force |
|---|---|
| Positioning system | 1.0 g |
| Micrus Pusher | 3.0 g |

Profile

A mechanically-operated positioning system must be flexible and small enough to reach the target site, but remain strong enough to permit the operator to control the positioning and mechanical operation of the implant interface. The positioning system achieves a mechanically-operated implant engagement and disengagement system with an appropriate profile, or size, by utilizing materials and surfaces with variable friction coefficients, strengths, and flexibilities appropriate for a positioner subjected to a tortuous pathway. Preferably, the outer diameter of the distal end of the positioner 40, at the distal end of the pusher tube 42, is small enough to reach the target site 16 while permitting the proper operation of the implant interface 80 from a mechanical system connecting the implant interface 80 to the proximal end of the positioning system 10. More preferably, the outer diameter of the distal end of the positioner 40, at the distal end of the pusher tube 42, has a 0.008-0.018 inch outer diameter, for 304 stainless steel hypotube or steel alloy. Most preferably, the outer diameter of the distal end of the positioner 40, at the distal end of the pusher tube 42, has a 0.012 inch outer diameter, for 304 stainless steel hypotube.

Fatigue Resistance

When implanting multiple neurological coils in an aneurysm, it is believed that a common practice is to place multiple coils within the aneurysm sufficient to occupy the void created by the aneurysm and to promote the formation of thrombi. It is also believed that a satisfactory result can be achieved when an aneurysm accommodates as many coils as possible, within the discretion of the operator. However, in such a procedure, it is possible that the coil or coils implanted first can interfere with or impeded the placement of subsequent coils. Also, this interference from already-implanted coils can possibly make it difficult for the operator to determine whether the aneurysm can accommodate additional coils. The placement of too few coils can possibly affect performance, and the placement of too many coils could possibly result in the rupture of the aneurysm or the dislodgement of a coil from a desired position at the target site.

It is further believed that when positioning an additional coil at the target site, the operator may repeatedly move the additional coil back and forth (by moving the delivery system) in order to nest the coil within the aneurysm between the already-implant coils, and to evaluate whether the aneurysm can accommodate the implantation of more coils. It is also believed that the repeated movement of the delivery system and additional coil causes the system and coil to experience friction where the system and coil slidably move within a delivery catheter and where the additional coil contacts already-implanted coils. It is believed that the friction from the repeated movement of the system and coil can cause the connection point between the system and coil to experience significant stresses and, when combined with the repeated back-and-forth movement, possibly cause material fatigue and the fracture of the connection point, resulting in the premature disengagement of the coil from the system. It is further believed that existing delivery systems that rigidly or firmly engage the additional coil, or that impede the free movement or rotation of the coil relative to the system, permit the development of the stresses relating to the repeated back-and-forth movement of the system and coil.

The positioner of the various embodiments avoids or minimizes the development of stresses at the interface between the positioner and implant by permitting the unrestrained movement of the implant relative to the positioner, within the limitations defined by the implant interface. The development of implant interface stresses is minimized or avoided because the ball, rod, and implant are able to move in the axial and radial directions compared to the axis of the positioning system, to rotate about an axis of the rod or implant, and to move angularly so that implant is at an angle as compared to the axis of the positioning system.

Referring to FIG. 13, when subjected to a back-and-forth (or push-pull) movement during an implantation procedure, a proximal movement (or pull) of the positioner 40 causes the implant interface 80 to engage and pull the ball 96 and pull the implant 90 in a proximal direction, which may cause stresses at the ball 96 and rod 94 when the implant 90 resists the proximally-directed movement because of friction from contact with the inside of the microcatheter 14 or with already-implanted implants. However, because the ball 96 and rod 94 are able to move within the end cap 82, the implant 90 is able to assume an orientation, angulation, or rotational position that prevents or minimizes the development of stresses from the bending or turning of the implant 90 relative to the positioner 40.

Referring to FIG. 12, a distal movement (or push) of the positioner 40 causes the distal surface of the implant interface 80 (the end cap 82) to engage and push the proximal surface of the implant 90 and push the implant 90 itself in the distal direction, without applying axially directed forces to the ball 96 or rod 94. The ball 96 and rod 94 are thus not subjected to a significant stress when the implant 90 is moved in the distal direction because all or a majority of the force imparted from the positioner 40 to the implant 90 is imparted directly to the implant 90 without the involvement of the ball 96 or rod 94, although there may be some radially directed forces applied to the ball 96 or rod 94 by contact with the end cap 82 or positioner 40. In the distal movement of the positioner 40 and implant 90, the implant 90 remains capable of assuming an orientation or rotational position responsive to forces resulting from the contact of the implant 90 with the end cap 82, with the inside of the microcatheter 14, or with already-implanted implants. Also, because the implant 90 abuts the end cap 82, the operator is provided with a tactile sensation regarding the degree of resistance resulting from attempts to insert or nest the implant 90 within the aneurysm or among the already-implanted implants.

As shown in Table 3, when measured, it has been observed that the engagement between the rod 94 and the positioner 40 can withstand greater tensile force than the interfaces between the implants connected to existing systems ("Positioner/Implant Interface" refers to the described embodiment, "Sapphire/NXT/Nexus" refer to the Sapphire™, NXT™, and Nexus™ products commercially available from EV3, Inc, of Plymouth, Minn. USA, and "GDC" refers to the Guglielmi Detachable Coil or GDC® Detachable Coil commercially available from Boston Scientific Corporation of Natick, Mass., USA),

TABLE 3

| System | Positioner/Implant Interface | Sapphire/NXT/ Nexus | GDC - Electrolytic |
| --- | --- | --- | --- |
| mean force | 1.71N | 1.62N | 1.02N |
| standard deviation | 0.06N | 0.18N | 0.17N |
| 95/95 | 1.53N | 0.95N | 0.38N |

Detachment Time

The embodiment illustrated in at least FIGS. 3 and 4 provides a coil positioning system 10 that are preferably already in the engaged orientation when removed from packaging and prior to insertion into a patient, as illustrated in FIG. 8A for example. The illustrated positioner 40 and implant 90 thus provide a system that is ready for use out of the package, subject of course to the requisite steps common to such medical procedures that must be performed before deploying the coil, e.g., the insertion of a microcatheter into the patient and the insertion of the delivery system into the microcatheter.

The embodiment illustrated in at least FIGS. 3 and 4 also provides a coil positioning system that directly connects the actuation of the detachment mechanism with the detachment of the implant from the delivery system, without an intermediary process that must initiate and complete to achieve coil detachment. As illustrated in FIGS. 3-4 and 8A-8C, the direct connection between slide 50 and cord 52 causes the movement of the slider 50 to move the cord 52 away from the port 84, thereby achieving a detached status because the implant 90 is no longer securely retained by the positioner 40, as the ball 96 is free to pass through port 84. Also, the coil structure of the illustrated implant 90 further facilitates the movement of the ball 96 through port 84 because the coil structure expands or adjusts to the anatomy of the target site 16, which causes the implant 90 to move distally away from the end cap 82 and thereby facilitate the movement of the ball 96 through the port 84. Preferably, the illustrated embodiment achieves an out-of-package preparatory time of approximately 15 seconds and a detachment time of less than 1 second.

It is believed that preparatory and detachment times of the illustrated embodiment provide a system that permits a fast and efficient deployment of implants at a target site. The advantageous preparatory and detachment times reduce the length of time required to prepare the positioning system and advantageously increases the efficiency of the procedure, thereby allowing the practitioner to attend to other duties during the invasive medical procedure.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An assembly for deploying an implant into an aneurysm in a vessel, comprising:
    a tubular member having a longitudinal axis, a wall defining a lumen along the axis, and a distal portion having an inner cross-sectional dimension and a distal end;
    a core wire extending within the lumen;
    a coil implant comprising:
        (i) a coil having an enlarged proximal end, a proximal portion, and a distal portion;
        (ii) a stretch-resistant member extending through the coil and having a proximal end and a distal end, the stretch-resistant member distal end coupled to the coil distal portion;
        (iii) an attachment member disposed at the proximal end of the stretch-resistant member and otherwise free of the proximal portion of the coil; the attachment member being disposed within the lumen, such that the coil implant, while the attachment member is in contact with the core wire at a point within the lumen proximal to the distal portion, is configured to (i) move axially relative to the tubular member a distance of at least a length of the attachment member and (ii) tilt about the attachment member, by rotation of the attachment member, within a range of angles relative to the longitudinal axis, wherein the inner cross-sectional dimension of the distal portion less a cross-sectional dimension of a distalmost portion of the core wire is less than a cross-sectional dimension of the attachment member, such that the attachment member is retained, by the core wire, within the lumen while the core wire is proximally retracted beyond the attachment member within the lumen.

2. The assembly of claim 1, wherein a length of a line segment extending from an outer surface of the attachment member, through the point, and to an outer surface of the core wire is greater than the inner cross-sectional dimension, such that the attachment member is prevented from moving within the lumen distally entirely past the tubular member distal end when the core wire and attachment member are positioned radially adjacent each other within the lumen.

3. The assembly of claim 2, wherein the coil implant is configured to rotate about the longitudinal axis while the core wire is contacting the attachment member at the point.

4. The assembly of claim 1, wherein the proximal portion of the coil is spaced apart from the tubular member distal portion.

5. The assembly of claim 1, wherein the coil implant is configured to rotate about the longitudinal axis.

6. The assembly of claim 1, wherein the range of angles is 10 to 50 degrees.

7. The assembly of claim 1, wherein the coil is disposed entirely outside the lumen.

8. An assembly for deploying an implant into an aneurysm in a vessel, comprising:
    a tubular member having a longitudinal axis, a wall defining a lumen along the axis, and a distal portion having the inner cross-sectional dimension and a distal end;
    a core wire extending within the lumen;
    a coil implant comprising:
        (i) a coil having an enlarged proximal end, a proximal portion, and a distal portion;
        (ii) a stretch-resistant member extending through the coil and having a proximal end and a distal end, the stretch-resistant member distal end coupled to the coil distal portion;
        (iii) an attachment member disposed at the proximal end of the stretch-resistant member and otherwise free of the proximal portion of the coil; the attachment member being disposed within the lumen, such that the coil implant, while the attachment member is in contact with the core wire at a point within the lumen proximal to the distal portion, is configured to tilt about the attachment member, by rotation of the attachment member, within a range of angles relative to the longitudinal axis, wherein the inner cross-sectional dimension of the distal portion less a cross-sectional dimension of a distalmost portion of the core wire is less than a cross-sectional dimension of the attachment member, such that the attachment member is retained, by the core wire, within the lumen while the core wire is proximally refracted beyond the attachment member within the lumen.

9. The assembly of claim 8, wherein a length of a line segment extending from an outer surface of the attachment member, through the point, and to an outer surface of the core wire is greater than the inner cross-sectional dimension, such that the attachment member is prevented from moving within the lumen distally entirely past the tubular member distal end when the core wire and attachment member are positioned radially adjacent each other within the lumen.

10. The assembly of claim 9, wherein the coil implant is configured to rotate about the longitudinal axis while the core wire is contacting the attachment member at the point.

11. The assembly of claim 9, wherein the coil implant is configured to axially move relative to the tubular member the distance of at least the length of the attachment member while the core wire is contacting the attachment member at the point.

12. The assembly of claim 8, wherein the proximal portion of the coil is spaced apart from the tubular member distal portion.

13. The assembly of claim 8, wherein the coil implant is configured to rotate about the longitudinal axis.

14. The assembly of claim 8, wherein the range of angles is 10 to 50 degrees.

15. The assembly of claim 8, wherein the coil is disposed entirely outside the lumen.

16. The assembly of claim 8, wherein the coil implant is configured to axially move relative to the tubular member a distance of at least a length of the attachment member.

* * * * *